United States Patent
Nguyen et al.

(10) Patent No.: US 11,523,838 B2
(45) Date of Patent: Dec. 13, 2022

(54) RETRIEVAL OF MATERIAL FROM CORPOREAL LUMENS

(71) Applicant: Covidien LP, Mansfield, MA (US)

(72) Inventors: Hoai Nguyen, Westminster, CA (US); Gaurav Girdhar, Ladera Ranch, CA (US); Andyanhdzung Huynh, Westminster, CA (US); Ujwal Jalgaonkar, Irvine, CA (US); Eric Mintz, Newport Coast, CA (US); Ashok Nageswaran, Irvine, CA (US); John Wainwright, Foothill Ranch, CA (US)

(73) Assignee: COVIDIEN LP, Mansfield, MA (US)

( * ) Notice: Subject to any disclaimer, the term of this patent is extended or adjusted under 35 U.S.C. 154(b) by 228 days.

(21) Appl. No.: 16/439,642

(22) Filed: Jun. 12, 2019

(65) Prior Publication Data
US 2020/0390455 A1    Dec. 17, 2020

(51) Int. Cl.
*A61B 17/221*    (2006.01)
*A61B 17/22*    (2006.01)
(Continued)

(52) U.S. Cl.
CPC ............ *A61B 17/221* (2013.01); *A61L 29/02* (2013.01); *A61B 2017/2212* (2013.01); *A61B 2017/22094* (2013.01); *A61M 2025/0042* (2013.01)

(58) Field of Classification Search
CPC ........ A61B 17/221; A61B 2017/22094; A61B 2017/2212; A61B 2017/2215;
(Continued)

(56) References Cited

U.S. PATENT DOCUMENTS 4,538,622 A * 9/1985 Samson .......... A61M 25/09033
                                                604/170.01
5,167,239 A * 12/1992 Cohen .................. A61M 25/09
                                                604/908
(Continued)

FOREIGN PATENT DOCUMENTS

EP    1484025 A1    12/2004
EP    2319575 B1    11/2013
(Continued)

OTHER PUBLICATIONS

International Search Report and Written Opinion dated May 25, 2020, International Application No. PCT/US20/22463, 10 pages.
(Continued)

*Primary Examiner* — Kathleen S Holwerda
*Assistant Examiner* — Kankindi Rwego
(74) *Attorney, Agent, or Firm* — Fortem IP LLP; Mary Fox

(57) ABSTRACT

Retrieval of material from vessel lumens can be improved by use of a distal element comprising an expandable mesh, a treatment device includes an elongated member having a proximal portion and a distal portion configured to be positioned within a blood vessel at a treatment site at or near a thrombus. A distal element comprising an expandable mesh is coupled to the distal portion of the elongated member via a connection assembly. In an expanded state, at least a portion of the mesh is configured to be in apposition with the blood vessel wall at the treatment site to anchor or stabilize the elongated member with respect to the blood vessel. The distal element can be electrically coupled to an extracorporeal current generator.

18 Claims, 27 Drawing Sheets

(51) Int. Cl.
*A61M 25/00* (2006.01)
*A61L 29/02* (2006.01)

(58) Field of Classification Search
CPC .. A61B 2017/2217; A61M 2025/0042; A61M 25/09; A61M 2025/09175; A61M 2025/09183; A61M 2025/09191; A61F 2/0103; A61F 2/0105; A61F 2/013; A61F 2/014; A61F 2/01; A61F 2/95; A61F 2002/9528; A61F 2002/9534
USPC .......................................................... 606/200
See application file for complete search history.

(56) References Cited

U.S. PATENT DOCUMENTS

| | | | |
|---|---|---|---|
| 5,928,260 A * | 7/1999 | Chin | A61B 17/1204 606/200 |
| 6,059,779 A | 5/2000 | Mills | |
| 6,315,794 B1 | 11/2001 | Richter | |
| 6,663,650 B2 | 12/2003 | Sepetka et al. | |
| 7,094,249 B1 | 8/2006 | Broome et al. | |
| 7,556,624 B2 | 7/2009 | Laufer et al. | |
| 8,038,674 B2 | 10/2011 | Schmaltz | |
| 8,382,821 B2 | 2/2013 | Richter | |
| 8,603,014 B2 | 12/2013 | Alleman et al. | |
| 8,837,800 B1 | 9/2014 | Bammer et al. | |
| 8,888,788 B2 | 11/2014 | Adams et al. | |
| 8,965,534 B2 | 2/2015 | Hyatt et al. | |
| 9,039,753 B2 | 5/2015 | Thramann | |
| 9,119,656 B2 | 9/2015 | Bose et al. | |
| 9,126,018 B1 | 9/2015 | Garrison | |
| 9,211,132 B2 | 12/2015 | Bowman | |
| 9,241,699 B1 | 1/2016 | Kume et al. | |
| 9,265,512 B2 | 2/2016 | Garrison et al. | |
| 9,308,007 B2 | 4/2016 | Cully et al. | |
| 9,399,118 B2 | 7/2016 | Kume et al. | |
| 9,445,828 B2 | 9/2016 | Turjman et al. | |
| 9,445,829 B2 | 9/2016 | Brady et al. | |
| 9,492,637 B2 | 11/2016 | Garrison et al. | |
| 9,539,022 B2 | 1/2017 | Bowman | |
| 9,561,345 B2 | 2/2017 | Garrison et al. | |
| 9,579,119 B2 | 2/2017 | Cully et al. | |
| 9,585,741 B2 | 3/2017 | Ma | |
| 9,642,635 B2 | 5/2017 | Vale et al. | |
| 9,655,633 B2 | 5/2017 | Leynov et al. | |
| 9,681,882 B2 | 6/2017 | Wilson et al. | |
| 9,737,318 B2 | 8/2017 | Monstadt et al. | |
| 9,770,251 B2 | 9/2017 | Bowman et al. | |
| 9,795,400 B2 | 10/2017 | Davidson | |
| 9,801,643 B2 | 10/2017 | Hansen et al. | |
| 9,827,084 B2 | 11/2017 | Bonnette et al. | |
| 9,861,783 B2 | 1/2018 | Garrison et al. | |
| 9,993,257 B2 | 6/2018 | Losordo et al. | |
| 10,028,782 B2 | 7/2018 | Orion | |
| 10,029,008 B2 | 7/2018 | Creighton | |
| 10,039,906 B2 | 8/2018 | Kume et al. | |
| 10,709,463 B2 | 7/2020 | Girdhar et al. | |
| 2001/0001314 A1 | 5/2001 | Davison et al. | |
| 2001/0011182 A1 | 8/2001 | Dubrul et al. | |
| 2002/0133111 A1 | 9/2002 | Shadduck et al. | |
| 2002/0138094 A1 | 9/2002 | Borillo et al. | |
| 2003/0088245 A1 | 5/2003 | Woloszko et al. | |
| 2003/0135232 A1 * | 7/2003 | Douk | A61B 17/12022 606/200 |
| 2005/0090857 A1 * | 4/2005 | Kusleika | A61F 2/013 606/200 |
| 2007/0005105 A1 | 1/2007 | Kusleika et al. | |
| 2007/0208367 A1 | 9/2007 | Fiorella et al. | |
| 2008/0045881 A1 | 2/2008 | Teitelbaum et al. | |
| 2008/0262489 A1 | 10/2008 | Steinke et al. | |
| 2008/0294181 A1 | 11/2008 | Wensel et al. | |
| 2009/0054918 A1 | 2/2009 | Henson | |
| 2009/0069828 A1 | 3/2009 | Martin et al. | |
| 2009/0112228 A1 | 4/2009 | Deshpande et al. | |
| 2009/0198269 A1 | 8/2009 | Hannes et al. | |
| 2009/0318892 A1 * | 12/2009 | Aboytes | A61M 25/00 604/510 |
| 2009/0318943 A1 | 12/2009 | Eidenschink et al. | |
| 2010/0042136 A1 | 2/2010 | Berrada et al. | |
| 2010/0228280 A1 * | 9/2010 | Groothuis | A61M 25/104 606/200 |
| 2010/0256627 A1 | 10/2010 | Ma et al. | |
| 2011/0196478 A1 | 8/2011 | Torosoff | |
| 2011/0202085 A1 * | 8/2011 | Loganathan | A61B 17/12022 606/200 |
| 2011/0301594 A1 | 12/2011 | Orion et al. | |
| 2012/0101560 A1 * | 4/2012 | Kluck | A61M 29/02 623/1.11 |
| 2013/0030461 A1 | 1/2013 | Marks et al. | |
| 2013/0072960 A1 | 3/2013 | Schneider et al. | |
| 2013/0281788 A1 | 10/2013 | Garrison | |
| 2013/0282084 A1 | 10/2013 | Mathur et al. | |
| 2013/0317589 A1 * | 11/2013 | Martin | A61B 17/3207 623/1.2 |
| 2013/0345739 A1 | 12/2013 | Brady et al. | |
| 2014/0172001 A1 * | 6/2014 | Becking | A61B 17/12113 606/191 |
| 2014/0257362 A1 | 9/2014 | Eidenschink | |
| 2014/0276074 A1 | 9/2014 | Warner | |
| 2014/0277013 A1 | 9/2014 | Sepetka et al. | |
| 2014/0277079 A1 | 9/2014 | Vale et al. | |
| 2014/0309673 A1 | 10/2014 | Dacuycuy et al. | |
| 2014/0309675 A1 | 10/2014 | Maisano et al. | |
| 2014/0343595 A1 | 11/2014 | Monstadt et al. | |
| 2014/0364896 A1 | 12/2014 | Consigny | |
| 2015/0112321 A1 | 4/2015 | Cadouri | |
| 2015/0150672 A1 * | 6/2015 | Ma | A61B 17/12036 606/200 |
| 2015/0297250 A1 | 10/2015 | Farhat et al. | |
| 2015/0297251 A1 | 10/2015 | Sos | |
| 2015/0359547 A1 | 12/2015 | Vale et al. | |
| 2016/0008003 A1 * | 1/2016 | Kleshinski | A61B 17/12172 606/200 |
| 2016/0015402 A1 | 1/2016 | Brady et al. | |
| 2016/0015935 A1 | 1/2016 | Chan et al. | |
| 2016/0106448 A1 | 4/2016 | Brady et al. | |
| 2016/0106449 A1 | 4/2016 | Brady et al. | |
| 2016/0113663 A1 | 4/2016 | Brady et al. | |
| 2016/0113665 A1 | 4/2016 | Brady et al. | |
| 2016/0151618 A1 | 6/2016 | Powers et al. | |
| 2016/0157985 A1 | 6/2016 | Vo et al. | |
| 2016/0199620 A1 | 7/2016 | Pokorney et al. | |
| 2016/0228681 A1 | 8/2016 | Di Palma et al. | |
| 2016/0228684 A1 | 8/2016 | Martin | |
| 2016/0296690 A1 | 10/2016 | Kume et al. | |
| 2016/0302808 A1 | 10/2016 | Loganathan et al. | |
| 2016/0331377 A1 | 11/2016 | Divino et al. | |
| 2016/0375180 A1 | 12/2016 | Anzai | |
| 2017/0079766 A1 | 3/2017 | Wang et al. | |
| 2017/0079767 A1 | 3/2017 | Leon-Yip | |
| 2017/0086862 A1 | 3/2017 | Vale et al. | |
| 2017/0100143 A1 | 4/2017 | Grandfield | |
| 2017/0105743 A1 | 4/2017 | Vale et al. | |
| 2017/0164963 A1 | 6/2017 | Goyal | |
| 2017/0215902 A1 | 8/2017 | Leynov et al. | |
| 2017/0215955 A1 | 8/2017 | Hancock et al. | |
| 2017/0224953 A1 | 8/2017 | Tran et al. | |
| 2017/0281909 A1 | 10/2017 | Northrop et al. | |
| 2017/0290599 A1 | 10/2017 | Youn et al. | |
| 2017/0311963 A1 | 11/2017 | Farhat et al. | |
| 2017/0367707 A1 | 12/2017 | Divino | |
| 2018/0049762 A1 | 2/2018 | Seip et al. | |
| 2018/0084982 A1 | 3/2018 | Yamashita et al. | |
| 2018/0116717 A1 | 5/2018 | Taff et al. | |
| 2018/0132876 A1 | 5/2018 | Zaidat | |
| 2018/0133436 A1 | 5/2018 | Garrison et al. | |
| 2018/0140314 A1 | 5/2018 | Goyal et al. | |
| 2018/0140315 A1 | 5/2018 | Bowman et al. | |
| 2018/0140354 A1 | 5/2018 | Lam et al. | |
| 2018/0161541 A1 | 6/2018 | Haldis et al. | |
| 2018/0185614 A1 | 7/2018 | Garrison et al. | |
| 2018/0200040 A1 | 7/2018 | Wasdyke et al. | |

(56) References Cited

U.S. PATENT DOCUMENTS

| | | |
|---|---|---|
| 2018/0236221 A1 | 8/2018 | Opie et al. |
| 2018/0303595 A1 | 10/2018 | Opie et al. |
| 2018/0344970 A1 | 12/2018 | Kornowski et al. |
| 2019/0038438 A1 | 2/2019 | John et al. |
| 2019/0046119 A1 | 2/2019 | Oxley |
| 2019/0175199 A1 | 6/2019 | Girdhar et al. |
| 2019/0175200 A1 | 6/2019 | Girdhar et al. |
| 2019/0262069 A1 | 8/2019 | Taff et al. |
| 2019/0388097 A1 | 12/2019 | Girdhar et al. |
| 2019/0388107 A1 | 12/2019 | Girdhar et al. |
| 2019/0388111 A1 | 12/2019 | Nguyen et al. |
| 2019/0388112 A1 | 12/2019 | Nguyen et al. |
| 2020/0054392 A1 | 2/2020 | Whiteley et al. |
| 2020/0297410 A1 | 9/2020 | Nguyen et al. |
| 2020/0390456 A1 | 12/2020 | Nguyen et al. |
| 2020/0390457 A1 | 12/2020 | Nageswaran et al. |
| 2020/0390458 A1 | 12/2020 | Nguyen et al. |
| 2021/0177427 A1 | 6/2021 | Nguyen et al. |
| 2021/0177442 A1 | 6/2021 | Girdhar et al. |
| 2021/0186540 A1 | 6/2021 | Taff et al. |

FOREIGN PATENT DOCUMENTS

| | | |
|---|---|---|
| EP | 2490764 B1 | 9/2014 |
| EP | 2967605 A1 | 1/2016 |
| EP | 3184067 A1 | 6/2017 |
| JP | 10290805 A | 11/1998 |
| JP | 2014004219 A | 1/2014 |
| JP | 2018118132 A | 8/2018 |
| KR | 20180102877 A | 9/2018 |
| WO | 2010061376 A1 | 6/2010 |
| WO | 2014079148 A1 | 5/2014 |
| WO | 2015141317 A1 | 9/2015 |
| WO | 2016198947 A1 | 12/2016 |
| WO | 2017192999 A1 | 11/2017 |
| WO | 2018019829 A1 | 2/2018 |
| WO | 2018033401 A1 | 2/2018 |
| WO | 2018046408 A2 | 3/2018 |
| WO | 2018127796 A1 | 7/2018 |
| WO | 2018137029 A1 | 8/2018 |
| WO | 2018137030 A1 | 8/2018 |
| WO | 2018145212 A1 | 8/2018 |
| WO | 2018156813 A1 | 8/2018 |
| WO | 2018172891 A1 | 9/2018 |
| WO | 2018187776 A1 | 10/2018 |
| WO | 2019102307 A1 | 5/2019 |
| WO | 2019246377 A2 | 12/2019 |

OTHER PUBLICATIONS

Fort, Stephen, et al., "'Fused-Gold' vs. 'Bare' stainless steel NIRflex stents of the same geometric design in diseased native coronary arteries. Long-term results from the NIR TOP Study", Euro Interv 2007; 3:256-261.

International Search Report and Written Opinion dated Nov. 3, 2020, International Application No. PCT/US20/70142, 18 pages.

International Search Report and Written Opinion dated Feb. 26, 2021; International Application No. PCT/US20/63200; 14 pages.

* cited by examiner

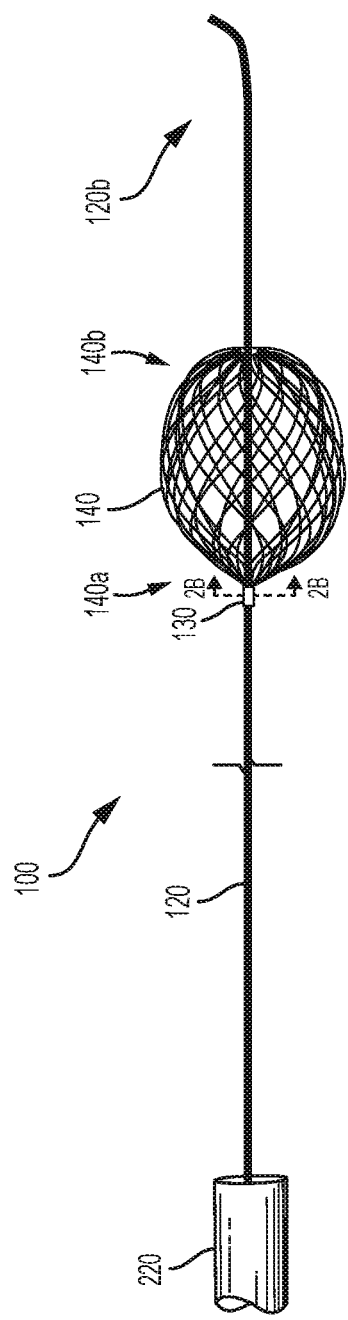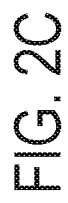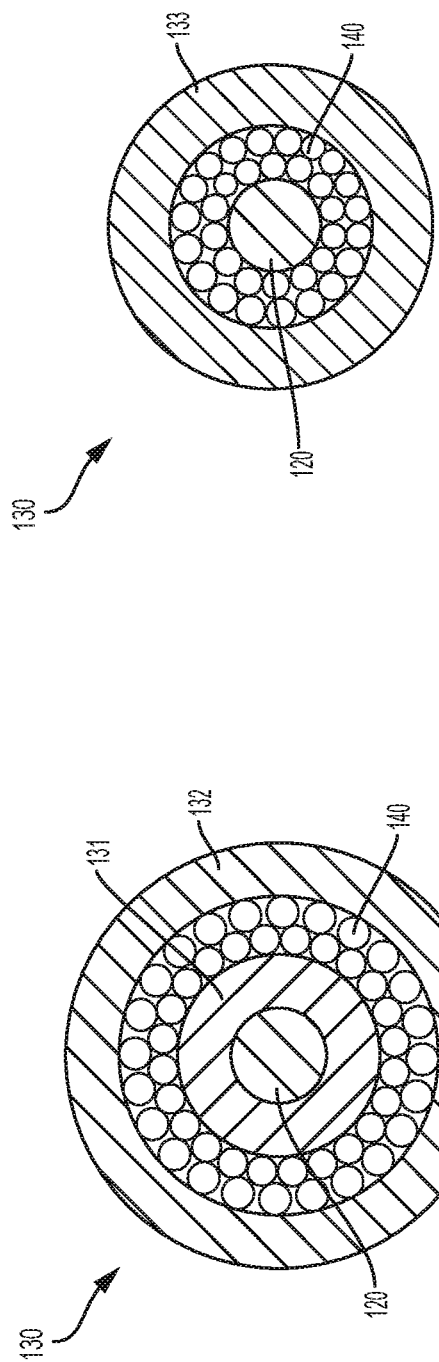

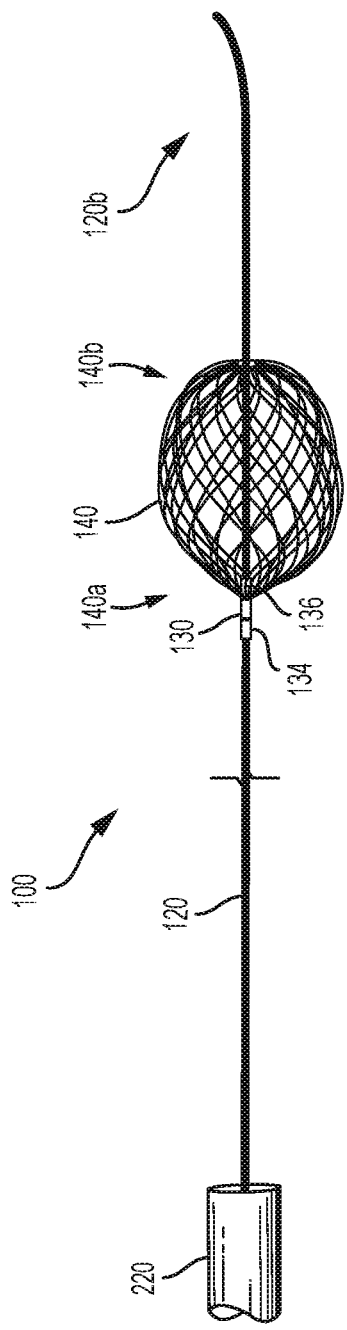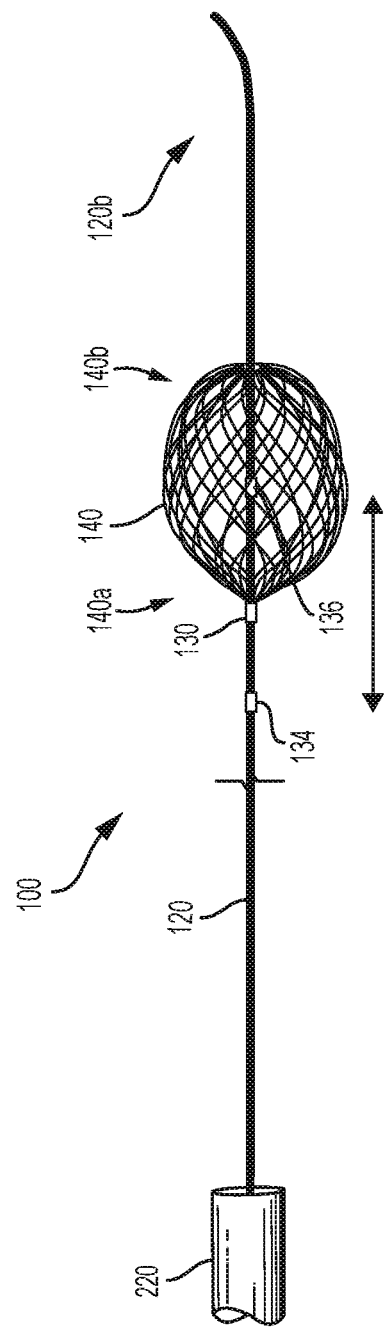

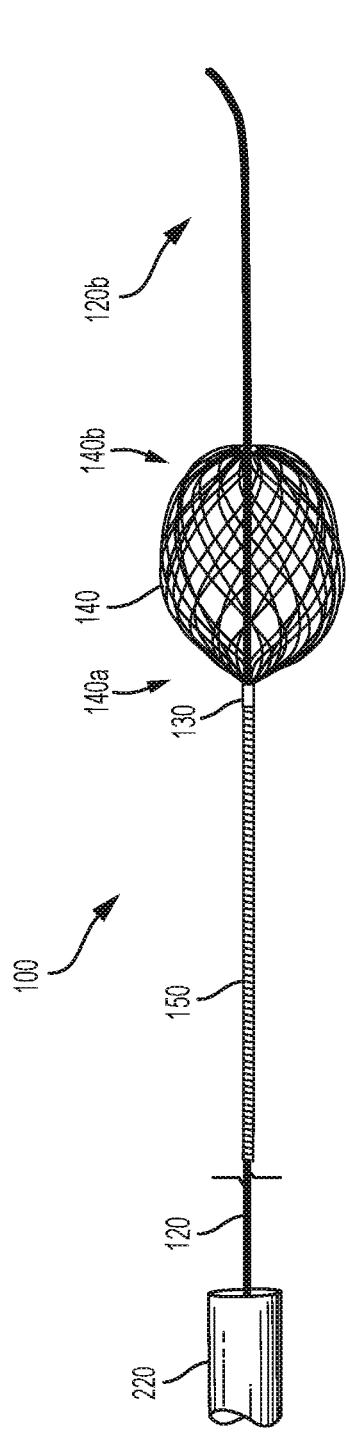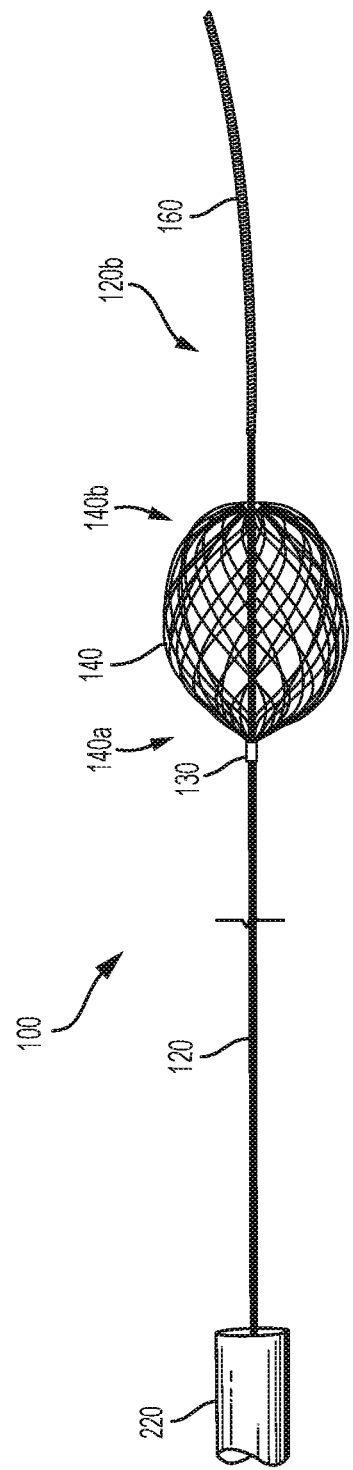
FIG. 5A
FIG. 5B

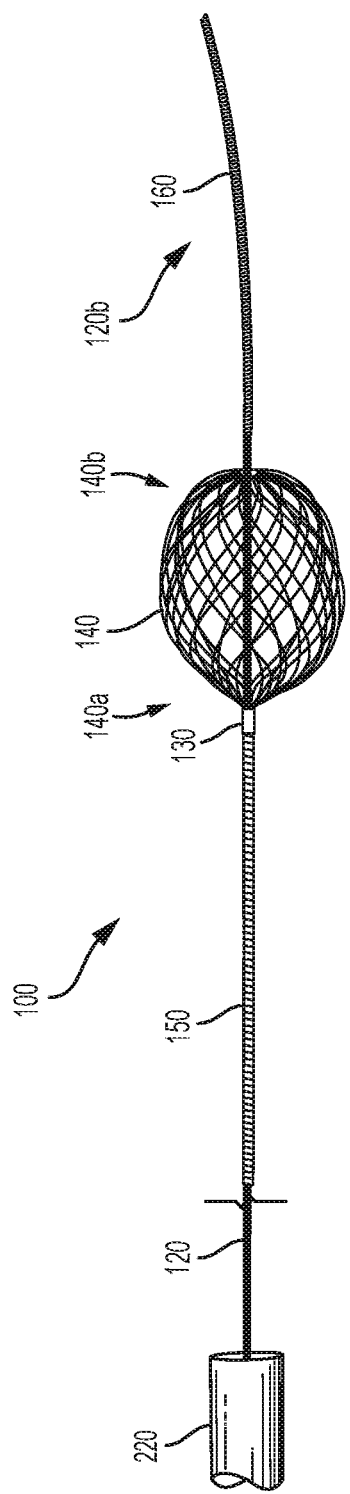
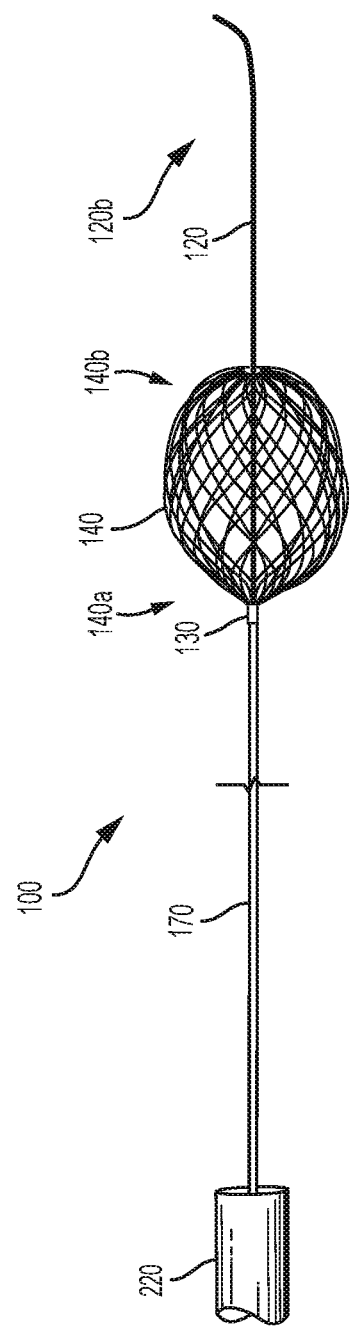

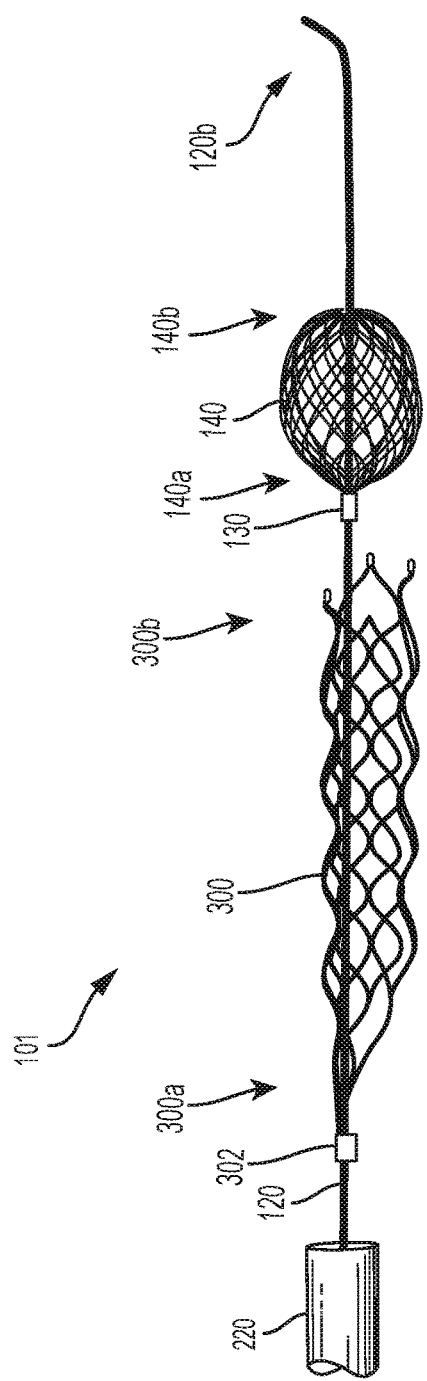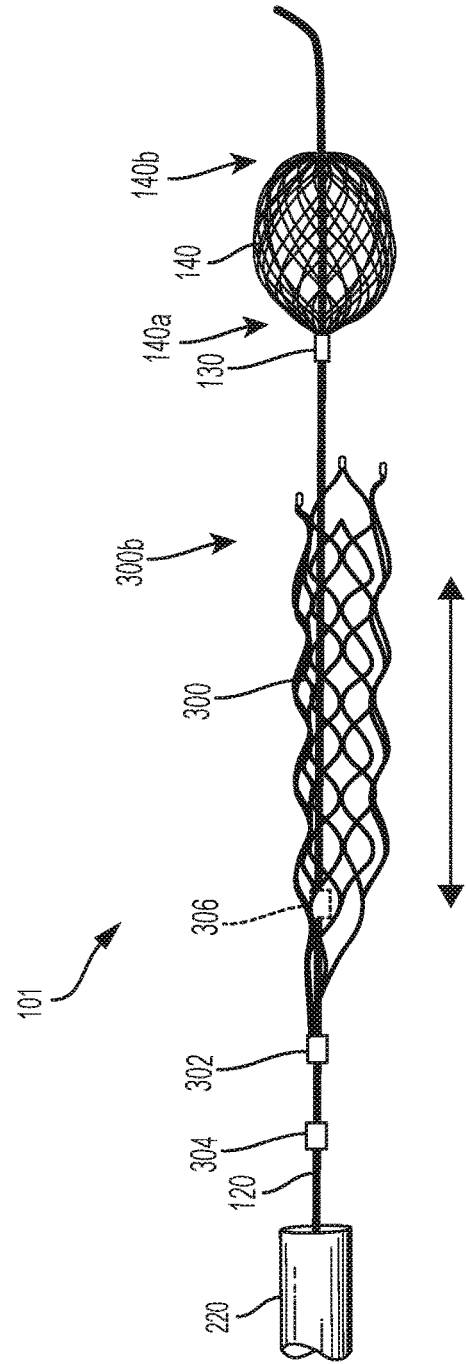

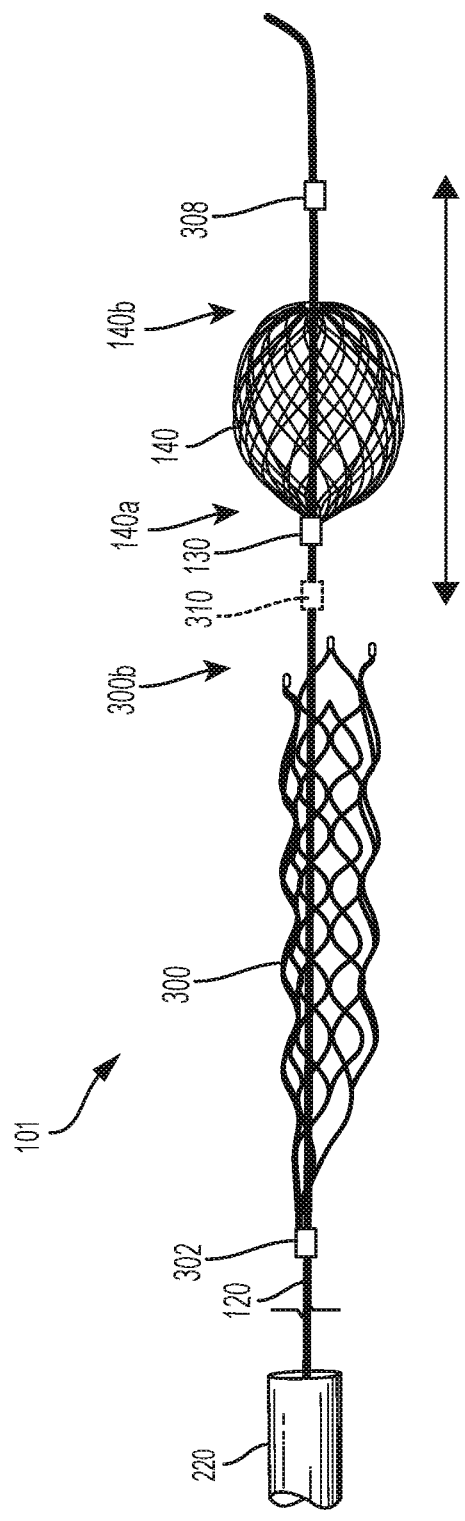
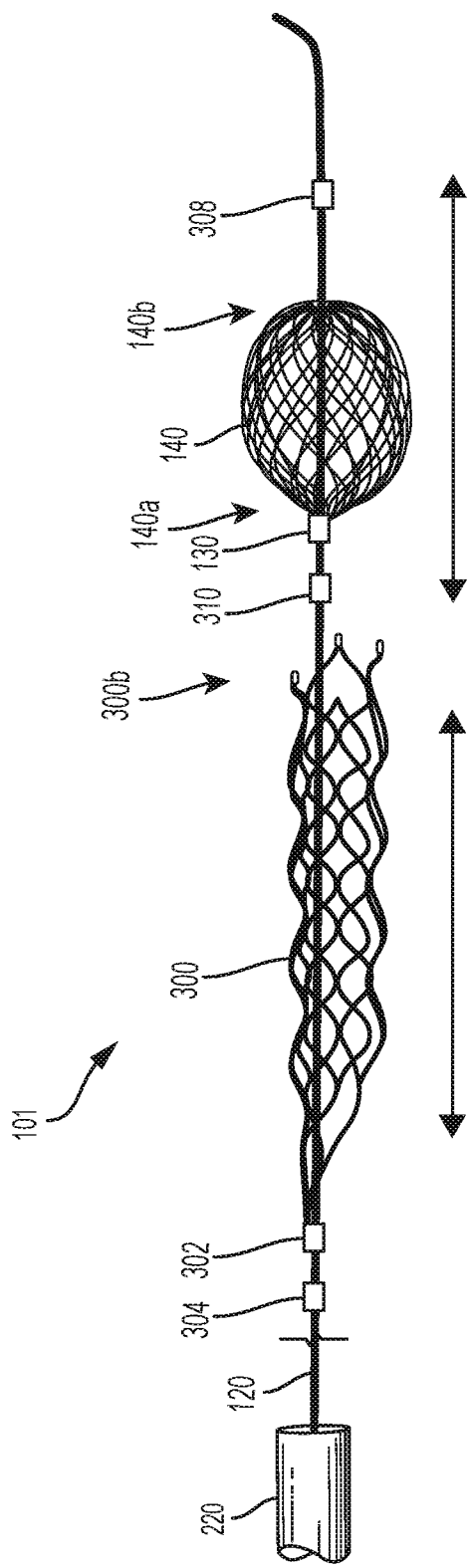
FIG.14
FIG.15

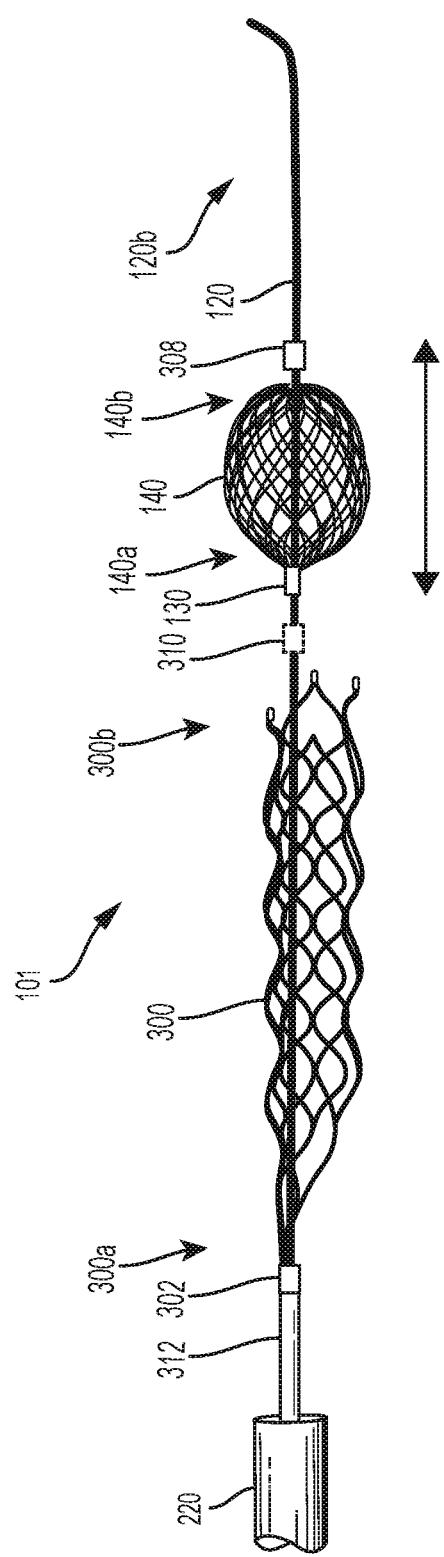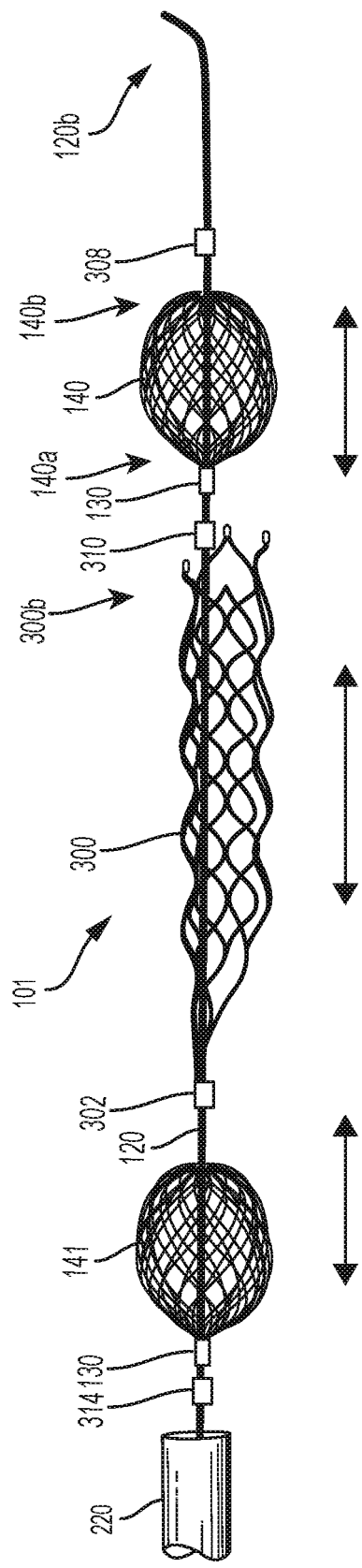

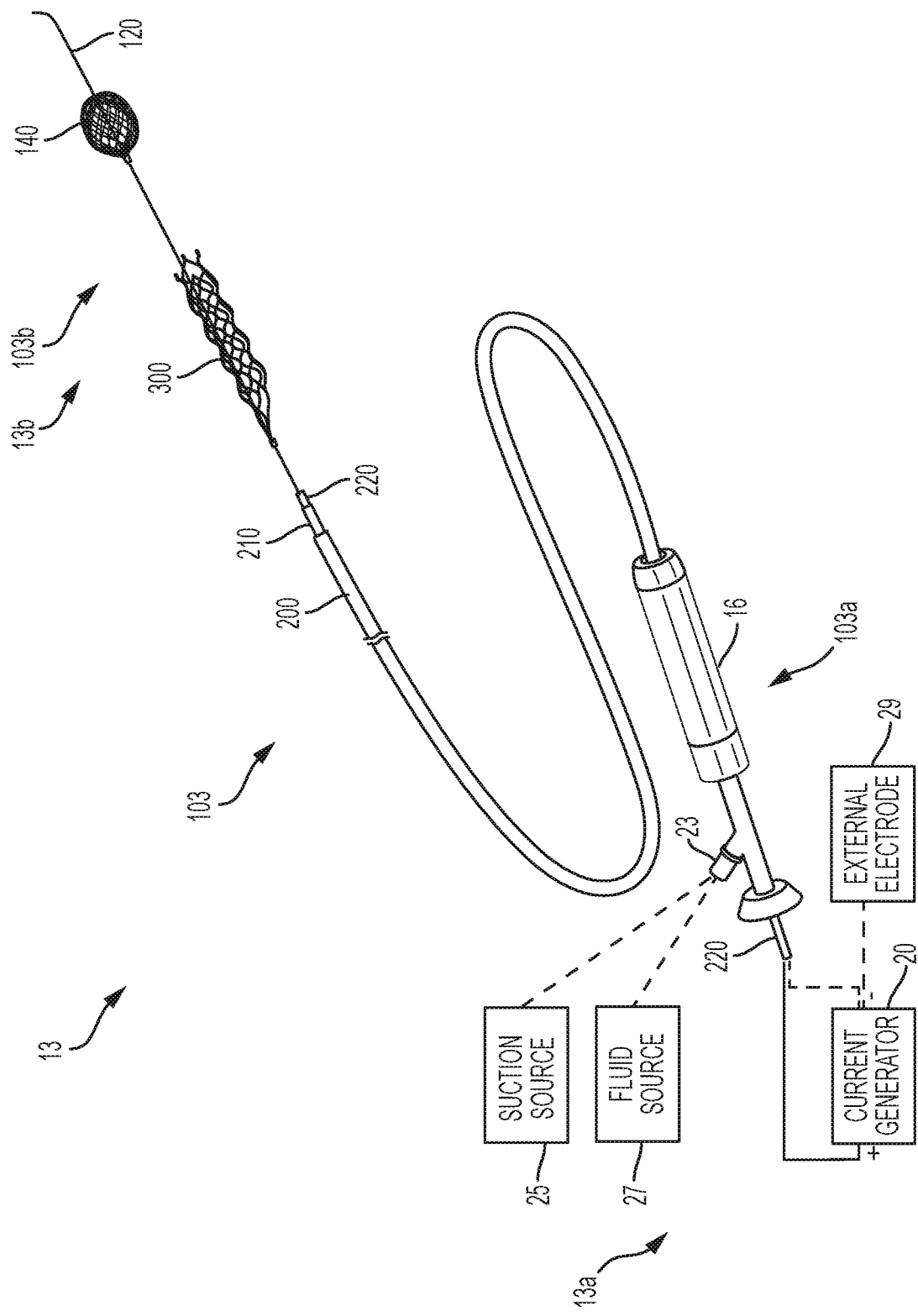

RETRIEVAL OF MATERIAL FROM CORPOREAL LUMENS

CROSS-REFERENCE TO RELATED APPLICATIONS

The present application incorporates by reference in their entireties each of the following commonly owned applications: U.S. patent application Ser. No. 12/427,620, filed Apr. 21, 2009; U.S. patent application Ser. No. 12/942,209, filed Nov. 9, 2010; U.S. patent application Ser. No. 15/838,214, filed Dec. 11, 2017; U.S. patent application Ser. No. 15/838,230, filed Dec. 11, 2017; U.S. patent application Ser. No. 16/024,367, filed Jun. 29, 2018; U.S. patent application Ser. No. 16/024,388, filed Jun. 29, 2018; U.S. patent application Ser. No. 16/024,408, filed Jun. 29, 2018; and U.S. patent application Ser. No. 16/024,429, filed Jun. 29, 2018.

TECHNICAL FIELD

The present technology relates generally to devices and methods for removing obstructions from body lumens. Some embodiments of the present technology relate to devices and methods for removing clot material from blood vessels.

BACKGROUND

Many medical procedures use medical device(s) to remove an obstruction (such as clot material) from a body lumen, vessel, or other organ. An inherent risk in such procedures is that mobilizing or otherwise disturbing the obstruction can potentially create further harm if the obstruction or a fragment thereof dislodges from the retrieval device. If all or a portion of the obstruction breaks free from the device and flows downstream, it is highly likely that the free material will become trapped in smaller and more tortuous anatomy. In many cases, the physician will no longer be able to use the same retrieval device to again remove the obstruction because the device may be too large and/or immobile to move the device to the site of the new obstruction.

Procedures for treating ischemic stroke by restoring flow within the cerebral vasculature are subject to the above concerns. The brain relies on its arteries and veins to supply oxygenated blood from the heart and lungs and to remove carbon dioxide and cellular waste from brain tissue. Blockages that interfere with this blood supply eventually cause the brain tissue to stop functioning. If the disruption in blood occurs for a sufficient amount of time, the continued lack of nutrients and oxygen causes irreversible cell death. Accordingly, it is desirable to provide immediate medical treatment of an ischemic stroke.

To access the cerebral vasculature, a physician typically advances a catheter from a remote part of the body (typically a leg) through the abdominal vasculature and into the cerebral region of the vasculature. Guidewires are used during the procedure to facilitate navigation of a catheter (and/or associated treatment device) to portion of the blood vessel proximate the targeted thrombus. For example, the physician may navigate the vasculature to the treatment site with the guidewire, then advance one or more catheters or other devices over the guidewire to the site. Guidewires may also be used to facilitate exchanging of devices. For instance, a physician may replace the original catheter with another catheter, or a separate device having different properties or better suited for the intended procedure (e.g. better condition, more navigable, better supporting, etc.).

Once within the cerebral vasculature, the physician deploys a device for retrieval of the obstruction causing the blockage. Concerns about dislodged obstructions or the migration of dislodged fragments increases the duration of the procedure at a time when restoration of blood flow is paramount. Furthermore, a physician might be unaware of one or more fragments that dislodge from the initial obstruction and cause blockage of smaller more distal vessels.

Many physicians currently perform thrombectomies (i.e. clot removal) with stents to resolve ischemic stroke. Typically, the physician deploys a stent into the clot in an attempt to push the clot to the side of the vessel and re-establish blood flow. Tissue plasminogen activator ("tPA") is often injected into the bloodstream through an intravenous line to break down a clot. However, it takes time for the tPA to reach the clot because the tPA must travel through the vasculature and only begins to break up the clot once it reaches the clot material. tPA is also often administered to supplement the effectiveness of the stent. Yet, if attempts at clot dissolution are ineffective or incomplete, the physician can attempt to remove the stent while it is expanded against or enmeshed within the clot. In doing so, the physician must effectively drag the clot through the vasculature, in a proximal direction, into a guide catheter located within vessels in the patient's neck (typically the carotid artery). While this procedure has been shown to be effective in the clinic and easy for the physician to perform, there remain some distinct disadvantages to using this approach.

For example, one disadvantage is that the stent may not sufficiently retain the clot as it pulls the clot to the catheter. In such a case, some or all of the clot might remain in the vasculature. Another risk is that, as the stent mobilizes the clot from the original blockage site, the clot might not adhere to the stent as the stent is withdrawn toward the catheter. This is a particular risk when passing through bifurcations and tortuous anatomy. Furthermore, blood flow can carry the clot (or fragments of the clot) into a branching vessel at a bifurcation. If the clot is successfully brought to the end of the guide catheter in the carotid artery, yet another risk is that the clot may be "stripped" or "sheared" from the stent as the stent enters the guide catheter.

In view of the above, there remains a need for improved devices and methods that can remove occlusions from body lumens and/or vessels.

SUMMARY

The present technology relates generally to devices and methods for removing obstructions from body lumens. Aspects of the present technology include a treatment system for removing clot material from blood vessels. In some embodiments, the treatment system comprises a treatment device and one or more catheters. The treatment device may include an elongated member and an expandable distal element coupled to a distal region of the elongated member. The distal element may provide several functions throughout the procedure to facilitate clot retrieval. For example, deployment of the distal element within a blood vessel can anchor a distal region of the treatment device at the deployed location. Such anchoring may be beneficial for navigating the tortuous vasculature (such as the cerebral vasculature) to the site of the thrombus, and may also help align, straighten, or stabilize one or more delivery system components associated with the treatment device, such as a microcatheter or aspiration catheter. In addition, the distal elements of the present technology may be utilized in conjunction with an aspiration catheter to push clot material towards the aspiration catheter, and also as a distal embolic filter.

The present technology is illustrated, for example, according to various aspects described below. Various examples of aspects of the present technology are described as numbered clauses (1, 2, 3, etc.) for convenience. These are provided as examples and do not limit the present technology. It is noted that any of the dependent clauses may be combined in any combination, and placed into a respective independent clause, e.g., clause (1, 73, 77, etc.). The other clauses can be presented in a similar manner.

1. A treatment device, comprising:
    an elongated member having a proximal portion and a distal portion configured to be positioned within a blood vessel at a treatment site at or near a thrombus;
    a distal element coupled to the distal portion of the elongated member via a connection assembly, the distal element comprising an expandable mesh having a constrained state for delivery to the treatment site and an expanded state in which at least a portion of the mesh is configured to be in apposition with the blood vessel wall at the treatment site,
    wherein the distal element is configured to expand into contact with the blood vessel wall at the treatment site and anchor and/or stabilize the elongated member within the blood vessel.

2. The treatment device of any one of the previous Clauses, wherein the distal element is configured to rotate about the elongated member.

3. The treatment device of any one of the previous Clauses, wherein the connection assembly is configured to rotate about the elongated member.

4. The treatment device of any one of the previous Clauses, wherein the connection assembly and/or the distal element is configured to rotate about 360 degrees of a circumference of the elongated member.

5. The treatment device of any one of the previous Clauses, wherein the distal element has a first end and a second end and is configured to rotate about the elongated member, and wherein at least one of the first end or the second end is substantially fixed at a location along a length of the elongated member.

6. The treatment device of any one of the previous Clauses, wherein the distal element has a first end and a second end and is configured to rotate about the elongated member, and wherein at least one of the first end or the second end is configured to move axially along the elongated member.

7. The treatment device of any one of the previous Clauses, wherein the distal element has a first end and a second end and is configured to rotate about the elongated member, and wherein the first end and the second end are configured to move axially along the elongated member.

8. The treatment device of any one of the previous Clauses, wherein the distal element is configured to move axially along to the elongated member.

9. The treatment device of any one of the previous Clauses, wherein the distal element has a first end and a second end, and wherein both the first and second ends of the distal element can move axially along the elongated member.

10. The treatment device of any one of the previous Clauses, wherein the distal element is rotatably and slidably coupled to the elongated member.

11. The treatment device of any one of the previous Clauses, further comprising a stop coupled to the elongated member proximal of the connection assembly, wherein the stop inhibits proximal movement of the connection assembly along the elongated member beyond the stop.

12. The treatment device of any one of the previous Clauses, further comprising a stop coupled to the elongated member distal of the connection assembly, wherein the stop inhibits distal movement of the connection assembly along the elongated member beyond the stop.

13. The treatment device of any one of the previous Clauses, further comprising:
    a first stop coupled to the elongated member proximal of the connection assembly, wherein the first stop inhibits proximal movement of the connection assembly along the elongated member beyond the first stop; and
    a second stop coupled to the elongated member distal of the connection assembly, wherein the second stop inhibits distal movement of the connection assembly along the elongated member beyond the second stop.

14. The treatment device of any one of the previous Clauses, wherein the first stop is spaced apart from the second stop along the elongated member by a distance that is greater than a length of the connection assembly such that the connection assembly is configured to translate along the elongated member between the first and second stops.

15. The treatment device of any one of the previous Clauses, wherein the elongated member extends through at least a portion of a cavity of the distal element.

16. The treatment device of any one of the previous Clauses, wherein the distal element has an aperture at a distal portion thereof, and wherein the elongated member extends through the aperture.

17. The treatment device of any one of the previous Clauses, wherein the elongated member is a solid metal wire.

18. The treatment device of any one of the previous Clauses, wherein the elongated member comprises an elongated tubular element having a lumen extending therethrough.

19. The treatment device of Clause 18, wherein the elongated tubular element is a hypotube.

20. The treatment device of Clause 18, wherein a distal portion of the elongated tubular element is joined to a proximal portion of the connection assembly.

21. The treatment device of any one of the previous Clauses, further comprising a coil positioned around a region of the elongated member that is proximal to the connection assembly.

22. The treatment device of any one of the previous Clauses, further comprising a coil positioned around a region of the elongated member that is distal to the connection assembly.

23. The treatment device of Clause 22, wherein a proximal end of the coil is distal of the distal element.

24. The treatment device of Clause 22, wherein a proximal end of the coil is proximal of a distal end of the distal element such that at least a portion of the coil and distal element overlap.

25. The treatment device of any one of the previous Clauses, further comprising: (a) a proximal coil positioned around a length of the elongated member that is proximal to the connection assembly, and (b) a distal coil positioned around a length of the elongated member that is distal to the connection assembly.

26. The treatment device of any one of the previous Clauses, wherein the elongated member is a first elongated member and has a groove extending along its length, and wherein the treatment device further comprises a second elongated member configured to be positioned along and within the groove.

27. The treatment device of Clause 26, wherein the groove is a spiral-cut groove.

28. The treatment device of any one of the previous Clauses, wherein the connection assembly comprises a tubular band surrounding a proximal portion of the expandable mesh.

29. The treatment device of any one of the previous Clauses, wherein the band includes a radiopaque material.

30. The treatment device of any one of the previous Clauses, wherein the connection assembly comprises an outer band and an inner band.

31. The treatment device of Clause 30, wherein a proximal portion of the expandable mesh is positioned between the outer band and the inner band.

32. The treatment device of Clause 30 or Clause 31 wherein the inner band surrounds a portion of the elongated member, and wherein the inner band is configured to rotate about the elongated member.

33. The treatment device of any one of the previous Clauses, wherein the distal element is fixed to the elongated member at the connection assembly.

34. The treatment device of any one of the previous Clauses, wherein the distal element comprises the distal-most component of the treatment device.

35. The treatment device of any one of the previous Clauses, wherein the connection assembly is coupled to a distal terminus of the elongated member.

36. The treatment device of any one of the previous Clauses, wherein the expandable mesh comprises a plurality of braided filaments that assume a pre-set, three-dimensional shape in the expanded state.

37. The treatment device of any one of the previous Clauses, wherein the expandable mesh comprises a braid formed of 24, 32, 36, 48, 64, or 72 filaments.

38. The treatment device of any one of the previous Clauses, wherein the expandable mesh comprises a braid formed of a plurality of wires, some or all of which have a diameter of about 0.001 inches (0.00254 cm).

39. The treatment device of any one of the previous Clauses, wherein the expandable mesh comprises a braid formed of a plurality of wires, some or all of which have the same diameter.

40. The treatment device of any one of the previous Clauses, wherein the expandable mesh comprises a braid formed of a plurality of wires, at least some of which have different diameters.

41. The treatment device of any one of the previous Clauses, wherein the expandable mesh forms a closed, globular shape in the expanded state, the mesh having an aperture at a distal portion.

42. The treatment device of any one of the previous Clauses, wherein, in the expanded state, the expandable mesh forms one of a sphere, a prolate spheroid, or an oblate spheroid.

43. The treatment device of any one of the previous Clauses, wherein the expandable mesh comprises an inner layer and an outer layer.

44. The treatment device of any one of the previous Clauses, wherein the expandable mesh comprises an inner layer and an outer layer that meet at a fold at a distal portion of the mesh.

45. The treatment device of Clause 44, wherein the expandable mesh includes an aperture at a distal portion, the aperture being defined by the fold.

46. The treatment device of any one of the previous Clauses, wherein the expandable mesh has a maximum cross-sectional dimension of 3.0 mm, 3.5 mm, 4.0 mm, 4.5 mm, 5.0 mm, 5.5 mm, 6.0 mm, 6.5 mm, 7.0 mm, 7.5 mm, or 8.0 mm.

47. The treatment device of any one of the previous Clauses, wherein the expandable mesh is formed of a plurality of filaments having first and second ends fixed at the connection assembly.

48. The treatment device of any one of the previous Clauses, wherein the expandable mesh is formed of a plurality of filaments formed of an inner core material surrounded by an outer material.

49. The treatment device of Clause 48, wherein the inner core material is a radiopaque material and the outer material is a superelastic material.

50. The treatment device of any one of the previous Clauses, wherein the expandable mesh is a laser-cut tube.

51. The treatment device of any one of the previous Clauses, wherein the expandable mesh extends longitudinally along the elongated member and/or a distal coil.

52. The treatment device of any one of the previous Clauses, wherein the expandable mesh comprises a plurality of filaments.

53. The treatment device of Clause 52, wherein the filaments are interwoven.

54. The treatment device of Clause 52 or Clause 53, wherein the filaments are braided.

55. The treatment device of any one of Clauses 52 to 54, wherein each of the filaments has a first end and a second end opposite the first end, and wherein both the first and second ends of the filaments are fixed relative to one another at the connection assembly.

56. The treatment device of any one of Clauses 52 to 55, wherein each of the filaments terminate at only one end of the distal element.

57. The treatment device of Clause 56, wherein the filaments form an opening at an end of the distal element opposite the only one end.

58. The treatment device of Clause 57, wherein an inverted portion of each of the filaments define the opening.

59. The treatment device of Clause 58, wherein the inverted portions of the filaments are configured to move relative to one another.

60. The treatment device of any one of Clauses 56 to 59, wherein the elongated member and/or a distal coil extends through the opening.

61. The treatment device of any one of Clauses 56 to 60, wherein the filaments are slidable over the elongated member at an end of the distal element opposite the only one end.

62. The treatment device of any one of Clauses 56 to 61, wherein the filaments are unattached to the elongated member at an end of the distal element opposite the only one end.

63. The treatment device of any one of Clauses 56 to 62, wherein the distal element is configured to be positioned at the treatment site such that the only one end of the distal element is positioned between the thrombus and the other end of the distal element.

64. The treatment device of any one of Clauses 56 to 63, wherein the distal element is substantially curved along its entire length.

65. The treatment device of any one of Clauses 52 to 64, wherein each of the filaments extends distally and radially inwardly from an intermediate portion of the expandable mesh to a distal terminus of the expandable mesh.

66. The treatment device of any one of Clauses 52 to 64, wherein each of the filaments extends distally and radially inwardly from an intermediate portion of the expandable mesh to a flattened distal face of the expandable mesh.

67. A treatment system comprising:
the treatment device of any one of Clauses 1 to 66; and
a catheter having a lumen extending therethrough, wherein the treatment device is configured to be slidably disposed within the lumen.

68. A treatment system comprising:
the treatment device of any one of Clauses 1 to 66;
a first catheter having a first lumen extending therethrough, wherein the treatment device is configured to be slidably disposed within the lumen; and
a second catheter having a second lumen extending therethrough, wherein the first catheter is configured to be slidably disposed within the second lumen.

69. The treatment system of Clause 68, further comprising a negative pressure source configured to be coupled to the second lumen to aspirate material through the second lumen.

70. The treatment system of Clause 68, wherein the first catheter is a microcatheter and the second catheter is an aspiration catheter.

71. The treatment system of Clause 68, wherein the first catheter is a microcatheter and the second catheter is a guide catheter.

72. The treatment system of Clause 68, wherein the first catheter is a microcatheter and the second catheter is a balloon guide catheter.

73. A treatment system comprising:
the treatment device of any one of Clauses 1 to 66;
a first catheter having a first lumen extending therethrough, wherein the treatment device is configured to be slidably disposed within the lumen;
a second catheter having a second lumen extending therethrough, wherein the first catheter is configured to be slidably disposed within the second lumen; and
a third catheter having a third lumen extending therethrough, wherein the second catheter is configured to be slidably disposed within the second lumen.

74. The treatment system of Clause 73, further comprising a negative pressure source configured to be coupled to the second lumen to aspirate material from the treatment site through the second lumen.

75. The treatment system of Clause 73, wherein the first catheter is a microcatheter, the second catheter is an aspiration catheter, and the third catheter is a guide catheter.

76. The treatment system of Clause 73, wherein the first catheter is a microcatheter, the second catheter is an aspiration catheter, and the third catheter is a balloon guide catheter.

77. A method for treating a blood vessel, the method comprising:
intravascularly positioning a first catheter within a blood vessel lumen such that a distal end of the first catheter is distal to a targeted thrombus, wherein the first catheter contains a treatment device comprising an elongated member and a distal element coupled to the elongated member, the distal element comprising an expandable mesh;
moving the first catheter relative to the distal element to release the distal element such that the distal element self-expands into apposition with the blood vessel wall at a location distal of the targeted thrombus;
intravascularly positioning a distal end of a second catheter within the blood vessel lumen at a location proximal to the targeted thrombus; and
aspirating a portion of the blood vessel lumen proximate the thrombus via the second catheter.

78. The method of Clause 77, further comprising moving the distal element proximally relative to the distal end of the second catheter such that a proximal portion of the distal element engages a distal portion of the thrombus.

79. The method of Clause 77, further comprising pushing the thrombus towards the distal end of the second catheter with the distal element while aspirating the portion of the blood vessel lumen.

80. The method of Clause 77, further comprising pulling the distal element towards the distal end of the second catheter to push the thrombus into an opening at the distal end of the second catheter while aspirating the portion of the blood vessel lumen.

81. The method of Clause 77, further comprising inhibiting proximal movement of the treatment device while the distal element is expanded within the blood vessel.

82. The method of Clause 77, wherein the distal element is rotatably coupled to the elongated member.

83. The method of Clause 77, wherein the treatment device is any one of the treatment devices of Clauses 1 to 66.

84. A treatment device, comprising:
an elongated member having a proximal portion and a distal portion configured to be positioned within a blood vessel at a treatment site at or near a thrombus; and
a distal element coupled to the distal portion of the elongated member via a connection assembly, the distal element comprising an expandable mesh having a constrained state for delivery to the treatment site and an expanded state, wherein the distal element has an aperture at a distal portion thereof, and wherein the elongated member extends through the aperture,
wherein, in the expanded state, the distal element is configured to expand into contact with the blood vessel wall at the treatment site and anchor and/or stabilize the elongated member within the blood vessel.

85. The treatment device of Clause 84, wherein an edge of the aperture is formed by the mesh.

86. The treatment device of Clause 85, wherein an edge of the aperture is formed by the mesh around an entire perimeter of the aperture.

87. The treatment device of Clause 85, wherein the mesh comprises filaments, and the filaments form the edge of the aperture.

88. The treatment device of Clause 84, wherein the distal element is configured to rotate about the elongated member.

89. The treatment device of Clause 84, wherein the elongated member extends through at least a portion of a cavity of the distal element.

90. The treatment device of Clause 84, wherein the elongated member comprises an elongated tubular element having a lumen extending therethrough.

91. The treatment device of Clause 84, wherein the elongated tubular element is a hypotube.

92. The treatment device of Clause 84, wherein a distal portion of the elongated tubular element is joined to a proximal portion of the connection assembly.

93. The treatment device of Clause 84, further comprising a coil positioned around a region of the elongated member that is proximal to the connection assembly.

94. The treatment device of Clause 84, further comprising a coil positioned around a region of the elongated member that is distal to the connection assembly.

95. The treatment device of Clause 84, wherein the expandable mesh comprises a plurality of filaments.

96. The treatment device of Clause 95, wherein each of the filaments has a first end and a second end opposite the first end, and wherein both the first and second ends of the filaments are fixed relative to one another at the connection assembly.

97. The treatment device of Clause 95, wherein each of the filaments terminate at only one end of the distal element.

98. The treatment device of Clause 97, wherein the filaments form an opening at an end of the distal element opposite the only one end.

99. A method for treating a blood vessel, the method comprising:
   intravascularly positioning a catheter within a blood vessel lumen such that a distal end of the catheter is distal to a targeted thrombus, wherein the catheter contains a treatment device comprising an elongated member and a distal element coupled to the elongated member, the distal element comprising an expandable mesh, the expandable mesh having an aperture at its distal portion;
   moving the catheter relative to the distal element to release the distal element such that the distal element expands into apposition with the blood vessel wall at a location distal of the targeted thrombus, wherein expansion of the distal element causes the aperture of the expandable mesh to move along the elongated member;
   aspirating a portion of the blood vessel lumen proximate the thrombus; and
   moving the distal element proximally relative to the distal end of the catheter such that a proximal portion of the distal element engages a distal portion of the thrombus.

100. The method of Clause 99, wherein the catheter is a first catheter and the method further comprises intravascularly positioning a distal end of a second catheter within the blood vessel lumen at a location proximal to the targeted thrombus, and wherein aspirating a portion of the blood vessel lumen occurs via the second catheter.

101. The method of Clause 100, further comprising pushing the thrombus towards the distal end of the second catheter with the distal element while aspirating the portion of the blood vessel lumen.

102. The method of Clause 100, further comprising pulling the distal element towards the distal end of the second catheter to push the thrombus into an opening at the distal end of the second catheter while aspirating the portion of the blood vessel lumen.

103. The method of Clause 99, further comprising inhibiting proximal movement of the treatment device while the distal element is expanded within the blood vessel.

104. The method of Clause 99, wherein the distal element is rotatably coupled to the elongated member.

105. A treatment device, comprising:
   an elongated member having a proximal portion and a distal portion configured to be positioned within a blood vessel at a treatment site at or near a thrombus; and
   a distal element coupled to the distal portion of the elongated member via a connection assembly, the distal element comprising an expandable mesh having a constrained state for delivery to the treatment site and an expanded state in which at least a portion of the mesh is configured to be in apposition with the blood vessel wall at the treatment site, wherein the distal element has an aperture at a distal portion thereof, and wherein the elongated member extends through the aperture,
   wherein the distal element is configured to expand into contact with the blood vessel wall at the treatment site and anchor and/or stabilize the elongated member within the blood vessel.

106. The treatment device of Clause 105, wherein an edge of the aperture is formed by the mesh.

107. The treatment device of Clause 106, wherein an edge of the aperture is formed by the mesh around an entire perimeter of the aperture.

108. The treatment device of Clause 106, wherein the mesh comprises filaments, and the filaments form the edge of the aperture.

109. The treatment device of Clause 105, wherein the distal element is configured to rotate about the elongated member.

110. The treatment device of Clause 105, wherein the elongated member extends through at least a portion of a cavity of the distal element.

111. The treatment device of Clause 105, wherein the elongated member comprises an elongated tubular element having a lumen extending therethrough.

112. The treatment device of Clause 105, wherein the elongated tubular element is a hypotube.

113. The treatment device of Clause 105, wherein a distal portion of the elongated tubular element is joined to a proximal portion of the connection assembly.

114. The treatment device of Clause 105, further comprising a coil positioned around a region of the elongated member that is proximal to the connection assembly.

115. The treatment device of Clause 105, further comprising a coil positioned around a region of the elongated member that is distal to the connection assembly.

116. The treatment device of Clause 105, wherein the expandable mesh comprises a plurality of filaments.

117. The treatment device of Clause 116, wherein each of the filaments has a first end and a second end opposite the first end, and wherein both the first and second ends of the filaments are fixed relative to one another at the connection assembly.

118. The treatment device of Clause 116, wherein each of the filaments terminate at only one end of the distal element.

119. The treatment device of Clause 118, wherein the filaments form an opening at an end of the distal element opposite the only one end.

120. A method for treating a blood vessel, the method comprising:
   intravascularly positioning a catheter within a blood vessel lumen such that a distal end of the catheter is distal to a targeted thrombus, wherein the catheter contains a treatment device comprising an elongated member and a distal element coupled to the elongated member, the distal element comprising an expandable mesh, the expandable mesh having an aperture at its distal portion;
   moving the catheter relative to the distal element to release the distal element such that the distal element expands into apposition with the blood vessel wall at a location distal of the targeted thrombus, wherein expansion of the distal element causes the aperture of the expandable mesh to move along the elongated member;
   aspirating a portion of the blood vessel lumen proximate the thrombus; and
   moving the distal element proximally relative to the distal end of the catheter such that a proximal portion of the distal element engages a distal portion of the thrombus.

121. The method of Clause 120, wherein the catheter is a first catheter and the method further comprises intravascularly positioning a distal end of a second catheter within the blood vessel lumen at a location proximal to the targeted thrombus, and wherein aspirating a portion of the blood vessel lumen occurs via the second catheter.

122. The method of Clause 121, further comprising pushing the thrombus towards the distal end of the second catheter with the distal element while aspirating the portion of the blood vessel lumen.

123. The method of Clause 121, further comprising pulling the distal element towards the distal end of the second catheter to push the thrombus into an opening at the distal end of the second catheter while aspirating the portion of the blood vessel lumen.

124. The method of Clause 120, further comprising inhibiting proximal movement of the treatment device while the distal element is expanded within the blood vessel.

125. The method of Clause 120, wherein the distal element is rotatably coupled to the elongated member.

126. A treatment device, comprising:
an elongated member including a distal portion configured to be positioned within a blood vessel at a treatment site at or near a thrombus;
a distal element comprising a first expandable mesh and configured to expand from a constrained configuration to an expanded configuration in which at least a portion of the distal element is in apposition with a blood vessel wall at the treatment site or other desired location; and
an interventional element configured to engage the thrombus at the treatment site, the interventional element extending longitudinally over the distal portion of the elongated member and comprising a second expandable mesh, wherein the interventional element is configured to expand from a constrained configuration to an expanded configuration in which at least a portion of the interventional element is in apposition with the blood vessel wall at the treatment site.

127. The device of Clause 126, wherein the distal element is distal to the interventional element.

128. The device of Clause 126, wherein the distal element is proximal to the interventional element.

129. The device of any one of the previous Clauses, wherein the interventional element is coupled to the elongated member such that the interventional element is longitudinally fixed relative to the elongated member.

130. The device of any one of the previous Clauses, wherein the distal element is coupled to the elongated member such that the distal element is longitudinally fixed relative to the elongated member.

131. The device of any one of the previous Clauses, wherein the interventional element is rotatably coupled to the elongated member.

132. The device of any one of the previous Clauses, wherein the distal element is rotatably coupled to the elongated member.

133. The device of any one of the previous Clauses, wherein at least one of the interventional element or the distal element is rotatably coupled to the elongated member.

134. The device of any one of the previous Clauses, further comprising a stop coupled to the elongated member proximal to the interventional element, wherein the interventional element is slidably coupled to the elongated member and movable between the stop and distal element.

135. The device of Clause 132, wherein the stop is a first stop, the device further comprising a second stop coupled to the elongated member between the interventional element and distal element, wherein the interventional element is movable between the first and second stops.

136. The device of Clause 135, further comprising a third stop coupled to the elongated member distal to the distal element, wherein the distal element is slidably coupled to the elongated member and movable between the second and third stops.

137. The device of any one of the previous Clauses, further comprising a stop coupled to the elongated member distal to the distal element, wherein the distal element is slidably coupled to the elongated member and movable between the interventional element and stop.

138. The device of Clause 137, wherein the stop is first stop, the device further comprising a second stop coupled to the elongated member between the interventional element and distal element, wherein the distal element is movable between the first and second stops.

139. The device of any one of the previous Clauses, wherein the distal element is a first distal element, the device further comprising a second distal element proximal to the interventional element.

140. The device of Clause 139, wherein the second distal element is coupled to the elongated member such that the second distal element is longitudinally fixed relative to the elongated member.

141. The device of Clause 139 or Clause 140, wherein the second distal element is rotatably coupled to the elongated member.

142. The device of any one of Clauses 139 to 141, further comprising a stop coupled to the elongated member proximal to the second distal element, wherein the second distal element is slidably coupled to the elongated member and movable between the stop and interventional element.

143. The device of any one of Clauses 139 to 142, wherein the interventional element is slidably coupled to the elongated member and movable between the first and second distal elements.

144. The device of any one of Clauses 139 to 143, wherein the first and second distal elements are substantially identical.

145. The device of any one of the previous Clauses, further comprising a tube extending longitudinally over the elongated member.

146. The device of Clause 145, wherein the tube is coupled to a proximal end portion of the interventional element.

147. The device of Clause 67 or Clause 146, further comprising a proximalmost stop or coupling member coupled to the elongated member, the tube extending longitudinally between the proximalmost stop or coupling member and the interventional element.

148. The device of any one of Clauses 145 to 147, wherein the tube is coupled to a proximal end portion of the distal element.

149. The device of any one of Clauses 145 to 148, wherein the tube includes a helical cut extending along at least a portion of the length of the tube.

150. The device of Clause 149, wherein the helical cut extends along only a portion of the length of the tube.

151. The device of Clause 149 or Clause 150, wherein a proximal end of the helical cut is positioned at an intermediate portion of the tube.

152. The device of Clause 149, wherein the helical cut extends along the substantially entire length of the tube.

153. The device of any one of Clauses 149 to 152, wherein the helical cut includes a first portion having a first pitch and a second portion having a second pitch different than the first pitch.

154. The device of any one of the previous Clauses, wherein the interventional element includes a plurality of braided filaments, the device further comprising a connection assembly extending over the elongated member and coupled to a proximal portion of the plurality of braided filaments.

155. The device of any one of the previous Clauses, wherein the plurality of braided filaments of the interventional element includes a free distal portion.

156. The device of Clause 154 or Clause 155, wherein the plurality of braided filaments of the interventional element includes exposed braid ends.

157. The device of any one of the previous Clauses, wherein the interventional element comprises a working length portion and a non-working length portion, the working length portion being configured to interlock, capture, and/or engage the thrombus.

158. The device of Clause 157, wherein a distal terminus of the working length portion is proximal of a distal terminus of the interventional element.

159. The device of any one of the previous Clauses, wherein the working length portion is spaced apart from a distal terminus of the interventional element.

160. The device of any one of Clauses 157 to 159, wherein the non-working length portion is disposed between a distal end of the elongated member and a proximal end of the working length portion.

161. The device of any one of the previous Clauses, wherein the interventional element comprises a thrombectomy device.

162. The device of any one of the previous Clauses, wherein the interventional element comprises a stent retriever.

163. The device of any one of the previous Clauses, wherein the interventional element comprises a removal device.

164. The device of any one of the previous Clauses, wherein the interventional element is a mesh.

165. The device of any one of the previous Clauses, wherein the interventional element is a laser-cut stent.

166. The device of any one of the previous Clauses, wherein the distal element is any one of the distal elements of the treatment devices of Clauses 1 to 66.

167. The device of any one of the previous Clauses, wherein the elongated member is a first elongated member, the system further comprising a second elongated member extending within the catheter and including a distal region configured to be positioned within the blood vessel at or near a thrombus.

168. The device of Clause 167, wherein the first elongated member is coupled to one of the interventional element or distal element, and wherein the second elongated member is coupled to the other one of the interventional element or distal element.

169. The device of any one of the previous Clauses, wherein the distal element comprises a plurality of braided filaments.

170. The device of any one of the previous Clauses, wherein the distal element comprises an attachment region configured to engage with the thrombus.

171. The device of Clause 170, wherein the attachment region comprises a proximal face of the distal element.

172. The device of Clause 170 or Clause 171, wherein a proximal portion of the distal element comprises the attachment region, and wherein a distal end portion of the distal element comprises a non-attachment region.

173. The device of any one of the previous Clauses, wherein the distal element is coupled to the elongated member at a distal terminus thereof.

174. A treatment system comprising:
the treatment device of any one of Clauses 1 to 66;
a catheter having a lumen extending therethrough, wherein the treatment device is configured to be slidably disposed within the lumen.

175. The system of Clause 174, wherein the catheter is a first catheter, the system further comprising a second catheter configured to be slidably received by the lumen of the first catheter.

176. The system of Clause 175, wherein the first catheter is a guide catheter and the second catheter is a microcatheter.

177. The system of Clause 175 or Clause 176, further comprising a third catheter configured to be slidably received through the lumen of the first catheter.

178. The system of Clause 177, wherein the first catheter is a guide catheter and the third catheter is a distal access catheter.

179. The system of Clause 177, wherein the first catheter is a guide catheter, the second catheter is a microcatheter, and the third catheter is a distal access catheter.

180. The system of Clause 177, wherein the third catheter is an aspiration catheter.

181. The system of Clause 177, wherein the first catheter is a balloon guide catheter and the third catheter is a distal access catheter.

182. The system Clause 177, wherein the first catheter is a guide catheter and the third catheter is a distal access catheter, wherein the distal access catheter includes a flow arrest element configured to expand within the vessel lumen and at least partially arrest blood flow proximal of the thrombus.

183. The system of Clause 182, wherein the distal access catheter is an aspiration catheter.

184. The system of any one of Clauses 174 to 183, wherein:
the first catheter includes a flow arrest element configured to expand to an expanded state within the blood vessel and at least partially arrest blood flow proximal of the thrombus, and
the third catheter is an aspiration catheter configured to apply a negative pressure at the treatment site.

185. A method, comprising:
intravascularly advancing a catheter to a treatment site within a blood vessel proximate a thrombus such that a distal end of the catheter is positioned distal of the thrombus, wherein the catheter contains a treatment device comprising an elongated member, an expandable distal element, and an interventional element;
withdrawing the catheter proximally beyond a proximal end of the distal element, thereby allowing the distal element to self-expand into apposition with the blood vessel wall at a location distal of the thrombus;
continuing to withdraw the catheter proximally beyond a proximal end of the interventional element such that the interventional element self-expands, wherein at least a portion of the interventional element self-expands within the thrombus.

186. The method of Clause 185, wherein the treatment device is any of the treatment devices of Clauses 1 to 49.

187. The method of Clause 185, wherein at least one of the distal element or the interventional element is rotatable relative to the elongated member.

188. The method of Clause 185, wherein one of the interventional element and the distal element is fixedly coupled to the elongated member, and the other of the interventional element and the distal element is free to rotate about and/or translate along the elongated member.

189. The method of Clause 185, wherein both the interventional element and the distal element are configured to translate along the elongated member.

190. The method of Clause 185, wherein the treatment device further comprises an elongated shaft having a lumen extending therethrough, and wherein the interventional element is coupled to a distal portion of the elongated shaft and the distal element is coupled to a distal portion of the elongated member, and wherein the elongated member and the elongated shaft can move axially with respect to one another.

191. The method of Clause 185, wherein the interventional element is a laser-cut tube.

192. The method of Clause 185, wherein the distal element is a braid.

193. The method of Clause 185, further comprising aspirating the thrombus.

194. A treatment device, comprising:
an elongated member including a distal portion configured to be positioned within a blood vessel at a treatment site at or near a thrombus;
a distal element comprising a first expandable mesh and configured to expand from a constrained configuration to an expanded configuration in which at least a portion of the distal element is in apposition with a blood vessel wall at the treatment site or other desired location, the distal element being rotatably coupled to the elongated member; and
an interventional element configured to engage the thrombus at the treatment site, the interventional element extending longitudinally over the distal portion of the elongated member and comprising a second expandable mesh, wherein the interventional element is configured to expand from a constrained configuration to an expanded configuration in which at least a portion of the interventional element is in apposition with the blood vessel wall at the treatment site.

195. The treatment device of Clause 194, further comprising a stop fixedly coupled to the elongated member proximal to the interventional element, wherein the interventional element is slidably coupled to the elongated member and movable between the stop and distal element.

196. The treatment device of Clause 195, wherein the stop is a first stop, the device further comprising a second stop coupled to the elongated member between the interventional element and distal element, wherein the interventional element is movable along the elongated member between the first and second stops.

197. The treatment device of Clause 196, further comprising a third stop coupled to the elongated member distal to the distal element, wherein the distal element is slidably coupled to the elongated member and movable along the elongated member between the second and third stops.

198. The treatment device of Clause 194, wherein the distal element is a first distal element distal to the interventional element, the device further comprising a second distal element proximal to the interventional element.

199. The treatment device of Clause 194, further comprising a tube extending longitudinally over the elongated member.

200. The treatment device of Clause 199, wherein the tube is coupled to a proximal end portion of the interventional element.

201. The treatment device of Clause 199, further comprising a proximalmost stop or coupling member coupled to the elongated member, the tube extending longitudinally between the proximalmost stop or coupling member and the interventional element.

202. The treatment device of Clause 199, wherein the tube is coupled to a proximal end portion of the distal element.

203. The treatment device of Clause 199, wherein the tube includes a helical cut extending along at least a portion of the length of the tube.

204. The treatment device of Clause 194, wherein the interventional element comprises a thrombectomy device.

205. The treatment device of Clause 194, wherein the interventional element comprises a stent retriever.

206. The treatment device of Clause 194, wherein the interventional element is a laser-cut stent.

207. A treatment system, comprising:
an elongated member including a distal portion configured to be positioned within a blood vessel at a treatment site at or near a thrombus;
a distal element configured to expand from a constrained configuration to an expanded configuration in which at least a portion of the distal element is in apposition with a blood vessel wall at the treatment site or other desired location;
an interventional element comprising a stent retriever; and
a tube extending longitudinally over the elongated member.

208. The system of Clause 207, wherein the distal element is configured to prevent or inhibit a portion of the thrombus from migrating distal thereto.

209. The system of Clause 207, further comprising a catheter having a lumen extending therethrough, wherein the distal element and the interventional element are configured to be slidably disposed within the lumen.

210. The system of Clause 209, wherein the catheter is a first catheter, the system further comprising a second catheter configured to be slidably received by the lumen of the first catheter.

211. The system of Clause 210, wherein the first catheter is a guide catheter and the second catheter is a microcatheter.

212. The system of Clause 207, further comprising a proximalmost stop or coupling member coupled to the elongated member, wherein the tube is coupled to a proximal end portion of the interventional element and extends longitudinally between the interventional element and the proximalmost stop or coupling member.

213. The system of Clause 207, further comprising:
a first stop fixedly coupled to the elongated member proximal to the distal element; and
a second stop fixedly coupled to the elongated member distal to the distal element,
wherein
the distal element is slidably coupled to the elongated member and movable along the elongated member between the first and second stops, and
the interventional element is proximal to the distal element and rotatably coupled to the elongated member.

214. A thrombectomy system, comprising:
a catheter having a lumen and a distal portion configured to be positioned adjacent to a thrombus in a blood vessel;
a distal element coupled to a distal portion of an elongated member, the elongated member configured to be electrically coupled to a first terminal of a power supply and to be slidably advanced through the catheter lumen; and
an electrode electrically coupled to a second terminal of the power supply.

215. The system of Clause 194, wherein the distal element comprises any of the distal elements of any of the preceding Clauses.

216. The system of any one of the preceding Clauses, wherein the distal element comprises an attachment portion configured to electrostatically engage with the thrombus.

217. The system of Clause 196, wherein at least part of the attachment portion extends along the elongated member.

218. The system of any one of Clauses 196 to 197, wherein at least part of the attachment portion extends along the elongated member proximal of the distal element.

219. The system of any one of Clauses 196 to 198, wherein the attachment portion is configured to function as an electrode surface.

220. The system of any one of Clauses 196 to 199, wherein the attachment portion defines a conductivity gradient as it extends along a proximal-to-distal direction.

221. The system of Clause 200, wherein the conductivity gradient comprises an increase in conductivity as it extends distally.

222. The system of Clause 200, wherein the conductivity gradient comprises a decrease in conductivity as it extends distally.

223. The system of any one of Clauses 196 to 202, wherein the attachment portion is configured to define a charge density gradient as it extends along a proximal-to-distal direction.

224. The system of Clause 203, wherein the charge density gradient comprises an increase in charge density as it extends distally.

225. The system of Clause 203, wherein the charge density gradient comprises a decrease in charge density as it extends distally.

226. The system of any one of Clauses 196 to 205, wherein the attachment portion is at least partially coated with a conductive material.

227. The system of Clause 206, wherein the coating has a varying thickness or concentration over the attachment portion.

228. The system of any one of Clauses 196 to 207, wherein the attachment portion comprises a coil proximal to the distal element.

229. The system of any one of the preceding Clauses, wherein the catheter is a first catheter and the system further comprises a second catheter and a third catheter, wherein the first catheter is configured to be slidably disposed within a lumen of the second catheter, and the second catheter is configured to be slidably disposed within a lumen of the third catheter.

230. The system of any one of the preceding Clauses, further comprising a suction source configured to supply negative pressure through the catheter to aspirate a region adjacent to the distal portion of the catheter.

231. The system of any one of the preceding Clauses, wherein the attachment portion comprises a proximal face of the distal element.

232. The system of any one of the preceding Clauses, wherein a proximal portion of the distal element comprises the attachment portion and wherein a distal end portion of the distal element comprises a non-attachment portion.

233. The system of any one of the preceding Clauses, wherein the attachment portion is more conductive than other portions of the distal element.

234. The system of any one of the preceding Clauses, wherein the attachment portion is at least partially coated with a conductive material.

235. The system of Clause 214, wherein the conductive material comprises gold.

236. The system of Clause 214, wherein the coating has a varying thickness or concentration over the attachment portion.

237. The system of any one of the preceding Clauses, wherein non-attachment portions are coated with an insulating material.

238. The system of any one of the preceding Clauses, wherein the attachment portion comprises a coil proximal to the distal element.

239. The system of any one of the preceding Clauses, further comprising a coil disposed around the elongated member in a region proximal to the distal element.

240. The system of Clause 219, wherein the coil is electrically conductive.

241. The system of Clause 194, wherein:
the electrode comprises a hypotube coupled to the second electrical terminal, the hypotube having a proximal portion, a distal portion, and a lumen extending therethrough;
the elongated member extends through the hypotube lumen;
an insulating material is disposed between the hypotube and the elongated member, the insulating material extending from the proximal portion of the hypotube to the distal portion of the hypotube; and
the distal element is in electrical communication with the elongated member.

242. The system of Clause 221, further comprising a second insulating material disposed around an outer surface of a proximal portion of the hypotube.

243. The system of Clause 222, wherein the outer surface of a distal portion of the hypotube is uncovered by the second insulating material.

244. The system of any one of Clauses 221 to 223, wherein the insulating material comprises PTFE, polyimide, ETFE, or a dielectric polymer.

245. The system of any one of Clauses 221 to 224, wherein the elongated member is fixed with respect to the hypotube.

246. The system of any one of Clauses 221 to 225, wherein, when the distal element is in the presence of an electrolytic medium and voltage is supplied to the first and second electrical terminals of the extracorporeal power supply, current flows from the distal element to the hypotube.

247. The system of any one of the preceding Clauses, wherein the electrode is disposed at the distal portion of the catheter.

248. The system of Clause 227, wherein the electrode is in electrical communication with a conductive lead extending proximally along the catheter.

249. The system of any one of the preceding Clauses, wherein the electrode comprises a conductive band extending at least partially circumferentially around the distal portion of the catheter.

250. The system of Clause 229, wherein the conductive band is disposed on an inner surface of the catheter.

251. The system of Clause 229, wherein the conductive band is disposed on an outer surface of the catheter.

252. The system of any one of the preceding Clauses, wherein the electrode comprises an interventional element coupled to the distal portion of the elongated member and configured to be slidably advanced through the catheter lumen, the interventional element being electrically isolated from the distal element.

253. The system of Clause 232, wherein the interventional element comprises the interventional element of any of the preceding Clauses.

254. The system of Clause 232 or 233, wherein at least a portion of the interventional element is coated with a conductive material.

255. The system of Clause 232, wherein at least a portion of the interventional element is coated with an insulative material.

256. The system of any one of the preceding Clauses, wherein the catheter comprises an aspiration catheter.

257. The system of any one of the preceding Clauses, further comprising a suction source configured to supply negative pressure through the catheter to aspirate a region adjacent to the distal portion of the catheter.

258. The system of any one of the preceding Clauses, further comprising the power supply, wherein the first terminal is positive, and the second terminal is negative.

259. The system of any one of the preceding Clauses, wherein, when the distal element is in the presence of an electrolytic medium and voltage is supplied to the first and second electrical terminals, current flows from the distal element to the electrode.

260. The system of any one of the preceding Clauses, wherein the electrode comprises an external needle or grounding pad.

261. The system of any one of the preceding Clauses, wherein the electrode comprises a distal portion of the distal element electrically isolated from an attachment portion of the distal element.

262. The system of Clause 241, wherein the distal element comprises a plurality of individual conductive filaments, and wherein a first subset of filaments is in electrical communication with the first terminal and a second subset of filaments is in electrical communication with the second terminal, the first and second subsets of filaments being electrically isolated from one another along their respective lengths.

263. The system of Clause 241 or 242, wherein, when the distal element is in the presence of an electrolytic medium and voltage is supplied to the first and second electrical terminals, current flows from the first subset of filaments to the second subset of filaments through the electrolytic medium.

264. A thrombectomy system, comprising:
a current generator;
a pushwire electrically coupled to the current generator, the pushwire configured to be slidably advanced through a blood vessel to a deployment site adjacent a thrombus; and
a distal element coupled to a distal portion of a pushwire such that the distal element is in electrical communication with the current generator.

265. The system of Clause 244, wherein the distal element comprises the distal element of any one of the preceding Clauses.

266. The system of any one of the preceding Clauses, wherein the distal element comprises an attachment portion configured to electrostatically engage with the thrombus.

267. The system of Clause 246, wherein the attachment portion comprises a proximal face of the distal element.

268. The system of Clause 246, wherein at least part of the attachment portion extends along the elongated member.

269. The system of Clause 248, wherein at least part of the attachment portion extends along the elongated member proximal of the distal element.

270. The system of any one of Clauses 246 to 249, wherein the attachment portion is configured to function as an electrode surface.

271. The system of any one of Clauses 246 to 250, wherein the attachment portion is configured to define a conductivity gradient as it extends along a proximal-to-distal direction.

272. The system of any one of Clauses 246 to 251, wherein the attachment portion is configured to define a charge density gradient as it extends along a proximal-to-distal direction.

273. The system of any one of Clauses 246 to 252, further comprising a return electrode in electrical communication with the current generator.

274. The system of any one of Clauses 246 to 253, wherein a proximal portion of the distal element comprises the attachment portion and wherein a distal end portion of the distal element comprises a non-attachment portion.

275. The system of Clause any one of Clauses 246 to 254, wherein the attachment portion is more conductive than other portions of the distal element.

276. The system of any one of Clauses 246 to 255, wherein the attachment portion is at least partially coated with a conductive material.

277. The system of Clause 256, wherein the conductive material comprises gold.

278. The system of Clause 256, wherein the coating has a varying thickness or concentration over the attachment portion.

279. The system of any one of Clauses 246 to 258, wherein non-attachment portions of the distal element are coated with an insulating material.

280. The system of one of the preceding Clauses, wherein the pushwire comprises a coil proximal to the distal element.

281. The system of one of the preceding Clauses, further comprising a coil disposed around the pushwire in a region proximal to the distal element.

282. The system of Clause 261, wherein the coil is electrically conductive.

283. The system of one of the preceding Clauses, further comprising a return electrode in electrical communication with the current generator.

284. The system of Clause 263, wherein:
the return electrode comprises a hypotube coupled to the second electrical terminal, the hypotube having a proximal portion, a distal portion, and a lumen extending therethrough;
the pushwire extends through the hypotube lumen;
an insulating material is disposed between the hypotube and the pushwire, the insulating material extending from the proximal portion of the hypotube to the distal portion of the hypotube; and
the distal element is in electrical communication with the pushwire.

285. The system of one of the preceding Clauses, further comprising a second insulating material disposed around an outer surface of a proximal portion of the hypotube.

286. The system of Clause 265, wherein the outer surface of a distal portion of the hypotube is uncovered by the second insulating material.

287. The system of one of the preceding Clauses, wherein the insulating material comprises PTFE, polyimide, ETFE, or a dielectric polymer.

288. The system of one of the preceding Clauses, wherein the pushwire is fixed with respect to the hypotube.

289. The system of one of the preceding Clauses, wherein, when the distal element is in the presence of an electrolytic medium and current is supplied via the current generator, current flows from the distal element to the hypotube.

290. The system of Clause 263, wherein the return electrode is disposed at the distal portion of the catheter.

291. The system of Clause 270, wherein the return electrode is in electrical communication with a conductive lead extending proximally along the catheter.

292. The system of Clause 270 or 271, wherein the return electrode comprises a conductive band extending at least partially circumferentially around the distal portion of the catheter.

293. The system of Clause 272, wherein the conductive band is disposed on at least one of an inner surface or an outer surface of the catheter.

294. The system of any one of Clauses 263 to 273, wherein, when the distal element is in the presence of an electrolytic medium and current is supplied via the current generator, current flows from the distal element to the return electrode.

295. The system of Clauses 263, wherein the return electrode comprises an external needle or grounding pad.

296. The system of Clause 263, wherein the return electrode comprises a distal portion of the distal element electrically isolated from an attachment portion of the distal element.

297. The system of Clause 276, wherein the distal element comprises a plurality of individual conductive filaments, and wherein a first subset of filaments is in electrical communication with the first terminal and a second subset of filaments is in electrical communication with the second terminal, the first and second subsets of filaments being electrically isolated from one another along their respective lengths.

298. The system of Clause 276 or 277, wherein, when the distal element is in the presence of an electrolytic medium and voltage is supplied to the first and second electrical terminals, current flows from the first subset of filaments to the second subset of filaments through the electrolytic medium.

299. A thrombectomy device, comprising:
an elongated member configured to be slidably advanced through a corporeal lumen, the elongated member configured to be electrically coupled to a first electrical terminal of a current generator;
a delivery electrode comprising a distal element coupled to a distal portion of the elongated member; and
a return electrode configured to be electrically coupled to a second electrical terminal of the current generator.

300. The device of Clause 279, further comprising a current generator having a first electrical terminal coupled to the elongated member and a second electrical terminal coupled to the return electrode.

301. The device of one of the preceding Clauses, wherein the distal element comprises the distal element of any one of the preceding Clauses.

302. The device of one of the preceding Clauses, wherein the distal element comprises an attachment portion configured to electrostatically engage with a thrombus.

303. The device of Clause 282, wherein at least part of the attachment portion extends along the elongated member.

304. The device of Clause 283, wherein at least part of the attachment portion extends along the elongated member proximal of the distal element.

305. The device of any one of Clauses 282 to 284, wherein the attachment portion is configured to function as an electrode surface for the delivery electrode.

306. The device of any one of Clauses 282 to 285, wherein the attachment portion is configured to define a conductivity gradient as it extends along a proximal-to-distal direction.

307. The device of any one of Clauses 282 to 286, wherein the attachment portion is configured to define a charge density gradient as it extends along a proximal-to-distal direction.

308. The device of any one of the preceding Clauses, further comprising a first catheter configured to slidably receive the elongated member therethrough.

309. The device of Clause 288, further comprising a suction source configured to supply negative pressure through the catheter to aspirate a region adjacent to the distal portion of the catheter.

310. The device of any one of Clauses 282 to 290, wherein the attachment portion further comprises a coil coupled to the elongated member in a region proximal to the distal element.

311. The device of any one of Clauses 282 to 291, wherein the attachment portion comprises a proximal face of the distal element.

312. The device of any one of Clauses 282 to 292, wherein a proximal portion of the distal element comprises the attachment portion and wherein a distal end portion of the distal element comprises a non-attachment portion.

313. The device of Clause 292, wherein non-attachment portions are coated with an insulating material.

314. The device of any one of Clauses 282 to 293, wherein the attachment portion is more conductive than other portions of the distal element.

315. The device of any one of Clauses 282 to 295, wherein the attachment portion is at least partially coated with a conductive material.

316. The device of Clause 295, wherein the conductive material comprises gold.

317. The device of Clause 295, wherein the conductive material has a varying thickness or concentration over the attachment portion.

318. The device of any one of the preceding Clauses, wherein the elongated member comprises a coil proximal to the distal element.

319. The device of any one of the preceding Clauses, further comprising a coil disposed around the elongated member in a region proximal to the distal element.

320. The device of Clause 299, wherein the coil is conductive.

321. A method, comprising:
advancing an elongated member through a catheter to a treatment site adjacent a thrombus in a blood vessel, the elongated member having a distal element coupled to a distal portion of the elongated member;
positioning the distal element at least partially distal to the thrombus, the distal element expanded into apposition with the vessel wall; and supplying electrical current to the distal element via the elongated member.

322. The method of Clause 301, further comprising ceasing the supplying of electrical current to the second electrical terminal after a first time period.

323. The method of Clause 302, further comprising, after ceasing the supplying of electrical current, proximally retracting the elongated member with respect to the catheter.

324. The method of Clause 302, wherein the first time period is less than about 5 minutes.

325. The method of Clause 302, wherein the first time period is less than about 2 minutes.

326. The method of any one of the preceding Clauses, wherein the total energy delivered via the electrical current is between 0.75-24,000 mJ, or 120-24,000 mJ, and wherein the peak current delivered via the electrical current is between 0.5-5 mA.

327. The method of any one of the preceding Clauses, wherein the total energy delivered via the electrical current is between 120-5000 mJ.

328. The method of any one of the preceding Clauses, wherein the total charge delivered via the electrical current is between 30-1200 mC.

329. The method of any one of the preceding Clauses, wherein the total charge delivered via the electrical current is between 120-160 mC.

330. The method of any one of the preceding Clauses, wherein the frequency of the electrical current is between 1 Hz and 1 MHz.

331. The method of any one of the preceding Clauses, wherein the frequency of the electrical current is between 1 Hz and 1 kHz.

332. The method of any one of the preceding Clauses, wherein the duty cycle of the electrical current is between 5-99%.

333. The method of any one of the preceding Clauses, wherein the duty cycle of the electrical current is between 5-20%.

334. The method of any one of the preceding Clauses, wherein a peak current delivered via the electrical current is between 0.5-5 mA.

335. The method of any one of the preceding Clauses, wherein delivering the electrical current to the distal element is not substantially thrombogenic.

336. The method of any one of the preceding Clauses, wherein the electrical current comprises a non-square waveform.

337. The method of any one of the preceding Clauses, wherein the electrical current comprises a composite waveform including the superposition of a square waveform and a non-square waveform.

338. The method of Clause 317, wherein the non-square waveform comprises a triangular waveform.

339. The method of any one of the preceding Clauses, wherein the distal element comprises an electrically conductive self-expandable device.

340. The method of any one of the preceding Clauses, wherein the distal element comprises a plurality of braided filaments.

341. The method of any one of the preceding Clauses, wherein the distal element comprises an attachment portion configured to engage with the thrombus.

342. The method of Clause 321, wherein the attachment portion is more conductive than other portions of the distal element.

343. The method of Clause 321, wherein the attachment portion is at least partially coated with a conductive material.

344. The method of Clause 323, wherein the conductive material comprises gold.

345. The method of any one of the preceding Clauses, further comprising removing the thrombus from the blood vessel.

346. The method of any one of the preceding Clauses, further comprising retracting the distal element, thereby displacing the thrombus.

347. A thrombectomy system, comprising:
- a catheter having a lumen and a distal portion configured to be positioned adjacent to a thrombus in a blood vessel;
- an interventional element coupled to a distal portion of an elongated member, the elongated member configured to be electrically coupled to a first terminal of an extracorporeal power supply and to be slidably advanced through the catheter lumen; and
- a distal element configured to be disposed distal to the interventional element and electrically coupled to a second terminal of the extracorporeal power supply.

348. The system of Clause 327, wherein the distal element is coupled to the distal portion of the elongated member at a position distal to the interventional element.

349. The system of Clause 328, wherein the elongated member comprises a first conductive path coupled to the interventional element and a second conductive path coupled to the distal element, the first and second conductive paths electrically insulated from one another along their respective lengths.

350. The system of Clause 329, wherein the first conductive path is configured to be electrically coupled to the first terminal of an extracorporeal power supply and the second conductive path is configured to be electrically coupled to the second terminal of the extracorporeal power supply.

351. The system of any one of the preceding Clauses, wherein the first conductive path comprises a conductive tube having a lumen, and the second conductive path comprises a pushwire extending through the conductive tube lumen, wherein an insulating material is disposed between the conductive tube and the pushwire.

352. The system of Clause 331, further comprising a second insulating material disposed around an outer surface of a proximal portion of the hypotube.

353. The system of Clause 331 or Clause 332, wherein the insulating material comprises PTFE, polyimide, ETFE, or a dielectric polymer.

354. The system of any one of Clauses 331 to 333, wherein the pushwire is fixed with respect to the conductive tube.

355. The system of any one of the preceding Clauses, wherein the distal element is coupled to a distal portion of a second elongated member configured to be slidably advanced through the catheter lumen.

356. The system of any one of the preceding Clauses, wherein the distal element comprises the distal element of any one of the preceding Clauses.

357. The system of any one of the preceding Clauses, wherein the interventional element comprises the interventional element of any one of the preceding Clauses.

358. The system of any one of the preceding Clauses, wherein at least a portion of the interventional element is coated with a conductive material.

359. The system of any one of the preceding Clauses, wherein at least a portion of the interventional element is coated with an insulative material.

360. The system of any one of the preceding Clauses, wherein at least a portion of the distal element is coated with a conductive material.

361. The system of any one of the preceding Clauses, wherein at least a portion of the distal element is coated with an insulative material.

362. The system of any one of the preceding Clauses, wherein, when the interventional element and the distal element are in the presence of electrolytic medium and power is supplied the first and second terminals of the extracorporeal power supply, current flows from the interventional element to the distal element.

363. The system of any one of the preceding Clauses, further comprising the power supply, wherein the first terminal is positive and wherein the second terminal is negative.

364. The system of any one of the preceding Clauses, wherein the catheter comprises an aspiration catheter.

365. The system of any one of the preceding Clauses, further comprising a suction source configured to supply negative pressure through the catheter to aspirate a region adjacent to the distal portion of the catheter.

366. A thrombectomy device, comprising:
an elongated member configured to be slidably advanced through a corporeal lumen, the elongated member having a distal portion configured to be positioned adjacent a thrombus;
a first conductive path extending along the elongated member and configured to be electrically coupled to an extracorporeal current generator;
a second conductive path extending along the elongated member and configured to be electrically coupled to the extracorporeal current generator, the second conductive path electrically isolated from the first conductive path along its length;
an interventional element coupled to the distal portion of the elongated member such that the interventional element is in electrical communication with the first conductive path;
a distal element coupled to the distal portion of the elongated member at a position distal to the interventional element such that the distal element is in electrical communication with the second conductive path.

367. The device of any one of the preceding Clauses, wherein the second conductive path comprises a conductive tube having a lumen, and the first conductive path comprises a pushwire extending through the conductive tube lumen, wherein an insulating material is disposed between the conductive tube and the pushwire.

368. The device of any one of the preceding Clauses, further comprising a second insulating material disposed around an outer surface of a proximal portion of the conductive tube.

369. The device of any one of the preceding Clauses, wherein the insulating material comprises PTFE, polyimide, ETFE, or a dielectric polymer.

370. The device of any one of the preceding Clauses, wherein the elongated member is fixed with respect to the conductive tube.

371. The device of any one of the preceding Clauses, wherein the distal element comprises the distal element of any one of the preceding Clauses.

372. The device of any one of the preceding Clauses, wherein the interventional comprises the interventional element of any one of the preceding Clauses.

373. The device of any one of the preceding Clauses, wherein, when the interventional element and the distal element are in the presence of electrolytic medium and current is supplied via the extracorporeal current generator, current flows from the interventional element to the distal element.

374. The device of any one of the preceding Clauses, further comprising the current generator, wherein the first terminal is positive and wherein the second terminal is negative.

375. A method, comprising:
advancing an elongated member through a catheter to a treatment site adjacent a thrombus in a blood vessel, the elongated member having a distal element coupled to a distal portion of the elongated member;
positioning an interventional element at or adjacent to the thrombus, the interventional element in electrical communication with a first electrical terminal of an extracorporeal current generator;
positioning the distal element at least partially distal to the thrombus, the distal element expanded into apposition with the vessel wall; and
supplying electrical current to the interventional element via the current generator.

376. The method of any one of the preceding Clauses, further comprising ceasing the supplying of electrical current after a first time period.

377. The method of any one of the preceding Clauses, further comprising, after ceasing the supplying of electrical current, proximally retracting the elongated member with respect to the catheter.

378. The method of any one of the preceding Clauses, wherein the first time period is less than about 5 minutes.

379. The method of any one of the preceding Clauses, wherein the first time period is less than about 2 minutes.

380. The method of any one of the preceding Clauses, wherein supplying electrical current comprises the steps of any one of the preceding Clauses.

381. The method of any one of the preceding Clauses, wherein the distal element is in electrical communication with a second electrical terminal of the extracorporeal current generator.

382. The method of any one of the preceding Clauses, wherein the first electrical terminal is positive, and the second electrical terminal is negative.

383. The method of any one of the preceding Clauses, wherein the distal element comprises the distal element of any one of the preceding Clauses.

384. The method of any one of the preceding Clauses, wherein the interventional element comprises the interventional element of any one of the preceding Clauses.

385. A thrombectomy system, comprising:
a catheter having a lumen and a distal portion configured to be positioned adjacent to a thrombus in a blood vessel;
an elongated member configured to be electrically coupled to a first terminal of a power supply and to be slidably advanced through the catheter lumen;
a distal element coupled to a distal portion of the elongated member, the distal element comprising an attachment portion configured to electrostatically engage with the thrombus; and
an electrode configured to be electrically coupled to a second terminal of the power supply.

386. The system of Clause 385, wherein at least part of the attachment portion extends along the elongated member.

387. The system of Clause 385, wherein at least part of the attachment portion extends along the elongated member proximal of the distal element.

388. The system of Clause 385, wherein the attachment portion is configured to function as an electrode surface.

389. The system of Clause 385, wherein the attachment portion defines a conductivity gradient as the attachment portion extends along a proximal-to-distal direction.

390. The system of Clause 389, wherein the conductivity gradient comprises an increase in conductivity as the attachment portion extends distally.

391. The system of Clause 389, wherein the conductivity gradient comprises a decrease in conductivity as the attachment portion extends distally.

392. The system of Clause 385, wherein the attachment portion is configured to define a charge density gradient as the attachment portion extends along a proximal-to-distal direction.

393. The system of Clause 392, wherein the charge density gradient comprises an increase in charge density as attachment portion extends distally.

394. The system of Clause 392, wherein the charge density gradient comprises a decrease in charge density as attachment portion extends distally.

395. The system of Clause 385, wherein the attachment portion is at least partially coated with a conductive material.

396. The system of Clause 395, wherein the conductive material has a varying thickness or concentration over the attachment portion.

397. The system of Clause 385, wherein the attachment portion comprises a coil proximal to the distal element.

398. A thrombectomy system, comprising:
a current generator;
an elongated member electrically coupled to the current generator, the elongated member configured to be slidably advanced through a blood vessel to a deployment site adjacent a thrombus; and
a distal element coupled to a distal portion of the elongated member such that the distal element is in electrical communication with the current generator, the distal element comprising an attachment portion configured to electrostatically engage with the thrombus.

399. The system of Clause 398, wherein at least part of the attachment portion extends along the elongated member.

400. The system of Clause 398, wherein at least part of the attachment portion extends along the elongated member proximal of the distal element.

401. The system of Clause 398, wherein the attachment portion is configured to function as an electrode surface.

402. The system of Clause 398, wherein the attachment portion is configured to define a conductivity gradient as the attachment portion extends along a proximal-to-distal direction.

403. The system of Clause 398, wherein the attachment portion is configured to define a charge density gradient as the attachment portion extends along a proximal-to-distal direction.

404. The system of Clause 398, further comprising a return electrode in electrical communication with the current generator.

405. The system of Clause 404, wherein:
the return electrode comprises a conductive tube electrically coupled to the current generator, the conductive tube having a proximal portion, a distal portion, and a lumen extending therethrough;
the elongated member extends through the conductive tube lumen;
an insulating material is disposed between the conductive tube and the elongated member, the insulating material extending from the proximal portion of the conductive tube to the distal portion of the conductive tube; and
the distal element is in electrical communication with the elongated member.

406. A thrombectomy device, comprising:
an elongated member configured to be slidably advanced through a corporeal lumen, the elongated member configured to be electrically coupled to a first electrical terminal of a current generator;
a delivery electrode comprising a distal element coupled to a distal portion of the elongated member, wherein the distal element comprises an attachment portion configured to electrostatically engage with a thrombus; and
a return electrode configured to be electrically coupled to a second electrical terminal of the current generator.

407. The device of Clause 406, wherein at least part of the attachment portion extends along the elongated member.

408. The device of Clause 406, wherein at least part of the attachment portion extends along the elongated member proximal of the distal element.

409. The device of Clause 406, wherein the attachment portion is configured to function as an electrode surface for the delivery electrode.

410. The device of Clause 406, wherein the attachment portion is configured to define a conductivity gradient as the attachment portion extends along a proximal-to-distal direction.

411. The device of Clause 406, wherein the attachment portion is configured to define a charge density gradient as the attachment portion extends along a proximal-to-distal direction.

412. The device of Clause 406, further comprising a catheter configured to slidably receive the elongated member therethrough.

413. The device of Clause 412, further comprising a suction source configured to supply negative pressure through the catheter to aspirate a region adjacent to a distal portion of the catheter.

414. The device of Clause 406, wherein the attachment portion further comprises a coil coupled to the elongated member in a region proximal to the distal element.

415. A thrombectomy system, comprising:
a catheter having a lumen and a distal portion configured to be positioned adjacent to a thrombus in a blood vessel;
an interventional element coupled to a distal portion of an elongated member, the elongated member configured to be slidably advanced through the catheter lumen and to be electrically coupled to a first terminal of an extracorporeal power supply via a first conductive path; and
a distal element positioned distal to the interventional element and electrically coupled to a second terminal of the extracorporeal power supply via a second conductive path.

416. The system of Clause 415, wherein the first conductive path comprises a conductive tube having a lumen, the elongated member comprises the second conductive path extending through the conductive tube lumen, and an insulating material is disposed between the conductive tube and the elongated member.

417. The system of Clause 415, wherein the distal element is coupled to the distal portion of the elongated member at a position proximal of the interventional element.

418. The system of Clause 415, wherein the elongated element is a first elongated member, and wherein the distal element is coupled to a distal portion of a second elongated member configured to be slidably advanced through the catheter lumen.

419. The system of Clause 415, wherein the distal element comprises an expandable mesh having a low-profile state for delivery to a deployment site and an expanded state in which at least a portion of the mesh is configured to be in apposition with the blood vessel wall at the deployment site.

420. The system of Clause 415, wherein the distal element comprises a plurality of braided filaments.

421. The system of Clause 415, wherein the distal element comprises a braid ball.

422. The system of Clause 415, wherein the distal element is configured to be deployed distal to the thrombus to protect against distal embolization.

423. The system of Clause 415, wherein the interventional element comprises a thrombectomy device.

424. The system of Clause 415, wherein the interventional element comprises a stent retriever.

425. The system of Clause 415, wherein, when the interventional element and the distal element are in the presence of electrolytic medium and power is supplied to the first and second terminals of the extracorporeal power supply, current flows from the interventional element to the distal element.

426. The system of Clause 415, further comprising the extracorporeal power supply, wherein the first terminal is positive and the second terminal is negative.

427. The system of Clause 415, further comprising a suction source configured to supply negative pressure through the catheter to aspirate a region adjacent to the distal portion of the catheter.

428. A thrombectomy device, comprising:
an elongated member configured to be slidably advanced through a corporeal lumen, the elongated member having a distal portion configured to be positioned adjacent a thrombus;
a first conductive path extending along the elongated member and configured to be electrically coupled to an extracorporeal current generator;
a second conductive path extending along the elongated member and configured to be electrically coupled to the extracorporeal current generator, the second conductive path electrically isolated from the first conductive path;
an interventional element coupled to the distal portion of the elongated member such that the interventional element is in electrical communication with the first conductive path; and
a distal element coupled to the distal portion of the elongated member at a position distal to the interventional element such that the distal element is in electrical communication with the second conductive path,
wherein, when the interventional element and the distal element are in the presence of electrolytic medium and current is supplied via the extracorporeal current generator, current flows from the interventional element to the distal element.

429. The device of Clause 428, wherein the first conductive path comprises a conductive tube having a lumen, and the second conductive path extends through the conductive tube lumen, wherein an insulating material is disposed between the conductive tube and the elongated member.

430. The device of Clause 428, wherein the distal element comprises an expandable mesh having a low-profile state for delivery to a deployment site and an expanded state in which at least a portion of the mesh is configured to be in apposition with a blood vessel wall at the deployment site.

431. The device of Clause 428, wherein the distal element comprises a plurality of braided filaments.

432. The device of Clause 428, wherein the distal element comprises a braid ball.

433. The device of Clause 428, wherein the interventional element comprises a stent retriever.

434. The device of Clause 428, wherein the interventional element comprises a removal device.

435. The device of Clause 428, wherein the interventional element is a laser-cut stent.

436. The device of Clause 428, wherein at least a portion of the distal element is coated with a conductive material.

437. The device of Clause 428, further comprising the extracorporeal current generator, wherein a positive terminal of the extracorporeal current generator is coupled to the first conductive path and a negative terminal of the extracorporeal current generator is coupled to the second conductive path.

Additional features and advantages of the present technology are described below, and in part will be apparent from the description, or may be learned by practice of the present technology. The advantages of the present technology will be realized and attained by the structure particularly pointed out in the written description and claims hereof as well as the appended drawings.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

FIG. 2A shows a schematic side view of a portion of the treatment system shown in FIG. 1.

FIG. 2B shows a cross-sectional view of the treatment device taken along line 2B-2B in FIG. 2A.

FIG. 2C shows a cross-sectional view of another embodiment of the treatment device.

FIG. 3 illustrates a side view of a treatment device in accordance with aspects of the present technology.

FIG. 4 illustrates a side view of a treatment device in accordance with aspects of the present technology.

FIG. 5A illustrates a side view of a treatment device in accordance with aspects of the present technology.

FIG. 5B illustrates a side view of a treatment device in accordance with aspects of the present technology.

FIG. 6 illustrates a side view of a treatment device in accordance with aspects of the present technology.

FIG. 7 illustrates a side view of a treatment device in accordance with aspects of the present technology.

FIG. 12 illustrates schematic side views of treatment systems in accordance with embodiments of the present technology.

FIG. 13 illustrates a schematic side view of a treatment system in accordance with embodiments of the present technology.

FIG. 14 illustrates a schematic side view of a treatment system in accordance with embodiments of the present technology.

FIG. 15 illustrates a schematic side view of a treatment system in accordance with embodiments of the present technology.

FIG. 16 illustrates a schematic side view of a treatment system in accordance with embodiments of the present technology.

FIG. 17 illustrates a schematic side view of a treatment system in accordance with embodiments of the present technology.

FIG. 18B illustrates a method of removing clot material from a blood vessel lumen, in accordance with one or more embodiments of the present technology.

FIG. 18C illustrates a method of removing clot material from a blood vessel lumen, in accordance with one or more embodiments of the present technology.

FIG. 18D illustrates a method of removing clot material from a blood vessel lumen, in accordance with one or more embodiments of the present technology.

FIG. 21 shows a perspective view of an electrically enhanced treatment system for retrieving material from a body lumen, in accordance with one or more embodiments of the present technology.

DETAILED DESCRIPTION

The present technology provides devices, systems, and methods for removing clot and/or other material from a blood vessel lumen. Although many of the embodiments are described below with respect to devices, systems, and methods for treating a cerebral or intracranial embolism, other applications and other embodiments in addition to those described herein are within the scope of the technology. For example, the treatment systems and methods of the present technology may be used to remove emboli from body lumens other than blood vessels (e.g., the digestive tract, etc.) and/or may be used to remove emboli from blood vessels outside of the brain (e.g., pulmonary, abdominal, cervical, or thoracic blood vessels, or peripheral blood vessels including those within the legs or arms, etc.). In addition, the treatment systems and methods of the present technology may be used to remove luminal obstructions other than clot material (e.g., plaque, resected tissue, foreign material, etc.).

I. Overview of Treatment Systems of the Present Technology

Figure 1:
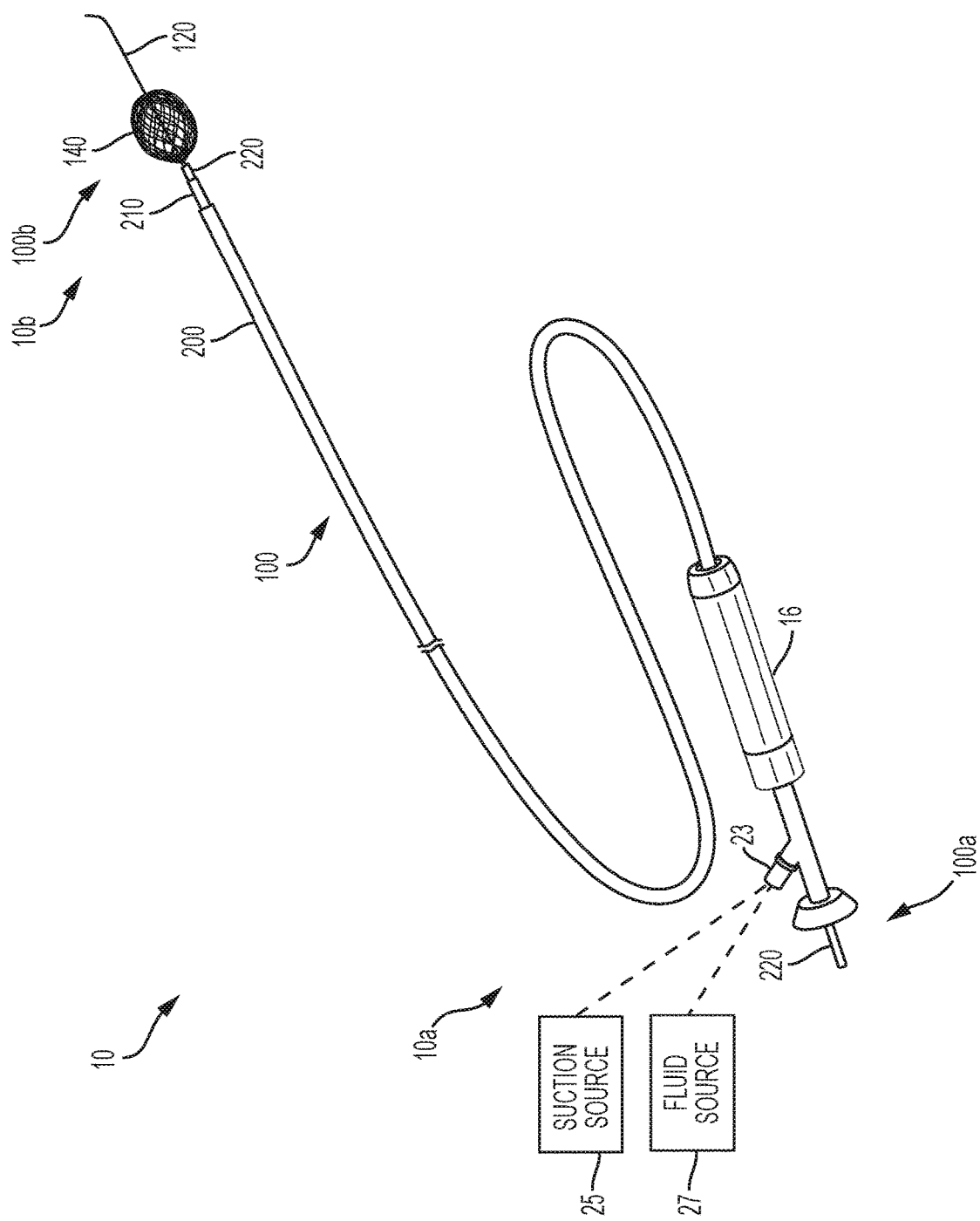
FIG. 1 shows a perspective view of a treatment system for retrieving material from a body lumen, in accordance with one or more embodiments of the present technology.

FIG. 1 illustrates a view of a treatment system 10 according to one or more embodiments of the present technology. As shown in FIG. 1, the treatment system 10 has a proximal portion 10a configured to be extracorporeally positioned during treatment and a distal portion 10b configured to be intravascularly positioned within a blood vessel (such as an intracranial blood vessel) at a treatment site at or proximate a thrombus. The treatment system 10 may include a handle 16 at the proximal portion 10a, and a treatment device 100 and a plurality of elongated shafts or members extending between the proximal and distal portions 10a and 10b. For example, in some embodiments, such as that shown in FIG. 1, the treatment system 10 may include one, some, or all of: a first catheter 200 (such as a guide catheter or balloon guide catheter), a second catheter 210 (such as a distal access catheter or aspiration catheter) configured to be slidably disposed within a lumen of the first catheter 200, and a third catheter 220 (such as a microcatheter) configured to be slidably disposed within a lumen of the second catheter 210. In some embodiments, the first catheter 200 is coupled to the handle 16, which provides proximal access to the second catheter 210, the third catheter 220, and/or the treatment device 100. The treatment device 100 may be configured to be slidably disposed within a lumen of the first catheter 200, the second catheter 210, and/or the third catheter 220.

As shown in FIG. 1, the treatment device 100 has a proximal portion 100a, a distal portion 100b, an elongated member 120 extending from the proximal portion 100a to the distal portion 100b, and an expandable distal element 140 coupled to a distal portion of the elongated member 120. The distal element 140 may comprise an expandable mesh having a low-profile or constrained state while positioned within a catheter for delivery to a deployment location and an expanded state in which at least a portion of the mesh is configured to be in apposition with the blood vessel wall. The distal element 140 is configured to expand into contact with the blood vessel wall at desired locations along the intravascular path to the treatment site as well as at the treatment site to anchor and/or stabilize the elongated member 120 and/or any portion of the treatment device 100 and/or treatment system 10 at the desired location. As detailed below, the distal element 140 may also be configured to facilitate removal of the thrombus from the treatment site.

In some embodiments, the treatment system 10 includes a suction source 25 (e.g., a syringe, a pump, etc.) configured to be fluidly coupled (e.g., via a connector 23) to a proximal portion of one or more of the first catheter 200, the second catheter 210, and/or the third catheter 220 to apply negative pressure therethrough. In some embodiments, the treatment system 10 includes a fluid source 27 (e.g., a fluid reservoir, a syringe, pump, etc.) configured to be fluidly coupled (e.g., via the connector 23) to a proximal portion of one or more of the first catheter 200, the second catheter 210, and/or the third catheter 220 to supply fluid (e.g., saline, contrast agents, a drug such as a thrombolytic agent, etc.) to the treatment site.

According to some embodiments, for example as shown in FIG. 1, each of the first, second, and third catheters 200, 210, and 220 can be formed as a generally tubular member extending along and about a central axis and terminating in a respective distal end. The first catheter 200 can be sized and configured to slidably receive both the second catheter 210 and the third catheter 220 therethrough. In some embodiments, the first catheter 200 is a balloon-guide catheter having an inflatable balloon or other expandable member that can be used to anchor the first catheter 200 with respect to a surrounding vessel, and/or arrest the flow of blood at the location of the balloon.

The second catheter 210 can be sized and configured to slidably receive the third catheter 220 therethrough. The second catheter 210 can be coupled at a proximal portion to a suction source 25 such as a pump or syringe in order to supply negative pressure to a treatment site. In some embodiments, the second catheter 210 may have a working length of about 100 cm to about 140 cm, for example about 105 cm, about 120 cm, or about 132 cm. The second catheter 210 may have an inner diameter of about 0.068 inches (0.172 cm), or about 0.071 inches (0.180 cm).

According to some embodiments, the third catheter 220 is generally constructed to track over a conventional guidewire in the cervical anatomy and into the cerebral vessels associated with the brain and may also be chosen according to several standard designs that are generally available. Accordingly, the third catheter 220 can have a length that is at least 125 cm long, and more particularly may be between about 125 cm and about 175 cm long. In some embodiments, the third catheter 220 may have an inner diameter of about 0.015 inches (0.0381 cm), 0.017 inches (0.043 cm), about 0.021 inches (0.053 cm), or about 0.027 inches (0.069 cm). Other designs and dimensions are contemplated.

As described in more detail below with respect to FIGS. 10A-10E, in operation the first catheter 200 can first be advanced through a vessel and a balloon can be expanded to anchor the first catheter 200 in place and/or arrest blood flow from areas proximal of the balloon. Next, the second catheter 210 can be advanced through the first catheter 200 until its distal end extends distally beyond the distal end of the first catheter 200. The second catheter 210 can be positioned such that its distal end is close to or adjacent a treatment site (e.g., a site of a blood clot within the vessel). The third catheter 220 may then be advanced through the second catheter 210 until its distal end extends distally beyond the distal end of the second catheter 210.

According to some embodiments, the bodies of the catheters 200, 210, and 220 can be made from various thermoplastics, e.g., polytetrafluoroethylene (PTFE or TEFLON®), fluorinated ethylene propylene (FEP), high-density polyethylene (HDPE), polyether ether ketone (PEEK), etc., which can optionally be lined on the inner surface of the catheters or an adjacent surface with a hydrophilic material such as polyvinylpyrrolidone (PVP) or some other plastic coating. Additionally, either surface can be coated with various combinations of different materials, depending upon the desired results. Any one or more of the catheters 200, 210, 220 may incorporate a reinforcement structure in its construction, e.g. layered between an inner lubricious liner and an outer polymeric jacket. Such a reinforcement structure can be metallic and/or polymeric, and comprise a tubular braid, a coil, a hypotube (e.g. a spiral-cut or slotted-cut hypotube), or combinations of the foregoing. Suitable metals for constructing the reinforcement structure include without limitation stainless steel, nitinol, and cobalt-chromium.

II. Example Treatment Devices and Methods of Use

FIG. 2A is a side schematic view of some embodiments of the treatment device 100 shown in FIG. 1. As shown in FIG. 2A, the treatment device 100 may comprise an elongated member 120 (such as a wire or guidewire) and an expandable distal element 140 coupled to a distal portion of the elongated member 120 via a connection assembly 130. In the embodiment shown in FIG. 2A, the elongated member 120 extends distally from the connection assembly 130 through the entire length of the distal element 140 and projects distally beyond the distal element 140. In some embodiments, the elongated member 120 may terminate at the connection assembly 130 and does not extend into the interior cavity and/or is not coextensive with any portion of the distal element 140. In some embodiments, the elongated member 120 terminates at a location along the length of the distal element 140 but does not extend distally beyond the distal element 140.

The elongated member 120 can be movable within the catheter and/or microcatheter to position the distal element 140 at a desired location. The elongated member 120 can be sufficiently flexible to allow manipulation, e.g., advancement and/or retraction, of the treatment device 100 through tortuous passages. Tortuous passages can include, for example, catheter lumens, microcatheter lumens, blood vessels, urinary tracts, biliary tracts, and airways. The elongated member 120 can be formed of any material and in any dimensions suitable for the task(s) for which the system is to be employed. In some embodiments, the elongated member 120 can comprise a solid metal wire. In some embodiments, the elongated member 120 may comprise any other suitable form of shaft such as an elongated tubular shaft, as discussed below with reference to FIG. 7.

In some embodiments, the elongated member 120 can comprise stainless steel, nitinol, or other metal or alloy. In some embodiments, the elongated member 120 can be surrounded over some or all of its length by a coating, such as, for example, polytetrafluoroethylene. A distal portion or tip 120b of the elongated member 120 can have a curved shape, for example as illustrated in FIG. 2A, such that the distal portion 120b of the elongated member 120 can be used to guide advancement of the distal end of the elongated member 120. The elongated member 120 may have a diameter that is generally constant along its length, or the elongated member 120 may have a diameter that tapers radially inwardly, along at least a portion of its length, as it extends in a distal direction. In some embodiments, the elongated member 120 has a diameter of 0.008 inches (0.020 cm), 0.010 inches (0.254 cm), 0.014 inches (0.036 cm), 0.018 inches (0.046 cm), or more.

A proximal end of the distal element 140 may be coupled to the elongated member 120 via the connection assembly 130. For example, as shown in the cross-sectional end view of the connection assembly 130 in FIG. 2B, the connection assembly 130 may comprise an outer band 132 positioned around the proximal end of the distal element 140, and an inner band 131 positioned around the elongated member 120. As such, the proximal end of the distal element 140 may be sandwiched between the outer band 132 and the inner band 131, and the connection assembly 130 may be crimped down over the elongated member 120 to fix the connection assembly 130 to the elongated member 120 at a desired location. As shown in FIG. 2C, in some embodiments, the proximal end of the distal element 140 may be secured directly to the elongated member 120 by a single band 133.

In some embodiments, for example as depicted in FIGS. 3 and 4, the treatment device 100 may include a stop on either side of the connection assembly 130 for limiting axial movement of the distal element 140 along the elongated member 120. As shown in FIG. 3, in some examples of the technology, the treatment device 100 includes a first stop 134 fixed to the elongated member 120 proximal to the connection assembly 130 and a second stop 136 fixed to the elongated member 120 distal to the connection assembly 130. The first and second stops 134, 136 may be any shape or size that prevents or inhibits movement of the connection assembly 130 along the elongated member 120. Each of the first and/or second stops 134, 136 may be formed integrally with the elongated member 120 or as a separate component. The first and second stops 134, 136 may be positioned immediately adjacent the proximal and distal ends of the connection assembly 130 such that the connection assembly 130 cannot translate along the elongated member 120. In such embodiments, the second stop 136 may be positioned just distal of the connection assembly 130 at a location that lies within an interior region of the distal element 140. In such embodiments, although the connection assembly 130 and distal element 140 are substantially prevented from axial movement, the connection assembly 130 and distal element 140 are still free to rotate about the elongated member 120, thereby allowing the physician to torque the elongated member 120 while the distal element 140 is in an expanded state.

In some embodiments, the first and second stops 134, 136 may be spaced apart from the corresponding adjacent ends of the connection assembly 130, for example as shown in FIG. 4. In such embodiments, the connection assembly 130 is free to translate along a length of the elongated member 120 equivalent to the distance between the first and second stops 134, 136. Accordingly, the connection assembly 130 and the distal element 140 are free to both rotate about and translate along the elongated member 120.

In some embodiments, the treatment device 100 may include one or more flexible, helically wound coils wrapped around one or more portions of the elongated member 120. The coils may be formed of a smaller diameter wire (such as a 0.003 inch wire). In some embodiments, the coil may be a gold-plated tungsten coil, a platinum coil, or other suitable radiopaque material to facilitate visualization via radiographic imaging. As shown in FIG. 5A, the treatment device 100 may include a proximal coil 150 extending along a length of the elongated member 120 proximal of the connection assembly 130 and/or distal element 140. The proximal coil 150 may extend the entire length of the elongated member 120 that is proximal of the connection assembly 130, or the proximal coil 150 may extend along only a portion of the length of the elongated member 120 that is proximal of the connection assembly 130 (for example, along a short length of the elongated member 120 just proximal of the connection assembly 130). In some embodiments, a distal end of the proximal coil 150 may abut or be joined with a proximal portion of the connection assembly 130 and/or distal element 140. In other embodiments, a distal end of the proximal coil 150 is spaced apart from a proximal end of the connection assembly 130 and/or a proximal end of the distal element 140.

As shown in FIG. 5B, the treatment device 100 may include a distal coil 160 extending along a length of the elongated member 120 distal of the connection assembly 130 and the distal coil 160 may extend distally therefrom, through some or all of the interior of the distal element 140, and optionally distally beyond the distal element 140. A proximal end of the distal coil 160 may abut or be joined to a distal end of the connection assembly 130. In some embodiments, a proximal end of the distal coil 160 is spaced apart from a distal end of the connection assembly 130, such that a portion of the elongated member 120 extends distally of the coil. The distal coil 160 can serve as a distal tip coil of the elongated member 120, providing tip softness and navigability. In some such embodiments, a distalmost portion of the elongated member 120 can extend into an internal lumen of the distal coil 160, to the distal end of the coil where the elongated member may be attached to the coil end via soldering or laser welding.

In some aspects of the technology, the treatment device 100 may include both a proximal coil 150 and a distal coil 160, as depicted in FIG. 6. In any of the foregoing embodiments, the proximal coil 150, the distal coil 160, or both may be supplemented or replaced by a braid.

FIG. 7 shows a treatment device 100 in accordance with the present technology comprising an elongated shaft 170 and a distal element 140 carried by the elongated shaft 170. The elongated shaft 170 may define a lumen that is configured to slidably receive the elongated member 120 therethrough. A distal end of the elongated shaft 170 may abut or be joined end-to-end with a proximal end of the connection assembly 130 and/or a proximal end of the distal element 140. The distal element 140 may be positioned over the elongated member 120. In the configuration of FIG. 7, the elongated member 120 can optionally be slidable within the elongated shaft 170 such that the member and the shaft can be moved independently relative to each other. For example, the shaft 170 may be advanceable over the elongated member 120, which may function in a manner similar to a guidewire for enhanced navigability. Or, the elongated member 120 may be retractable partially or completely into the elongated shaft 170, should it be desired to shorten the distal extension of the device 100 when positioned in tortuous or narrow vasculature.

Figure 8A:
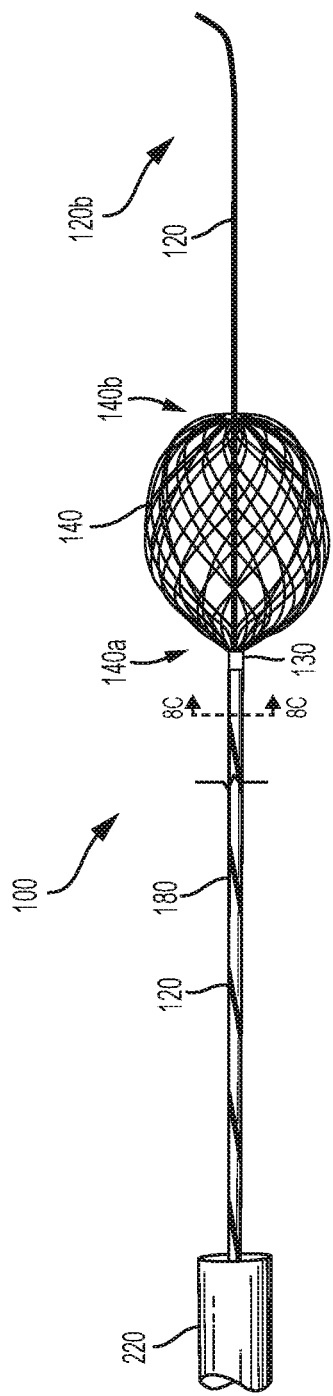
FIG. 8B is an isolated view of a portion of the elongated member shown in FIG. 8A.
FIG. 8C shows a cross-sectional view of the treatment device of FIG. 8A taken along line 8B-8B.
Figure 8C:
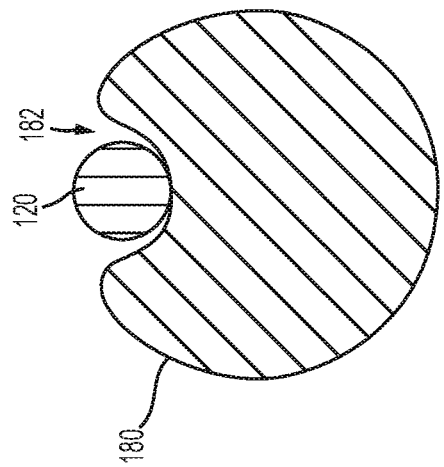
Figure 8B:
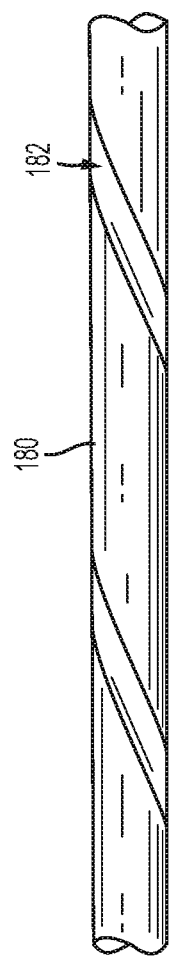

In some embodiments, for example as depicted in FIG. 8A, the treatment device 100 may include a grooved wire 180, the distal element 140, and the elongated member 120. As shown in the isolated view of a portion of the grooved wire 180 in FIG. 8B, the grooved wire 180 may include a groove 182 that spirals (or extends in a straight, non-spiraling fashion) along the wire body and is configured to receive the elongated member 120 therealong. As shown in the cross-sectional view of FIG. 8C, the elongated member 120 may be located within the groove 182. The elongated member 120 can extend distally beyond the distal end of the grooved wire 180, optionally through the distal element 140 and distally beyond it, to its distal end 120b. The distal element 140 can be connected to the grooved wire 180 at or near the distal end of the grooved wire 180. For example, the connection assembly 130 and/or distal element 140 itself may be coupled onto the outer diameter of the grooved wire 180. Alternatively, the distal end of the grooved wire 180 may abut or be joined end-to-end with a proximal end of the connection assembly 130 and/or distal element 140.

Select Embodiments of Distal Elements of the Present Technology

In some embodiments, the distal element 140 can be made of a plurality of filaments or struts. In some embodiments, the distal element 140 can be braided, woven, molded, or cut from a sheet or tube. The filaments or struts can be formed of known flexible materials including shape memory materials (e.g., nitinol), cobalt chromium, platinum, stainless steel, other metals, other metal alloys, or a combination thereof. In some embodiments, the filaments can be wire having a round, ovoid, square, rectangular, or other shape in cross-section. Further, the filaments or struts can be configured such that the distal element 140 is self-expanding. In some embodiments, at least a portion of the distal element 140 will tend to resiliently assume an expanded configuration in the absence of a countervailing force. In some embodiments, the distal element 140 can be fabricated from a first group of filaments formed from platinum or platinum alloy (e.g., platinum/8% tungsten) braided with a second group of filaments formed from cobalt-nickel or cobalt-chromium alloy (e.g., 35N LT™ available from Fort Wayne Metals of Fort Wayne, Ind., USA). The filaments comprise metal and/or polymer wires. One, some, or all of the filaments 144 forming the mesh 142 may be formed of a drawn-filled tube wire comprising a core material surrounded by an outer material. The core material may be a radiopaque material, such as platinum, and the outer material may be a shape memory alloy, such as nitinol, chromium cobalt ("CrCo") alloys, stainless steel alloys, etc.

The wire filaments can be braided into a resulting lattice-like structure. In at least one embodiment, during braiding or winding of the distal element 140, the filaments can be braided using a 1-over-2-under-2 pattern. In other embodiments, however, other methods of braiding can be followed, without departing from the scope of the disclosure. Such other braiding methods can include a 1-over-1-under-1 pattern and 2-over-2-under-2 pattern. In some embodiments, the distal element 140 can be heat set to a desired shape, such as, for example, by placing the distal element 140 in contact with a molding surface of a molding element which defines a desired shape of all or a portion of the distal element 140.

The distal element 140 can comprise pores. In some embodiments, the pores can have a size sufficient to allow fluid such as blood, saline or contrast agent to pass therethrough when the distal element 140 is in an expanded state. In some embodiments, the distal element 140 can exhibit a porosity configured to reduce hemodynamic flow through the distal element 140 to a desired extent. For example, if the distal element 140 is formed of a braid, the sizes of the pores can be controlled by adjusting the numbers of wires in the braid and the pick and pitch of the braid. As will be appreciated, the porosity of the distal element 140 can be adjusted by longitudinally "packing" the distal element 140 during deployment, as known in the art. In some embodiments, the distal element 140 can substantially obstruct flow or can be substantially flow transparent.

In some embodiments, the distal element 140, whether or not it comprises a plurality of filaments, can be coated or surface-treated with one or more compounds, such as, for example, antithrombotic agents.

Figure 9A:
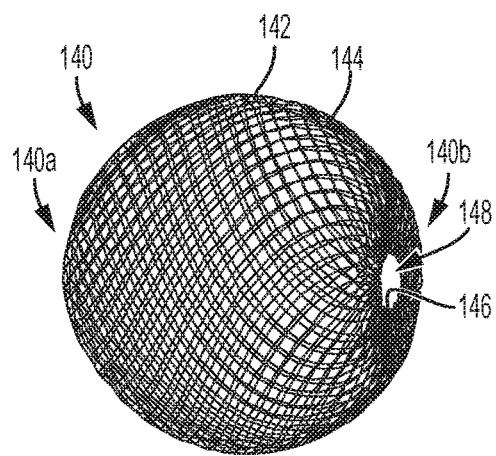
FIG. 9A illustrates a distal element in accordance with aspects of the present technology.
Figure 9B:
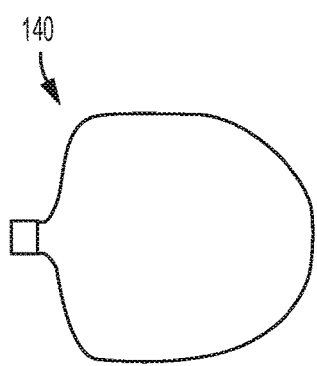
FIG. 9B illustrates a distal element in accordance with aspects of the present technology.
Figure 9C:
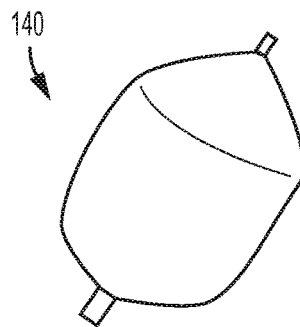
FIG. 9C illustrates a distal element in accordance with aspects of the present technology.

FIG. 9A is a perspective view of a distal element 140 in accordance with several embodiments of the present technology. As shown in FIG. 9A, the distal element 140 may comprise a mesh 142 formed of a plurality of braided filaments 144 that have been heat-set to assume a globular shape when the mesh 142 is in an expanded, unconstrained state. Examples of globular shapes include a sphere, a prolate spheroid (shown in FIG. 9A), an oblate spheroid, and others. The mesh 142 may have inner and outer layers that have proximal ends fixed relative to one another at the connection assembly 130 and meet distally at a distal fold 146 surrounding an aperture 148. An edge of the aperture 148 (for example, 146) can be formed by the mesh 142. In some embodiments, an edge of the aperture 148 can be formed by the mesh 142 around the entire circumference of the aperture 148.

The inner and outer layers may conform to one another at the distal portion 140b (for example as shown in FIG. 9A) to form a curved distal surface. For example, at least at the distal portion 140b of the distal element 140, the inner and outer layers may extend distally and radially inwardly, towards the aperture 148. In some embodiments, the outer and/or inner layers extend distally and radially outwardly from the connection assembly 130, then extend distally and radially inwardly up to a distal terminus of the distal element 140 (e.g., the fold 146). The distal element 140 and/or layers thereof may be curved along its entire length, or may have one or more generally straight portions (for example, as shown in FIGS. 9B, 9C, 9E, and 9F, and elsewhere herein). In some embodiments, the curved surface transitions to a substantially flat, distal-most surface that surrounds the aperture 148. In any case, both the proximal portion 140a and the distal portion 140b of the mesh 142 can form generally closed surfaces. However, unlike at the proximal portion 140a of the mesh 142, the portion of the filaments 144 at or near the fold 146 at the distal portion 140b of the mesh 142 can move relative to one another. As such, the distal portion 140b of the mesh 142 has both the properties of a closed end and also some properties of an open end (like a traditional stent), such as some freedom of movement of the distal-most portions of the filaments and an opening through which a guidewire, guidetube, or other elongated member may pass through.

In some embodiments, each of the plurality of filaments 144 have a first end positioned at the proximal portion 140a of the mesh 142 and a second end also positioned at the proximal portion 140a of the mesh 142. Each of the filaments 144 may extend from its corresponding first end distally along the body of the mesh 142 to the fold 146, invert, then extend proximally along the mesh body to its corresponding second end at the proximal portion 140a of the mesh 142. As such, each of the plurality of filaments have a first length that forms the inner layer of the mesh 142, a second length that forms the outer layer of the mesh 142, and both first and second ends fixed at the proximal portion 140a of the mesh 142. In some embodiments, the distal element 140 may comprise a mesh formed of a single layer, or a mesh formed of three or more layers.

Accordingly, in some embodiments, the distal element 140 may comprise a plurality of filaments that form a mesh that extends longitudinally along the elongated member 120, elongated shaft 170, and/or distal coil 160, and the filaments 144 can terminate at only one end of the distal element 140, either the proximal end as shown in FIGS. 3-8A, or at the distal end. The filaments can form an opening (e.g., aperture 148) at the end opposite the filament ends/terminations. The distal element 140 or its mesh can be unattached to (and slidable over) the elongated member 120 and/or elongated shaft 170 at the end where the opening is located, or otherwise at the end opposite the filament ends/terminations. The elongated member 120 and/or elongated shaft 170 can pass through the opening. Thus, under radially compressive forces, the opening (e.g., aperture 148) enables the distal portion 140b of the distal element 140 to slide and/or move along the elongated member 120, thereby allowing the distal element 140 to radially compress and lengthen with a minimum of resistance. This facilitates a distal element 140 which is self-expanding but also sufficiently soft and compressible to avoid injuring delicate vessels (such as the neurovasculature). The distal element 140 can therefore be sufficiently self-expanding to effectively move or capture thrombus, without posing a risk of injuring the surrounding vessel. In some embodiments, expansion of the distal element causes the aperture to move along the elongated member 120 as the distal element 140 expands.

In some embodiments, the distal end surface of the mesh 142 is completely closed (i.e., does not include an aperture). In some embodiments the filaments are fixed relative to the elongated member 120 or elongated shaft 170 at connections at both the proximal and distal ends of the distal element 140.

The mesh 142 may be formed of 24, 32, 36, 48, 64, 72, 96, 128, or 144 filaments. The mesh 142 may be formed of a range of filament or wire sizes, such as wires having a diameter of from about 0.0004 inches to about 0.0020 inches, or of from about 0.0009 inches to about 0.0012 inches. In some embodiments, each of the wires or filaments have a diameter of about 0.0004 inches, about 0.0005 inches, about 0.0006 inches, about 0.0007 inches, about 0.0008 inches, about 0.0009 inches, about 0.001 inches, about 0.0011 inches, about 0.0012 inches, about 0.0013 inches, about 0.0014 inches, about 0.0015 inches, about 0.0016 inches, about 0.0017 inches, about 0.0018 inches, about 0.0019 inches, or about 0.0020 inches. In some embodiments, all of the filaments 144 of the braided mesh 142 may have the same diameter. For example, in some embodiments, all of the filaments 144 have a diameter of about 0.001 inches. In some embodiments, some of the filaments 144 may have different cross-sectional diameters. For example, some of the filaments 144 may have a slightly thicker diameter to impart additional strength to the braided layers. In some embodiments, some of the filaments can have a diameter of about 0.001 inches, and some of the filaments can have a diameter of greater than 0.001 inches. The thicker filaments may impart greater strength to the braid without significantly increasing the device delivery profile, with the thinner wires offering some strength while filling-out the braid matrix density.

Figure 9D:
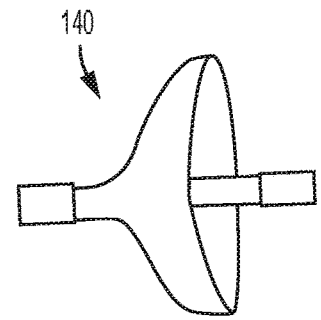
FIG. 9D illustrates a distal element in accordance with aspects of the present technology.
Figure 9E:
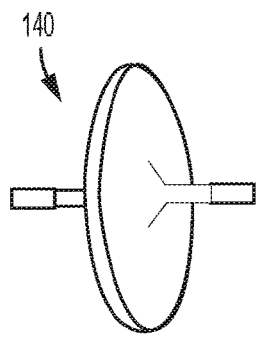
FIG. 9E illustrates a distal element in accordance with aspects of the present technology.
Figure 9F:
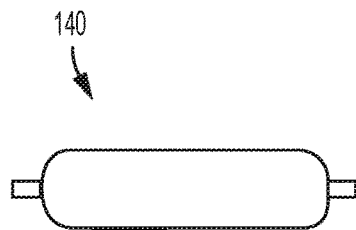
FIG. 9F illustrates a distal element in accordance with aspects of the present technology.

The distal element 140 can have different shapes and sizes in an expanded, unconstrained state. For example, the distal element 140 may have a bullet shape (FIG. 9B), a barrel-shape, an egg shape, a dreidel shape (e.g., FIG. 9C), a bowl shape (e.g., FIG. 9D), a disc shape (e.g., FIG. 9E), a cylindrical or substantially cylindrical shape (e.g., FIG. 9F), etc.

The distal elements 140 of the present technology may comprise a range of sizes. For example, the distal elements 140 of the present technology may have a maximum cross-sectional dimension of at least 2.0 mm, 2.5 mm, 3.0 mm, 3.5 mm, 4.0 mm, 4.5 mm, 5.0 mm, 5.5 mm, 6.0 mm, 6.5 mm, 7.0 mm, 7.5 mm, or 8.00 mm.

Figure 10A:
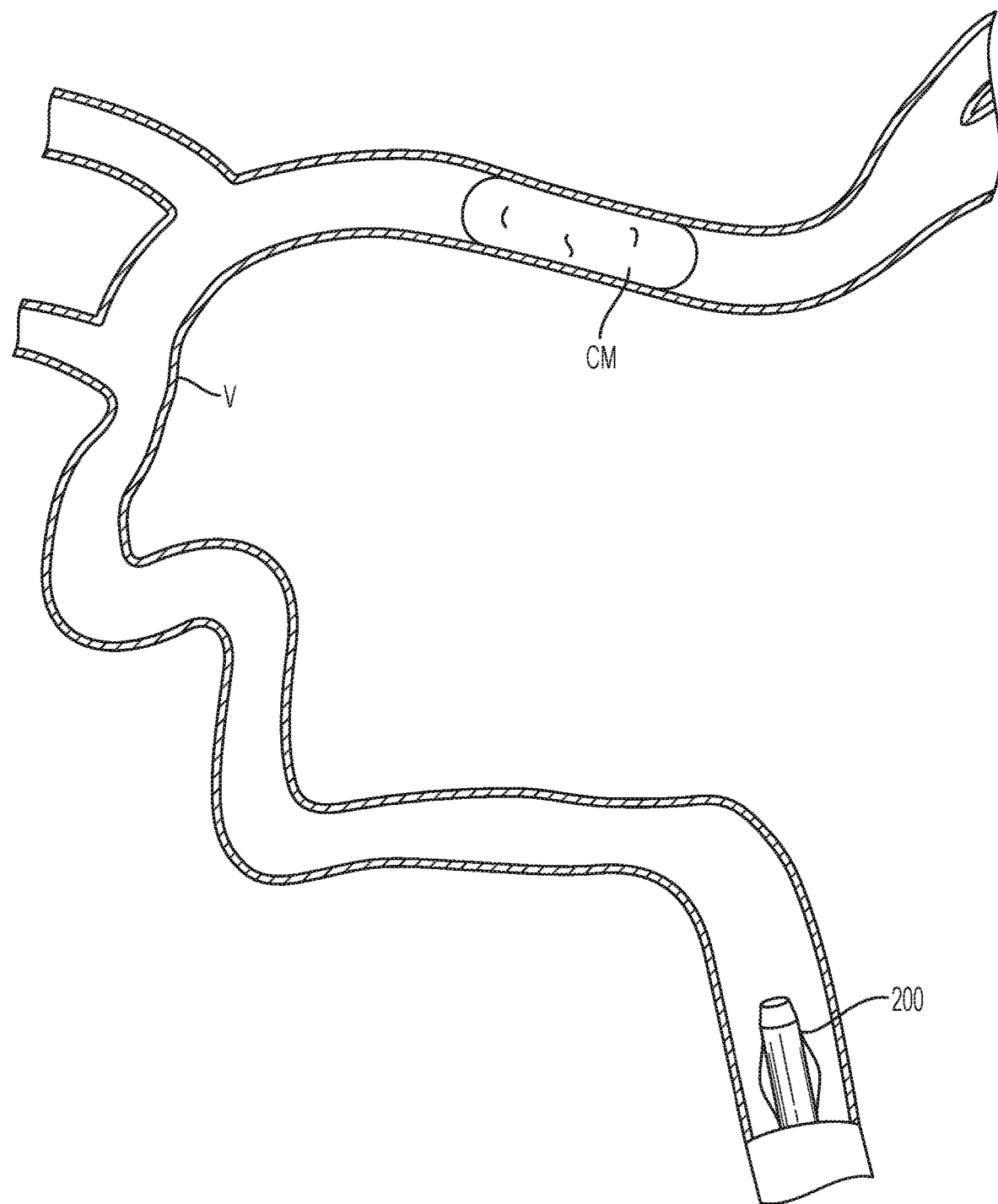
FIG. 10A illustrates a method of removing clot material from a blood vessel lumen in accordance with one or more embodiments of the present technology.
Figure 10B:
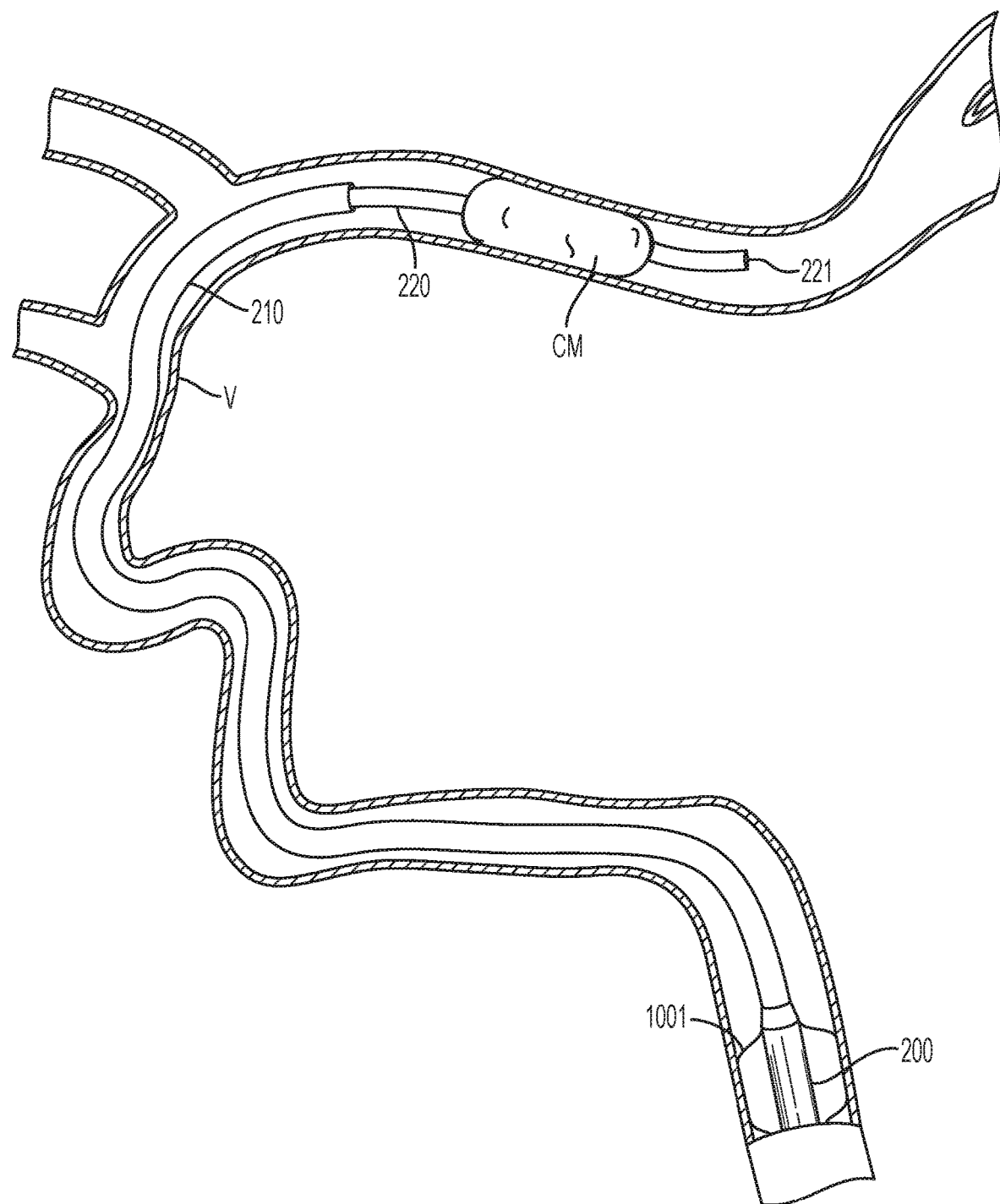
FIG. 10B illustrates a method of removing clot material from a blood vessel lumen in accordance with one or more embodiments of the present technology.

FIGS. 10A-10E illustrate a method of removing clot material CM from the lumen of a blood vessel V using a treatment system 10 as described above. As shown in FIG. 10A, the first catheter 200 can be advanced through the vasculature and positioned within the blood vessel such that a distal portion of the first catheter 200 is proximal of the clot material CM. As shown in FIG. 10B, the second catheter 210 may be advanced through the first catheter 200 until a distal portion of the second catheter 210 is at or proximal to the clot material CM. The first catheter 200 can be secured in place using a balloon 1001 or other expandable member configured to engage the vessel wall. Next, the third catheter 220 may be advanced through the second catheter 210 so that a distal portion of the third catheter 220 is positioned at or near the clot material CM. In some embodiments, the third catheter 220 may cross the clot material CM and be positioned such that a distal terminus 221 of the third catheter 220 is distal of the clot material CM. The distal element 140 may then be advanced through the third catheter 220 in a low-profile configuration until a distal terminus of the distal element 140 is at or adjacent the distal terminus of the third catheter 220.

Figure 10C:
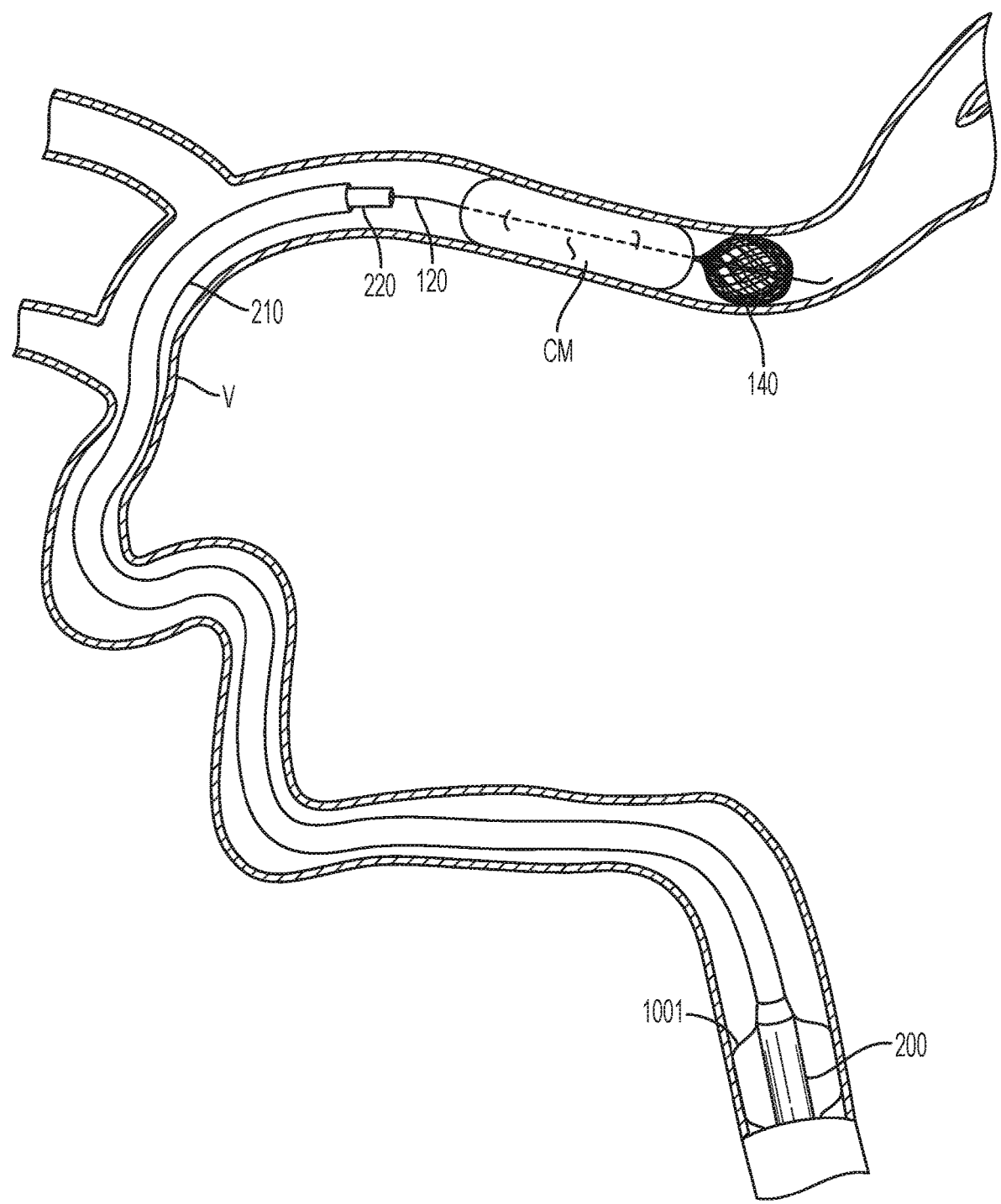
FIG. 10C illustrates a method of removing clot material from a blood vessel lumen in accordance with one or more embodiments of the present technology.

As shown in FIG. 10C, the third catheter 220 may be withdrawn proximally relative to the distal element 140 to release the distal element 140, thereby allowing the distal element 140 to self-expand at least partially distal to the clot material CM. In some embodiments, the distal element 140 may be expanded distal of the clot material CM such that no portion of the distal element 140 is engaging the clot material CM while the distal element 140 is in the process of expanding toward the vessel wall. In some embodiments, the distal element 140 is configured to expand into contact with the wall of the vessel V, or the distal element 140 may expand to a diameter that is less than that of the blood vessel lumen such that the distal element 140 does not engage the entire circumference of the blood vessel wall.

Figure 10D:
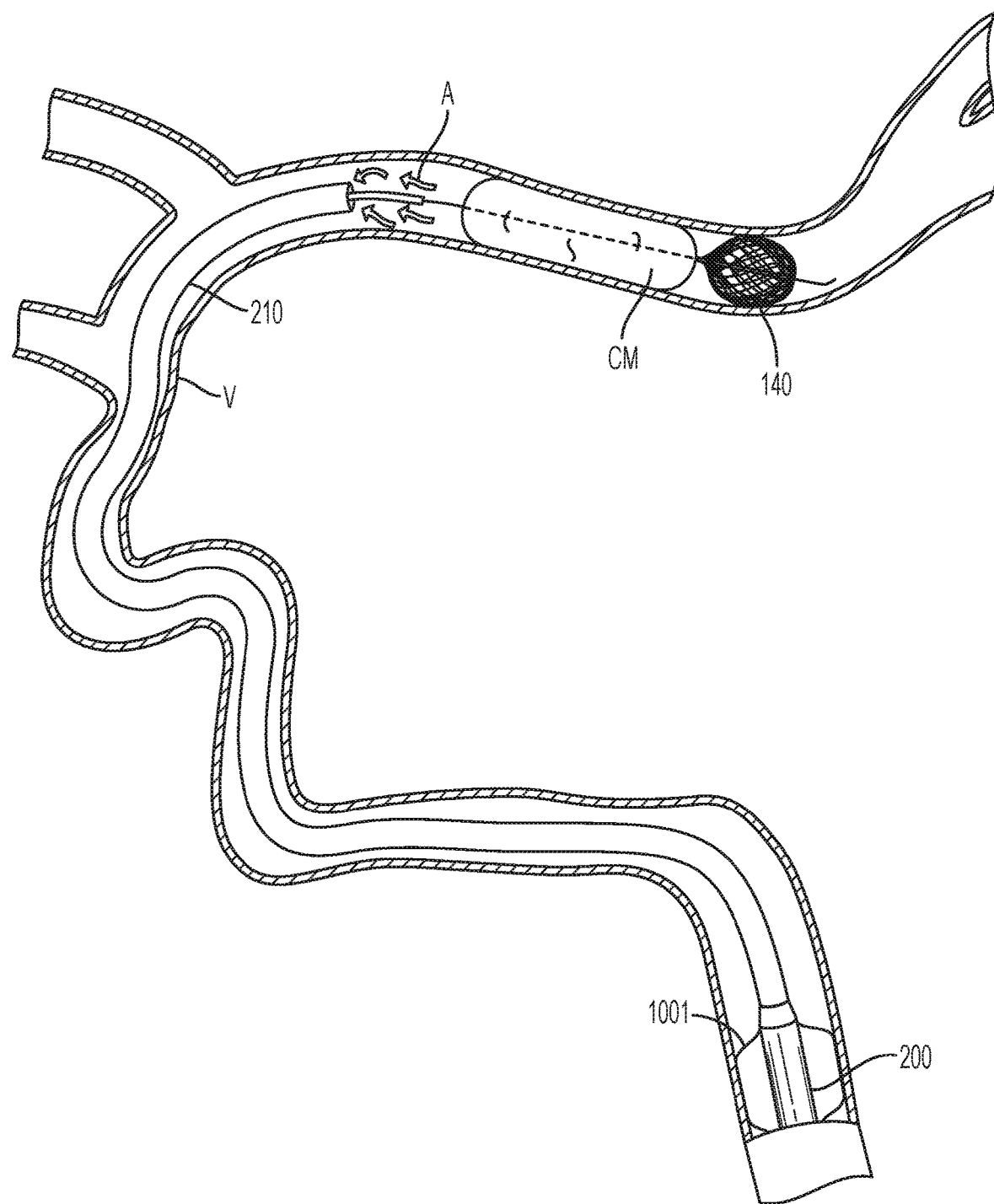
FIG. 10D illustrates a method of removing clot material from a blood vessel lumen in accordance with one or more embodiments of the present technology.

As shown in FIG. 10D, aspiration may be applied to the treatment site via the second catheter 210. For example, following deployment of the distal element 140, the third catheter 220 can be retracted and removed from the lumen of the second catheter 210. The treatment site can then be aspirated via the second catheter 210, for example via a suction source such as a pump or syringe coupled to a proximal portion of the second catheter 210.

In some embodiments, aspiration is applied while the distal element 140 is being retracted into the second catheter 210. During retraction, the proximal face of the distal element 140 can engage with the clot material CM and urge it proximally towards the distal end of the second catheter 210. Aspiration at this stage, and/or the presence of the distal element 140 distal of the clot material CM, can help secure the clot material CM within the second catheter 210 and prevent any dislodged portion of the clot material CM from escaping the second catheter 210 and being released back into the vessel V.

Figure 10E:
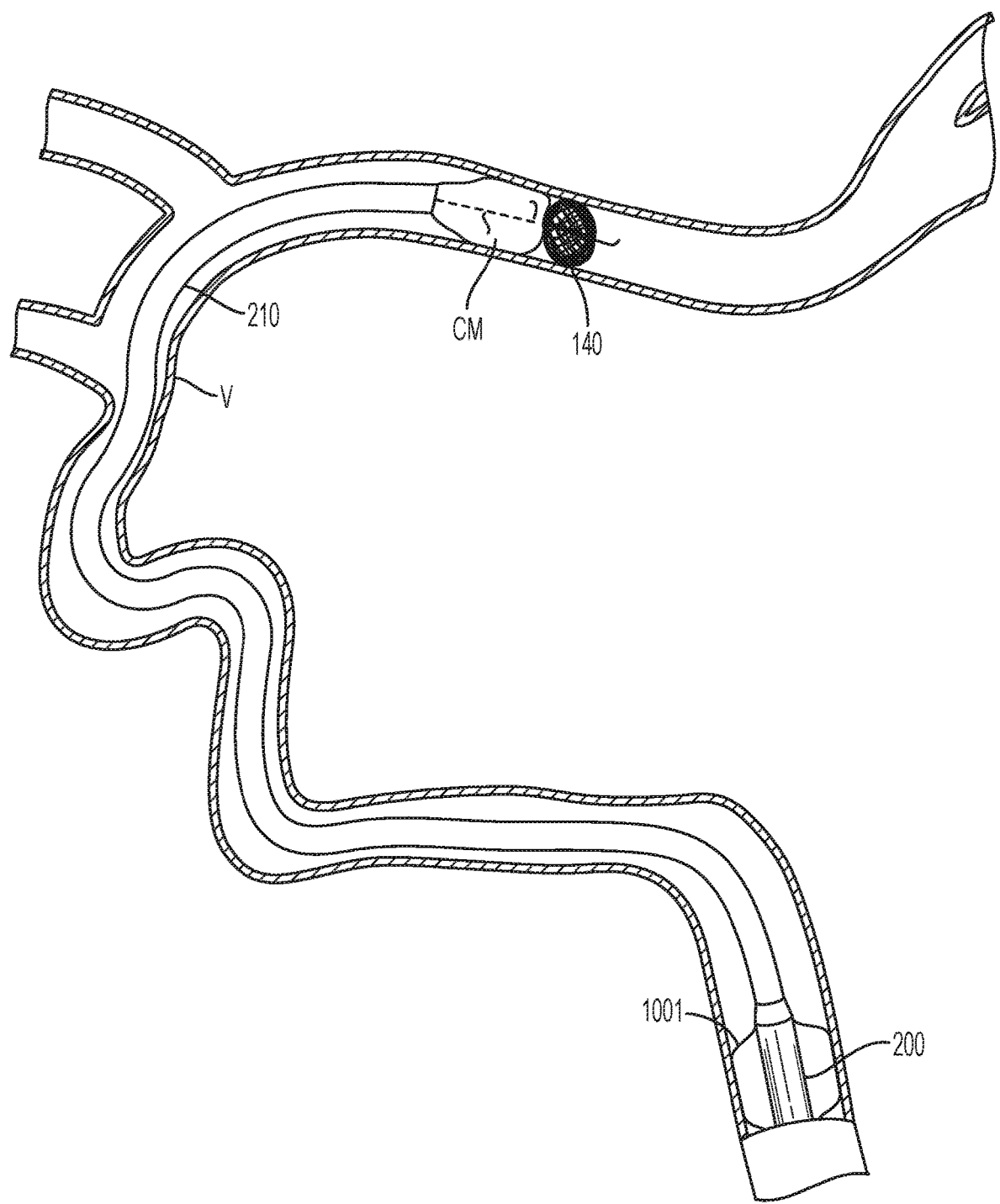
FIG. 10E illustrates a method of removing clot material from a blood vessel lumen in accordance with one or more embodiments of the present technology.

With reference to FIG. 10E, while the distal element 140 is engaged with the clot material CM, the clot material CM can be removed. For example, the distal element 140, with the clot material CM gripped and/or pushed thereby, can be retracted proximally (for example, along with the second catheter 210 and, optionally, the third catheter 220). The second catheter 210, distal element 140, and associated clot material CM may then be withdrawn from the patient, optionally through one or more larger surrounding catheters, such as the first catheter 200.

In FIG. 10E, the clot material CM has been moved to at least partially enter the second catheter 210. In some embodiments, the clot material CM can substantially block the lumen of the second catheter 210, thereby creating a "corking" effect that may be noticeable to a clinician supplying negative pressure to the second catheter 210. Once the second catheter 210 is corked with the clot material CM, it becomes increasingly difficult to supply continued negative pressure to the second catheter 210. This corking effect can indicate to a clinician that the clot material CM has been engaged by the second catheter 210 and that the clot material CM and second catheter 210 can be retracted through the vessel V and into the first catheter 200 or other surrounding catheter.

Figure 11:
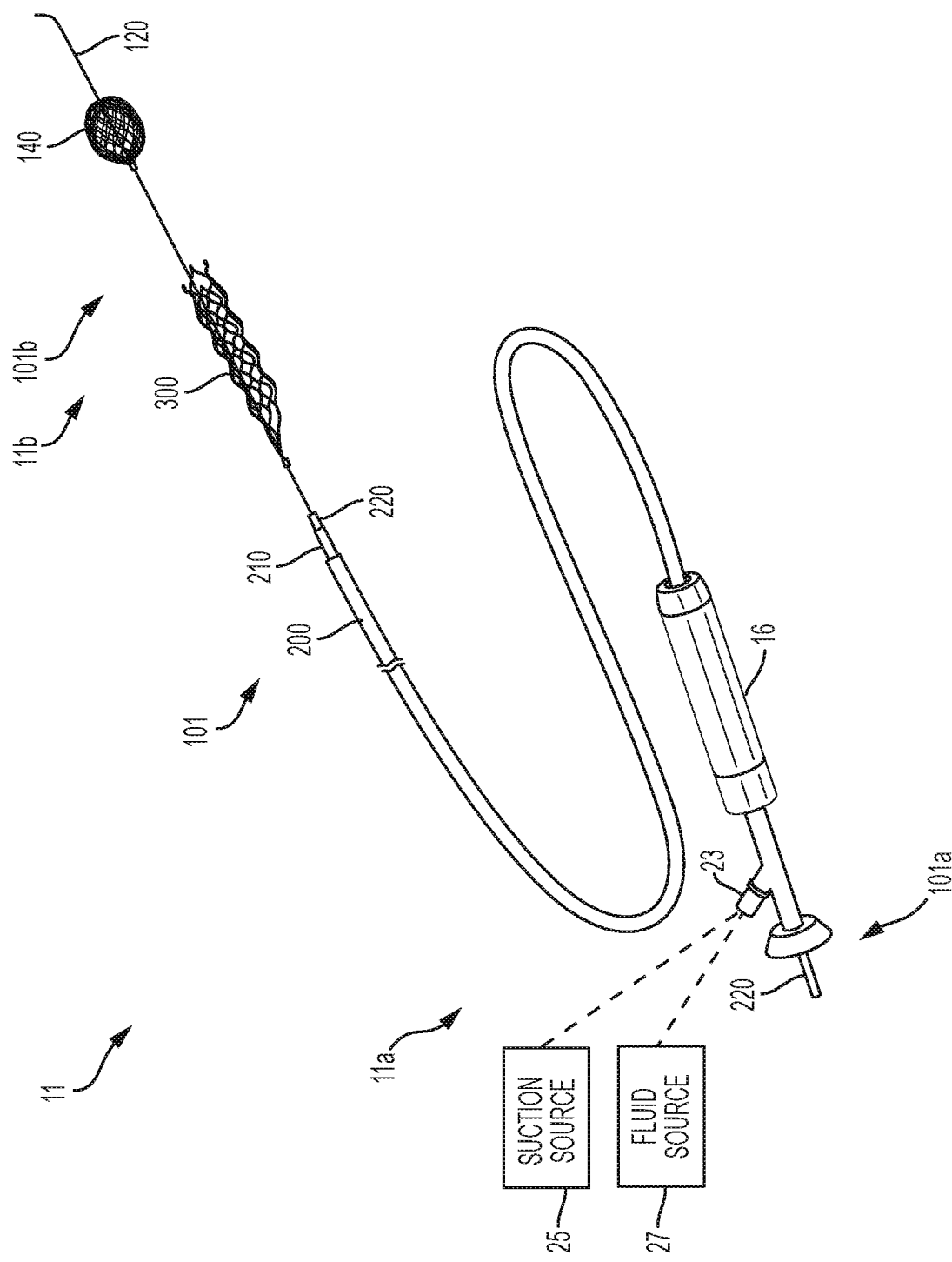
FIG. 11 shows a perspective view of a treatment system for retrieving material from a body lumen, in accordance with one or more embodiments of the present technology.

III. Select Embodiments of Treatment Systems Employing Interventional Elements with the Distal Elements Disclosed Herein FIG. 11 illustrates a view of a treatment system 11 for retrieving material from a body lumen, according to one or more embodiments of the present technology. Several features of the treatment system 11 can be similar to the treatment system 10 shown in FIG. 1 and described elsewhere herein. As shown in FIG. 11, the treatment system 11 includes a treatment device 101 having a proximal portion 101a configured to be extracorporeally positioned during treatment, and a distal portion 101b configured to be intravascularly positioned within a blood vessel (such as an intracranial blood vessel) at a treatment site at or proximate a thrombus. The treatment system 11 may include a handle 16 at the proximal portion 101a, a distal element 140, an interventional element 300, and a plurality of elongated shafts or members extending between the proximal and distal portions 101a and 101b. For example, in some embodiments, such as that shown in FIG. 11, the treatment system 11 may include one, some, or all of: a first catheter 200 (such as a guide catheter or balloon guide catheter), a second catheter 210 (such as a distal access catheter or aspiration catheter) configured to be slidably disposed within a lumen of the first catheter 200, and a third catheter 220 (such as a microcatheter) configured to be slidably disposed within a lumen of the second catheter 210. In some embodiments, the first catheter 200 is coupled to the handle 16, which provides proximal access to the second catheter 210, the third catheter 220, the distal element 140 and/or the interventional element 300. Each of the distal element 140 and the interventional element 300 may be configured to be slidably disposed within a lumen of the first catheter 200, the second catheter 210, and/or the third catheter 220. Any of the embodiments or versions of the above-mentioned components that are described herein with reference to the treatment system 10 of FIG. 1 can be employed in connection with the treatment system 11 as well.

In some embodiments, the treatment system 11 includes a suction source 25 (e.g., a syringe, a pump, etc.) configured to be fluidly coupled (e.g., via a connector 23) to a proximal portion of one or more of the first catheter 200, the second catheter 210, and/or the third catheter 220 to apply negative pressure therethrough. In some embodiments, the treatment system 11 includes a fluid source 27 (e.g., a fluid reservoir, a syringe, pump, etc.) configured to be fluidly coupled (e.g., via the connector 23) to a proximal portion of one or more of the first catheter 200, the second catheter 210, and/or the third catheter 220 to supply fluid (e.g., saline, contrast agents, a drug such as a thrombolytic agent, etc.) to the treatment site.

According to some embodiments, for example as shown in FIG. 11, each of the catheters 200, 210, and 220 can be formed as a generally tubular member extending along and about a central axis and terminating in a respective distal end. According to some embodiments, the third catheter 220 is generally constructed to track over a conventional guidewire in the cervical anatomy and into the cerebral vessels associated with the brain and may also be chosen according to several standard designs that are generally available. Accordingly, the third catheter 2202 can have a length that is at least 125 cm long, and more particularly may be between about 125 cm and about 175 cm long. Other designs and dimensions are contemplated.

The second catheter 210 can be sized and configured to slidably receive the third catheter 220 therethrough. As noted above, the second catheter 210 can be coupled at a proximal portion to a suction source 25 such as a pump or syringe in order to supply negative pressure to a treatment site. The first catheter 200 can be sized and configured to slidably receive both the second catheter 210 and the third catheter 220 therethrough. In some embodiments, the first catheter 200 is a balloon-guide catheter having an inflatable balloon or other expandable member that can be used to anchor the first catheter 200 with respect to a surrounding vessel. As previously described in more detail with respect to FIGS. 10A-10E, in operation the first catheter 200 can first be advanced through a vessel and then a balloon can be expanded to anchor the first catheter 200 in place and/or arrest blood flow from areas proximal of the balloon. Next, the second catheter 210 can be advanced through the first catheter 200 until its distal end extends distally beyond the distal end of the first catheter 200. The second catheter 210 can be positioned such that its distal end is adjacent a treatment site (e.g., a site of a blood clot within the vessel). The third catheter 220 may then be advanced through the second catheter 210 until its distal end extends distally beyond the distal end of the second catheter 210.

According to some embodiments, the bodies of the catheters 200, 210, and 220 can be made from various thermoplastics, e.g., polytetrafluoroethylene (PTFE or TEFLON®), fluorinated ethylene propylene (FEP), high-density polyethylene (HDPE), polyether ether ketone (PEEK), etc., which can optionally be lined on the inner surface of the catheters or an adjacent surface with a hydrophilic material such as polyvinylpyrrolidone (PVP) or some other plastic coating. Additionally, either surface can be coated with various combinations of different materials, depending upon the desired results. Any one or more of the catheters 200, 210, 220 may incorporate a reinforcement structure in its construction, e.g. layered between an inner lubricious liner and an outer polymeric jacket. Such a reinforcement structure can be metallic and/or polymeric, and comprise a tubular braid, a coil, a hypotube (e.g. a spiral-cut or slotted-cut hypotube), or combinations of the foregoing. Suitable metals for constructing the reinforcement structure include without limitation stainless steel, nitinol, and cobalt-chromium.

FIG. 12 is a side schematic view of an embodiment of a portion of the system 11 and treatment device 101 shown in FIG. 11. The system 11 and/or treatment device 101 includes the distal element 140, the interventional element 300, and the elongated member 120 extending from the body of the first catheter 200 and through at least a portion of the interventional element 300 and distal element 140. As shown in FIG. 12, the distal element 140 is distal to the interventional element 300 and spaced apart from a distal end portion 120b (e.g., a distal tip or terminus) of the elongated member 120. In some embodiments, the distal element 140 may be at the distal end portion 120b or distal terminus of the elongated member 120. In lieu of the foregoing, the distal element 140 may in some embodiments be proximal of the interventional element 300.

As shown in FIG. 12, the distal element 140 includes a proximal portion 140a, a distal portion 140b, and a connection assembly 130 disposed over the elongated member 120. As described in more detail elsewhere herein, the distal element 140 (e.g., the proximal portion of the distal element 140) can be slidably coupled, rotatably coupled, or fixedly coupled to the elongated member 120, e.g., via the connection assembly 130. In the embodiment shown in FIG. 12, the distal element 140 is fixedly coupled to the elongated member 120 via the connection assembly 130 such that the distal element 140 cannot longitudinally move relative to the elongated member 120. In such embodiments, the distal element 140 may be rotatably and/or slidably coupled to the elongated member 120.

The distal element 140 may comprise an expandable mesh having a low-profile state or configuration for delivery to a deployment location, and an expanded state or configuration in which at least a portion of the mesh is configured to be in apposition with the blood vessel wall. The distal element 140 is configured to expand into contact with the blood vessel wall at desired locations along the intravascular path to the treatment site as well as at the treatment site to anchor and/or stabilize the elongated member 120 or any portion of the treatment system 11 at the desired location. As previously described, the distal element 140 may also be configured to facilitate removal of the thrombus from the treatment site. Any of the distal elements 140 disclosed above with reference to FIGS. 1-9F may be utilized in the treatment devices 101 disclosed herein with respect to FIGS. 11-17.

As shown in FIG. 12, the interventional element 300 includes a proximal portion 300a, a distal portion 300b, and a connection assembly 302 at the proximal portion 300a. As described in more detail below, the interventional element 300 (e.g., the proximal portion 300a of the interventional element 300) can be slidably coupled, rotatably coupled, or fixedly coupled to the elongated member 120, e.g., via the connection assembly 302. As shown in FIG. 12, the interventional element 300 is fixedly coupled to the elongated member 120 via the connection assembly 302 such that the interventional element 300 cannot longitudinally move relative to the elongated member 120. In such embodiments, the interventional element 300 may be rotatably coupled to the elongated member 120.

The interventional element 300 further includes an open cell framework or body of struts and cells extending distally from the connection assembly 302. In some embodiments, the distal portion 300b of the interventional element 300 can be generally tubular (e.g., cylindrical), and the proximal portion 300a of the interventional element 300 can taper proximally to the connection assembly 302. In some embodiments, the distal portion 300b (e.g., the distal terminus) coincides with the distal end portion 120b of the elongated member 120 or treatment device 101. The interventional element 300 has a low-profile configuration (not shown) when constrained within the first catheter 200, and an expanded configuration for securing and/or engaging clot material or other obstructions within a blood vessel lumen (e.g., a cerebral blood vessel lumen) and/or for restoring blood flow within the blood vessel.

In some embodiments the interventional element 300 is a mesh structure formed of a superelastic material (e.g., Nitinol) or other resilient or self-expanding material configured to self-expand when released from the delivery catheter. For example, in some embodiments the interventional element 300 may be a stent and/or stent retriever, such as Medtronic's Solitaire™ Revascularization Device, Stryker Neurovascular's Trevo® ProVue™ Stentriever, or other suitable devices. In other embodiments, the interventional element 300 may include a plurality of braided filaments. Examples of suitable interventional element 300 include any of those disclosed in U.S. Pat. No. 7,300,458, filed Nov. 5, 2007, U.S. Pat. No. 8,940,003, filed Nov. 22, 2010, U.S. Pat. No. 9,039,749, filed Oct. 1, 2010, U.S. Pat. No. 8,066,757, filed Dec. 28, 2010, and U.S. Pub. No. 2018/0325534, filed May 12, 2017, each of which is incorporated by reference herein in its entirety.

FIGS. 13-17 are side schematic views of embodiments of a portion of the system 11 and treatment device 101 shown in FIG. 12, in which the distal element 140 and/or interventional element 300 are movable relative to one another and/or the elongated member 120. Unless stated otherwise, each of the distal element 140 and/or the interventional element 300 may be rotatably and/or slidably coupled to the elongated member 120 (or fixedly mounted without capability to rotate or slide) in any of the embodiments shown in FIGS. 13-17. As such, any rotation of the distal element 140 and/or the interventional element 300 that occurs during movement of the treatment device 101 through a catheter in tortuous vasculature is not transferred to the elongated member 120 (or only a reduced portion of such rotation is transferred to the elongated member). By reducing or preventing rotation or "winding up" of the elongated member 120, the rotatably coupled feature can help reduce the force needed to move the treatment device 101 through a catheter, and any "whipping" effect that can occur as the distal element 140 and/or the interventional element 300 counter-rotates suddenly upon exiting the catheter. In addition, this capability allows the elongated member 120 to be rotated to facilitate pointing the distal end 120b of the elongated member 120 in the desired direction of advancement (e.g. at a vessel junction or curve), without need to correspondingly rotate the interventional element 300 and/or distal element 140 within the blood vessel or catheter. Without the ability to rotate the elongated member 120 relative to the element(s) 300, 140, it would be necessary to rotate the entire system 11 to navigate it as desired, which can be physically difficult if the element(s) 300, 140 are compressed within a catheter or potentially injurious when they are expanded in a blood vessel.

In some embodiments of FIGS. 13-17 in which one or both of the distal element 140 and/or interventional element 300 are not fixedly coupled to the elongated member 120 (e.g., are rotatably and/or slidably coupled to the elongated member 120), the system 11 and treatment device 101 can include a second elongated member 120. In such embodiments, the distal element 140 and interventional element 300 may be disposed on separate elongated members 120 (e.g., respective first and second elongated members) such that movement of one of the distal element 140 or interventional element 300 via movement of the corresponding elongated member 120 is controlled separately from movement of the other of the distal element 140 and interventional element 300.

FIG. 13 is a side schematic view of an embodiment of a portion of the system 11 and treatment device 101 in which the interventional element 300 is slidably coupled to the elongated member 120 via a slidable connection assembly 302 positioned on the elongated member 120. At least one stop 304 is fixedly coupled to the elongated member 120 proximal of the interventional element 300 and/or connection assembly 302. In such embodiments, the interventional element 300 can be longitudinally movable relative to the elongated member 120 and/or the distal element 140 between the stop 304 and the distal element 140. The stop 304 may include any shape and/or size that prevents or inhibits movement of the interventional element 300 proximally thereof. In some embodiments, the stop 304 may be formed integrally with the elongated member 120 or as a separate component. The distal element 140 can be fixedly and/or slidably/rotatably coupled to the elongated member 120 via connection assembly 130.

The system 11 and treatment device 101 of FIG. 13 can optionally include a stop 306 (e.g., a second stop) fixedly coupled to the elongated member 120 between the interventional element 300 (e.g., the connection assembly 302 thereof) and the distal element 140. In such embodiments, the interventional element 300 can be slidably/rotatably coupled to the elongated member 120, e.g., via connection assembly 302, and longitudinally movable relative to the elongated member 120 between the stops 304 and 306.

FIG. 14 is a side schematic view of another embodiment of a portion of the system 11 and treatment device 101 in which the distal element 140 is slidably coupled to the elongated member 120 via a slidable connection assembly 130 positioned on the elongated member 120. At least one stop 308 is fixedly coupled to the elongated member 120 distal of the distal element 140. In such embodiments, the distal element 140 can be longitudinally movable relative to the elongated member 120 between the stop 308 and the interventional element 300. The stop 308 may include any shape and/or size that inhibits movement of the distal element 140 distally thereof. In some embodiments, the stop 308 may be formed integrally with the elongated member 120 or as a separate component. The interventional element 300 can be fixedly and/or rotatably coupled to the elongated member 120, e.g. via connection assembly 302.

The system 11 and/or treatment device 101 of FIG. 14 can optionally include a stop 310 (e.g., a second stop) fixedly coupled to the elongated member 120 between the interventional element 300 (e.g., the distal portion 300b of the interventional element 300) and the connection assembly 130 of the distal element 140. In such embodiments, the distal element 140 can be slidably coupled to the elongated member 120, e.g., via connection assembly 130, and longitudinally movable relative to the elongated member 120 between the stops 308 and 310.

FIG. 15 is a side schematic view of another embodiment of a portion of the system 11 and treatment device 101 in which the distal element 140 and the interventional element 300 are each slidably coupled to the elongated member 120 via their respective slidable connection assemblies 130, 302 positioned on the elongated member 120. A stop 304 (e.g., a first stop) can be fixedly coupled to the elongated member 120 proximal of the interventional element 300, a stop 308 (e.g., a second stop) can be fixedly coupled to the elongated member 120 distal of the distal element 140, and a stop 310 (e.g., a third stop) fixedly coupled to the elongated member 120 between the interventional element 300 (e.g., the distal portion 300b of the interventional element 300) and the distal element 140. In such embodiments, (a) the distal element 140 can be slidably coupled to the elongated member 120, e.g., via connection assembly 130, and longitudinally movable relative to the elongated member 120 between the stops 308 and 310, and (b) the interventional element 300 can be slidably coupled to the elongated member 120, e.g., via connection assembly 302, and longitudinally movable relative to the elongated member 120 between the stops 304 and 310.

FIG. 16 is a side schematic view of another embodiment of a portion of the system 11 and treatment device 101 in which the distal element 140 is slidably coupled to the elongated member 120. As shown in FIG. 14, the system 11 and/or treatment device 101 includes the interventional element 300 and distal element 140 disposed over the elongated member 120, and a stop 308 fixedly coupled to the elongated member 120 distal of the distal element 140, and a tube 312 disposed over the elongated member 120 and coupled to the interventional element 300 (e.g., the proximal portion 300a of the interventional element 300). In some embodiments, the elongated member 120 can move longitudinally within a lumen of the tube 312. As such, the elongated member 120 and the distal element 140 can together be slidably moved with respect to the interventional element 300 and the tube 312. In addition or alternatively, the distal element 140 can be slidably coupled to the elongated member 120, e.g., via connection assembly 130, such that the distal element 140 is longitudinally movable relative to the elongated member 120 at least between the stop 308 and the interventional element 300. The tube 312 can extend to the proximal end or portion 100a of the treatment device 100 (and/or to the proximal end or portion 10a of the treatment system 10), e.g. to allow a user to manipulate both the tube 312 and the elongated member 120 independently of each other, from the proximal ends thereof. Accordingly, this configuration permits some slidability of the distal element 140 with respect to the elongated member 120, and also permits the interventional element 300 and the distal element 140 to be slidably and/or rotatably moved independently of one another. In some instances, it can be useful to controllably vary the longitudinal distance between the distal portion 300b (e.g., the distal end) of the interventional element 300 and the proximal portion 140a (e.g., the proximal end) of the distal element 140. For example, following deployment of the interventional element 300 into or adjacent a thrombus, the distal element 140 can be slidably retracted or advanced relative to the interventional element 300 and/or thrombus as desired by the clinician. Among other advantages, this capability also allows for adjustability of the system 100 in order to fit the vasculature which varies from one patient to another.

As shown in FIG. 16, in some embodiments, the system 11 and/or treatment device 101 can optionally include a stop 310 (e.g., a second stop) fixedly coupled to the elongated member 120 between the interventional element 300 (e.g., the distal portion 300b of the interventional element 300) and the distal element 140. In such embodiments, the distal element 140 can be slidably coupled to the elongated member 120, e.g., via connection assembly 130, and longitudinally movable relative to the elongated member 120 between the stops 308 and 310.

FIG. 17 is a side schematic view of another embodiment of a portion of the system 11 and treatment device 101. As shown in FIG. 17, the system 11 and/or treatment device 101 includes the interventional element 300, the distal element 140 (e.g., a first distal element) located distal of the interventional element 300, and a distal element 141 (e.g., a second distal element) located proximal of the interventional element 300. These components are slidably coupled to the elongated member 120 via their respective connection assemblies 302, 130. The system 11 and treatment device 101 can further include a stop 308 (e.g., a first stop) fixedly coupled to the elongated member 120 distal of the distal element 140, a stop 314 (e.g., a second stop) fixedly coupled to the elongated member 120 proximal of the distal element 141, and a stop 310 (e.g., a third stop) fixedly coupled to the elongated member 120 between the distal element 140 and the interventional element 300 (e.g., the distal portion 300b of the interventional element 300). In such embodiments, one or more of the distal element 140, distal element 141, and interventional element 300 may be rotatably and/or slidably coupled to the elongated member 120. For example, only the distal element 140, only the interventional element 300, only the distal element 141, both the distal element 140 and the interventional element 300, both the distal element 141 and the interventional element 300, both the distal elements 140 and 141, or all of the distal element 140, interventional element 300, and distal element 141 may be rotatably and/or slidably coupled to the elongated member. For example, as shown in FIG. 17: (a) the distal element 140 can be slidably coupled to the elongated member 120, e.g., via connection assembly 130, and longitudinally movable relative to the elongated member 120 between the stops 308 and 310, (b) the interventional element 300 can be slidably coupled to the elongated member 120, e.g., via connection assembly 302, and longitudinally movable relative to the elongated member 120 between the distal element 141 and stop 310, and (c) the distal element 141 can be slidably coupled to the elongated member 120, e.g., via connection assembly 130, and longitudinally movable relative to the elongated member 120 between the stop 314 and the interventional element 300.

In another embodiment of the system 11 and treatment device 101, the distal element(s) 140 may be omitted and the interventional element 300 rotatably (or rotatably and slidably) mounted on the elongated member 120. This embodiment would offer the advantage of being navigable (along with, and while positioned in a distal portion of, the third catheter 220) to the treatment area via the rotatable distal portion 120b of the elongated member 120 and the third catheter 220.

The embodiments of the treatment device 101 shown in FIGS. 13-17 offer useful advantages by allowing for relative movement of the active components of the device during a treatment procedure, which helps accommodate variations in vasculature from patient to patient. The physician is therefore provided some freedom to place the interventional element 300, distal element(s) 140, and/or any distal extension of the elongated member 120 to ensure they will be most effective and/or safely deployed, taking into consideration the vasculature of the specific patient being treated. Similarly, these embodiments can allow the physician to adjust the effective length of (e.g., shorten) any distal extension of the elongated member and avoid needlessly endangering the vasculature distal of the treatment site.

Figure 18A:
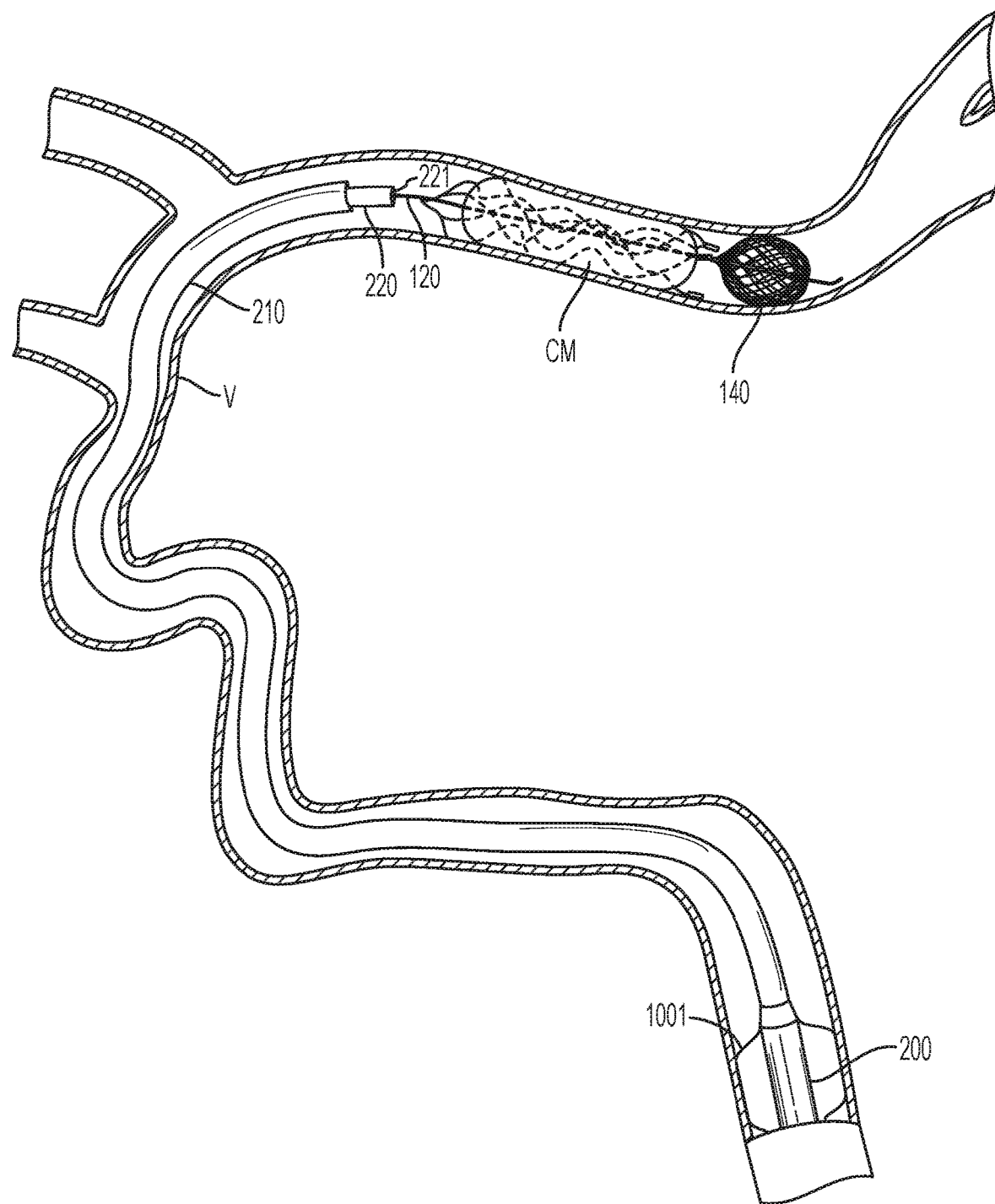
FIGS. 18A, 18B, 18C and 18D illustrate a method of removing clot material from a blood vessel lumen, in accordance with one or more embodiments of the present technology.

FIGS. 18A-18D illustrate a method of removing clot material CM from the lumen of a blood vessel V using the treatment system 11, in accordance with embodiments of the present technology. Similar to the method described above with respect to FIGS. 10A and 10B, the first catheter 200 can be advanced through the vasculature and positioned within the blood vessel V such that a distal portion of the first catheter 200 is proximal of the clot material CM (for example, as shown in FIG. 10A). The second catheter 210 may be advanced through the first catheter 200 until a distal portion of the second catheter 210 is at or proximal to the clot material CM. In some embodiments, the first catheter 200 can be secured in place using a balloon 1001 or other expandable member configured to engage the vessel wall. Next, the third catheter 220 may be advanced through the second catheter 210 so that a distal portion of the third catheter 220 is positioned at or near the clot material CM. In some embodiments, the third catheter 220 may be positioned such that a distal terminus 221 of the third catheter 220 is distal of the clot material CM. As shown in FIG. 18A, the interventional element 300 and/or the distal element 140 may then be advanced through the third catheter 220 in a low-profile configuration until a distal terminus of the distal element 140 is at or adjacent the distal terminus of the third catheter 220. In some embodiments, the interventional element 300 and distal element 140 may be delivered to the blood vessel V together via the same delivery or individually via separate deliveries. In such embodiments where the interventional element 300 and distal element 140 are delivered separately, the distal element is deployed, e.g., from the third catheter 220, distal of the clot material CM via a first delivery, and then the interventional element 300 is deployed, e.g., from the third catheter 220, distal of or in the clot material CM via a second delivery.

As shown in FIG. 18A, the third catheter 220 may be withdrawn proximally relative to the distal element 140 and the interventional element 300 to release both the distal element 140 and the interventional element 300. This allows the distal element 140 to self-expand into apposition with the vessel wall distal of the clot material CM and interventional element 300, and allows the interventional element 300 to self-expand within the clot material CM. As the interventional element 300 expands, the interventional element 300 engages and/or secures the surrounding clot material CM, and in some embodiments may restore or improve blood flow through the clot material CM by pushing open a blood flow path therethrough (which flow path can extend through the expanded distal member 140). In some embodiments, both the distal element 140 and the interventional element 300 may be expanded distal of the clot material CM such that no portion of the distal element 140 or the interventional element 300 is engaging the clot material CM while the distal element 140 and the interventional element 300 are in the process of expanding toward the vessel wall. In some embodiments, one or both of the distal element 140 and the interventional element 300 are configured to expand into contact with the wall of the vessel V, or the distal element 140, and/or the interventional element 300 may expand to a diameter that is less than that of the blood vessel lumen such that the distal element 140 and/or the interventional element 300 do not engage the entire circumference of the blood vessel wall.

Once the interventional element 300 has been expanded into engagement with the clot material CM (and the distal element 140 has been expanded at a position distal to the clot material CM), the interventional element 300 may grip the clot material CM by virtue of its ability to mechanically interlock with the clot material CM. The distally positioned distal element 140 can block, collect, or otherwise engage with any portions of clot material CM that migrate downstream from the interventional element 300, thereby reducing the risk of additional vessel blockages in distally-located areas of the brain that are more difficult to reach.

Figure 18B:
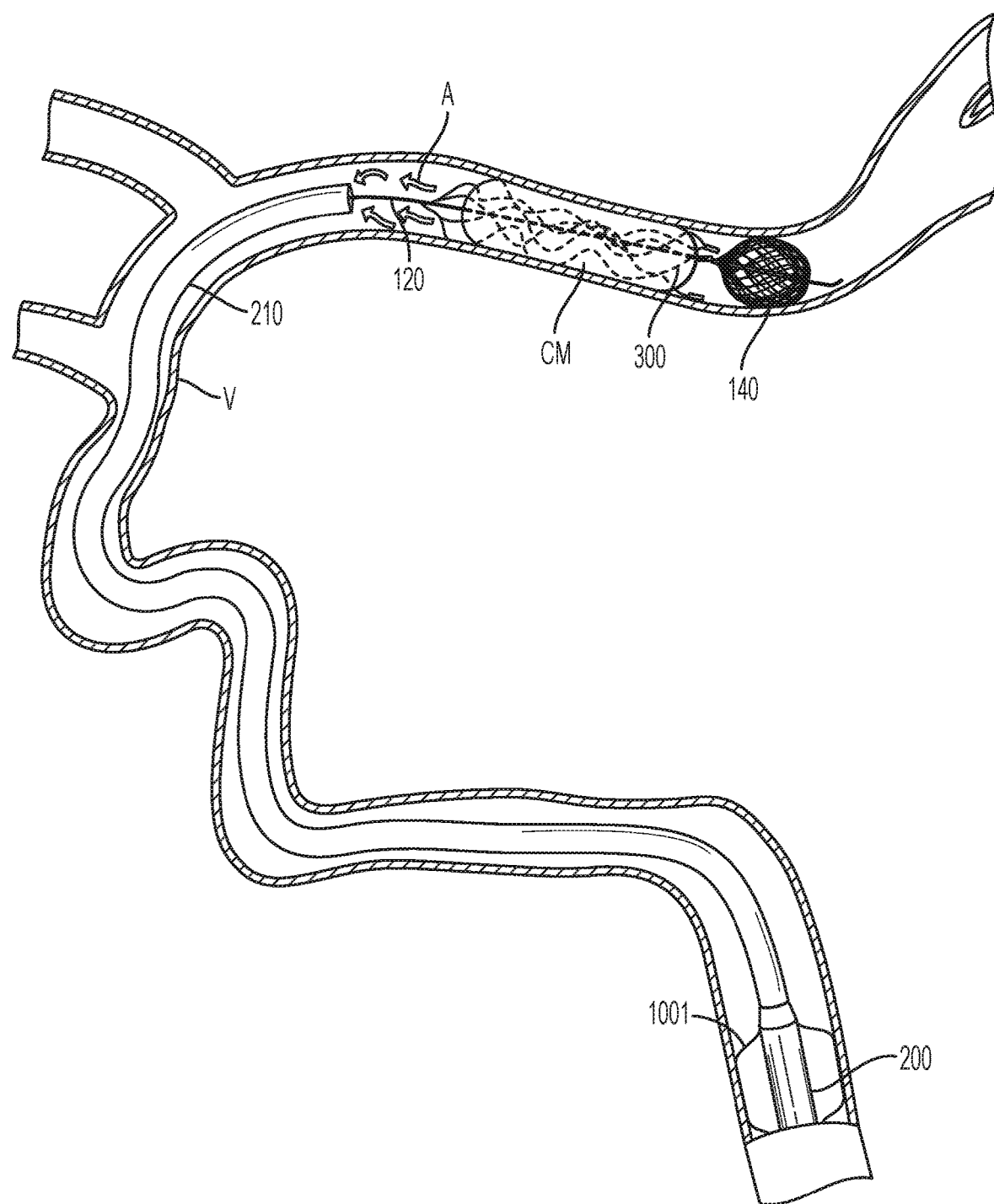

Referring now to FIG. 18B, in some embodiments, aspiration may be applied to the treatment site, e.g., via the second catheter 210. For example, following deployment of the distal element 140 and the interventional element 300, the third catheter 220 can be retracted and removed from the lumen of the second catheter 210. The treatment site can then be aspirated via the second catheter 210, for example via a suction source such as a pump or syringe coupled to a proximal portion of the second catheter 210. In some embodiments, aspiration is applied while the interventional element 300 is retracted into the second catheter 210. Aspiration at this stage can help secure the clot material CM within the second catheter 210 and prevent any dislodged portion of the clot material CM from escaping the second catheter 210 and being released back into the vessel V. In various embodiments, the treatment site can be aspirated continuously before, during, or after retraction of the interventional element 300 into the second catheter 210.

Figure 18C:
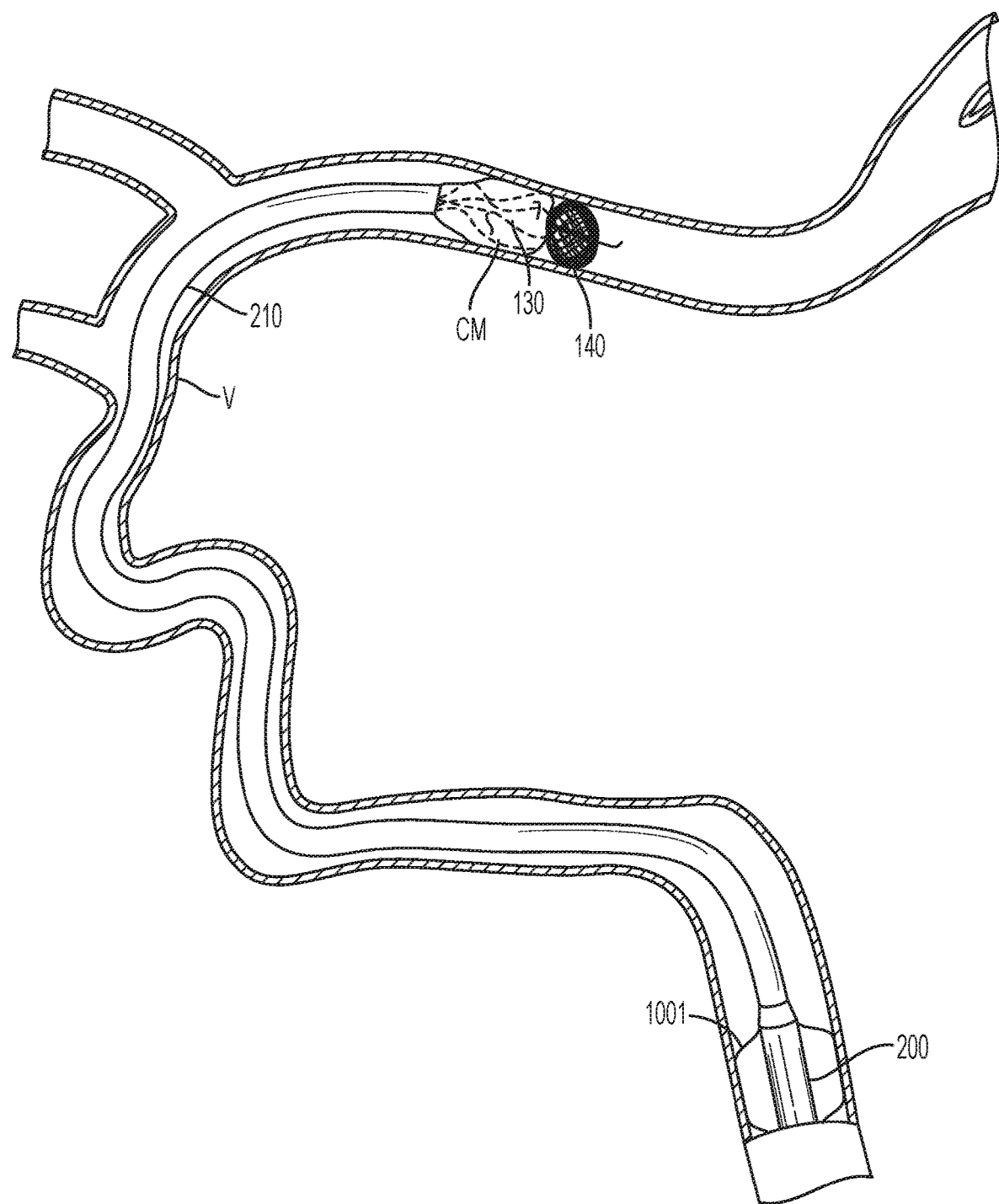
Figure 18D:
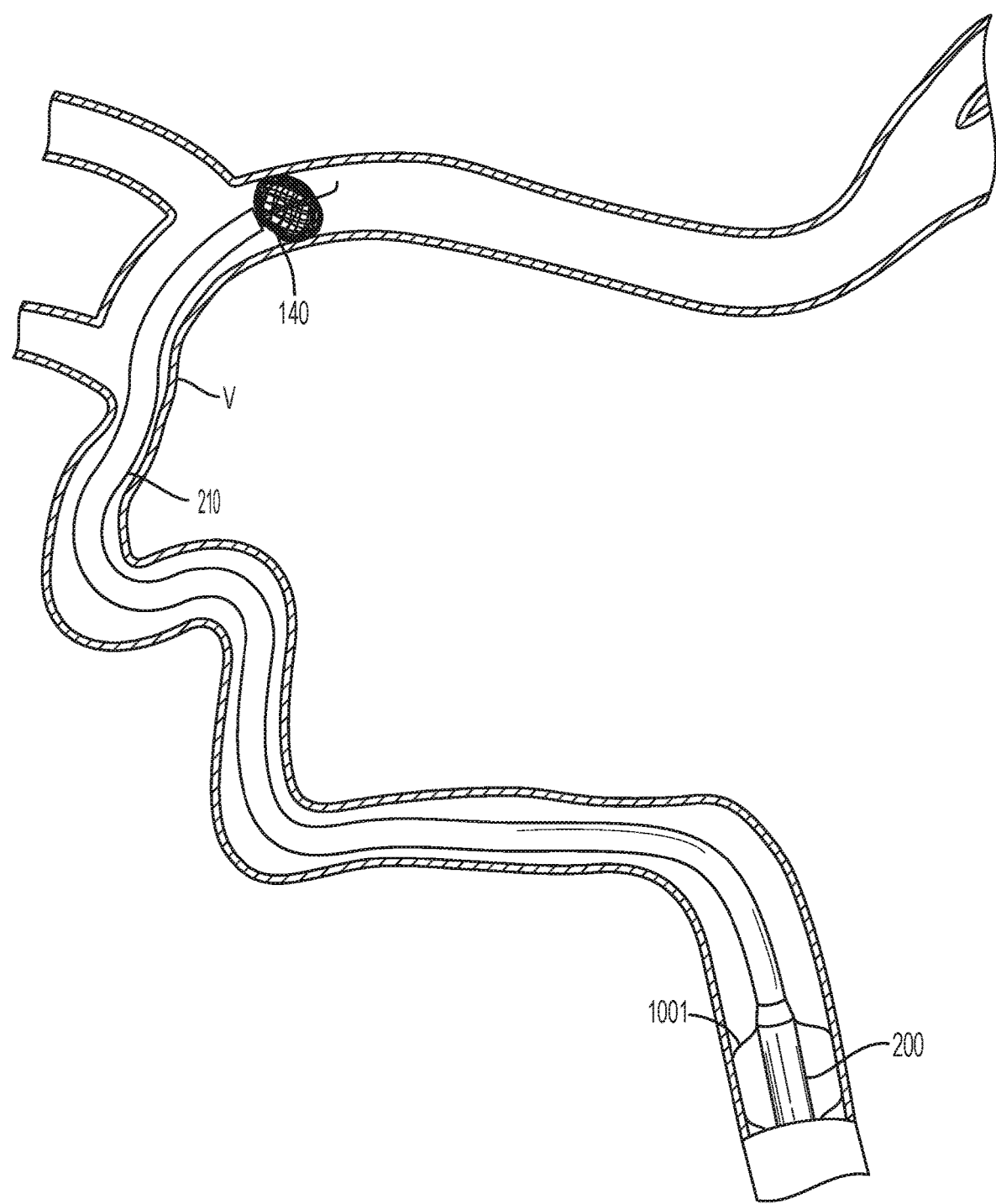

With reference to FIGS. 18C and 18D, while the interventional element 300 is engaged with the clot material CM, the clot material CM can be removed. For example, the interventional element 300, with the clot material CM gripped thereby, and the distally positioned distal element 140 can be retracted proximally (e.g., along with the second catheter 210 and, optionally, the first catheter 200, or into the second catheter 210). When the interventional element 300 and clot material CM are retracted into the second catheter 210, the distal element 140 can help push the clot material CM into the second catheter 210 lumen and subsequently be drawn into the catheter, or left in the expanded configuration, distal of the catheter 210 as a filter/pusher (FIG. 18D). The second catheter 210, distal element 140, interventional element 300, and engaged clot material CM may then be withdrawn from the treatment site, optionally through one or more larger surrounding catheters. During this retraction, any portions of clot material CM that dislodge from the interventional element 300 can be caught by the distal element 140, thereby preventing downstream migration of such clot material CM fragments. As shown in FIG. 18D, the retraction can optionally continue until the distal element 140 abuts the distal end of the second catheter 210 and is retracted into the lumen of the second catheter 210. In some embodiments, the interventional element 300 and clot material CM form a removable, integrated thrombus-device mass.

In some embodiments, the distal element 140 may be used to expand other expandable devices, such as a flow diverter or a stent. In some embodiments, all or a portion of the distal element 140 may be covered with a polymer and used for flow arrest proximally. If the distal half of the distal element 140 was covered, it may be used for flow directed navigation like a sail. This could be helpful in navigating a tortuous arch or other bifurcations.

IV. Example Electrically Enhanced Treatment Devices and Methods of Use

Figure 19A:
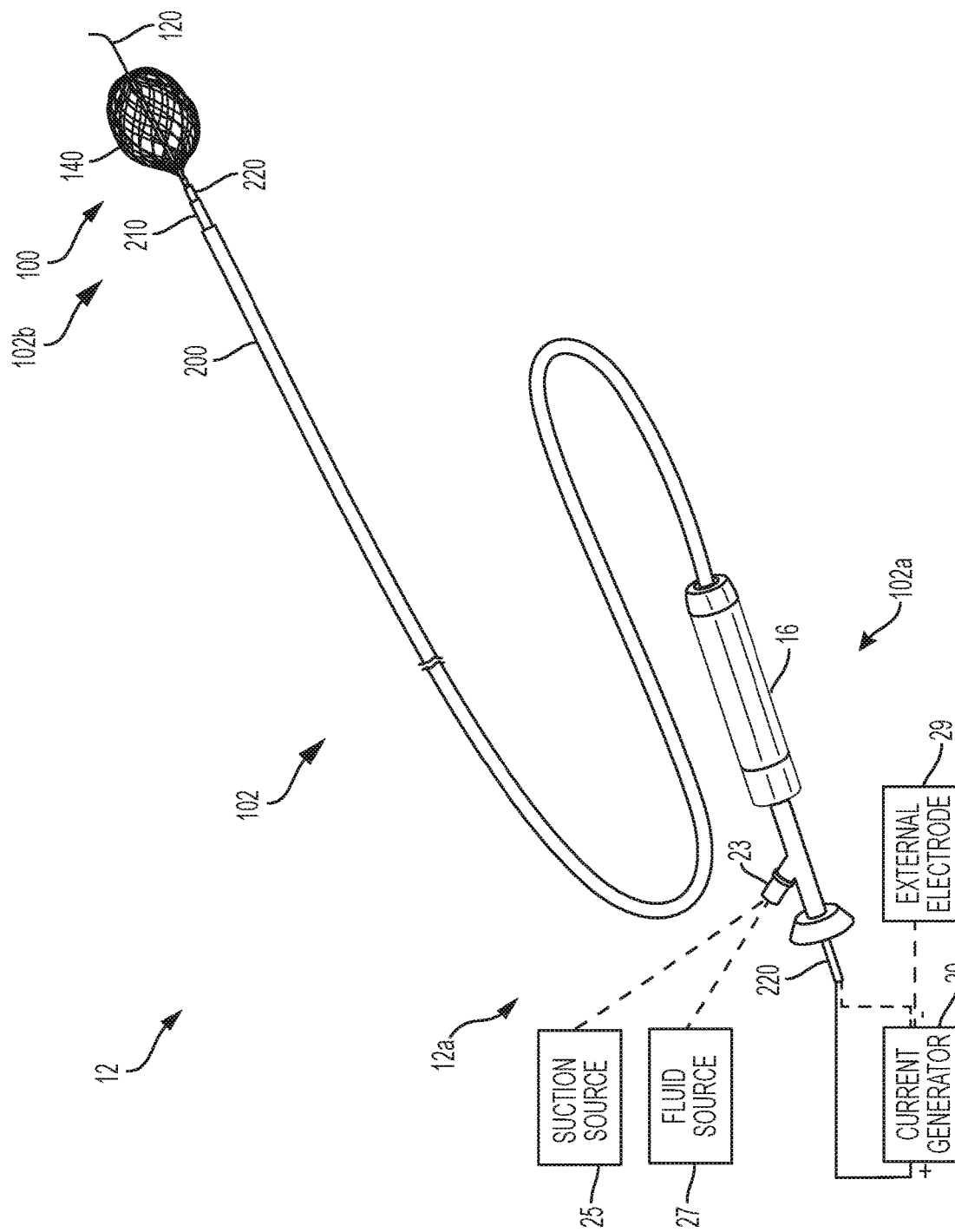
FIG. 19A shows a perspective view of an electrically enhanced treatment system for retrieving material from a body lumen, in accordance with one or more embodiments of the present technology.

FIG. 19A illustrates a view of an electrically enhanced treatment system 12 according to one or more embodiments of the present technology. Several features of the treatment system 12 can be similar to that of the treatment system 10 shown in FIG. 1 and described above. For example, the catheters 200, 210, 220, elongated member 120, and distal element 140 can include some or all of the features described above with respect to FIGS. 1-18E. As shown in FIG. 19A, the treatment system 12 can include a current generator 20 and a treatment device 102 having a proximal portion 102a configured to be coupled to the current generator 20 and a distal portion 102b configured to be intravascularly positioned within a blood vessel (such as an intracranial blood vessel) at a treatment site at or proximate a thrombus. The treatment device 102 includes a distal element 140 at the distal portion 102b, a handle 16 at the proximal portion 102a, and a plurality of coaxially disposed catheters 200, 210, and 220 as described previously. The current generator 20 may be coupled to a proximal portion of one or more of the elongated member 120, the third catheter 220, the second catheter 210, and/or the first catheter 200 to provide an electrically charged environment at the distal portion 102b of the treatment device 102, as described in more detail below. Any of the embodiments or versions of the above-mentioned components that are described herein with reference to the treatment system 10 of FIG. 1 or the treatment system 11 of FIG. 11 can be employed in connection with the treatment system 12 as well.

As described previously herein, the distal element 140 may comprise an expandable mesh having a low-profile state for delivery to a deployment location and an expanded state in which at least a portion of the mesh is configured to be in apposition with the blood vessel wall. The distal element 140 is configured to expand into contact with the blood vessel at the treatment site to anchor and/or stabilize the elongated member 120 or any portion of the treatment system 12 at the desired location. As detailed elsewhere herein, the distal element 140 may also be configured to facilitate removal of the thrombus from the treatment site. In some embodiments, the distal element 140 can be a braided mesh having tapered or closed distal and/or proximal ends, and a central portion having a greater radial dimension than the end(s).

In some embodiments, the treatment system 12 includes a suction source 25 (e.g., a syringe, a pump, etc.) configured to be fluidly coupled (e.g., via a connector 23) to a proximal portion of one or more of the catheters 200, 210, 220 to apply negative pressure therethrough. In some embodiments, the treatment system 12 includes a fluid source 27 (e.g., a fluid reservoir, a syringe, pump, etc.) configured to be fluidly coupled (e.g., via the connector 23) to a proximal portion of one or more of the catheters 200, 210, 220 to supply fluid (e.g., saline, contrast agents, a drug such as a thrombolytic agent, etc.) to the treatment site.

Figure 19B:
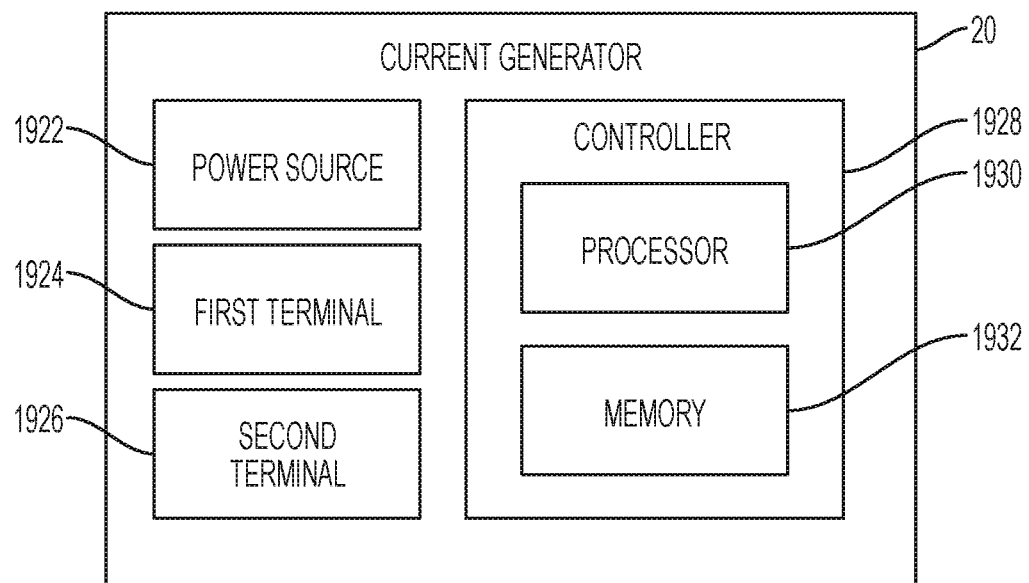
FIGS. 19B and 19C are schematic views of different embodiments of the current generator illustrated in FIG. 19A.
Figure 19C:
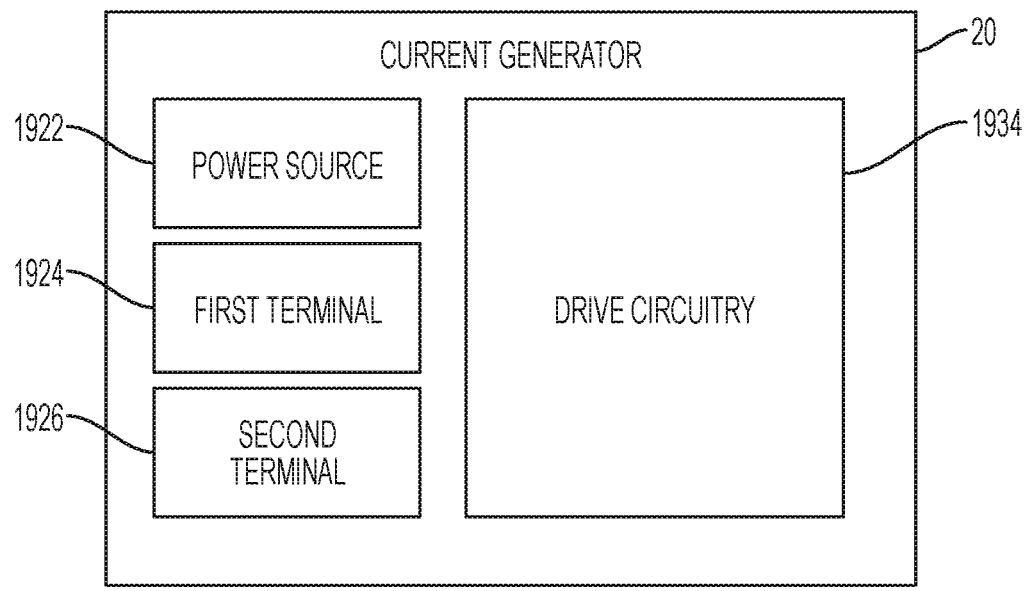

According to some embodiments, the current generator 20 can be configured to output medically useful electric current. FIGS. 19B and 19C are schematic views of different embodiments of the current generator 20. With reference to FIG. 19B, the current generator 20 can include a power source 1922, a first terminal 1924, a second terminal 1926, and a controller 1928. The controller 1928 includes a processor 1930 coupled to a memory 1932 that stores instructions (e.g., in the form of software, code or program instructions executable by the processor or controller) for causing the power source 1922 to deliver electric current according to certain parameters provided by the software, code, etc. The power source 1922 of the current generator 20 may include a direct current power supply, an alternating current power supply, and/or a power supply switchable between a direct current and an alternating current. The current generator 20 can include a suitable controller that can be used to control various parameters of the energy output by the power source or generator, such as intensity, amplitude, duration, frequency, duty cycle, and polarity. For example, the current generator 20 can provide a voltage of about 2 volts to about 28 volts and a current of about 0.5 mA to about 20 mA.

FIG. 19C illustrates another embodiment of the current generator 20, in which the controller 1928 of FIG. 19B is replaced with drive circuitry 1934. In this embodiment, the current generator 20 can include hardwired circuit elements to provide the desired waveform delivery rather than a software-based generator of FIG. 19B. The drive circuitry 1934 can include, for example, analog circuit elements (e.g., resistors, diodes, switches, etc.) that are configured to cause the power source 1922 to deliver electric current via the first and second terminals 1924, 1926 according to the desired parameters. For example, the drive circuitry 1934 can be configured to cause the power source 1922 to deliver periodic waveforms via the first and second terminals 1924, 1926.

As noted above, the current generator 20 may be coupled to a proximal portion of the elongated member 120, and/or a proximal portion of one or more of the catheters 200, 210, 220 (FIG. 19A) to provide an electric current to the distal element 140. For example, in some embodiments, both terminals 1924, 1926 of the current generator 20 are coupled to the elongated member 120 such that the elongated member 120 functions as both a delivery electrode or conductive path (i.e., transmitting current from the current generator 20 to the treatment site) and a return electrode or conductive path (i.e., transmitting current from the treatment site to the current generator 20) (described in greater detail below with reference to FIG. 20B). In other embodiments, the return electrode can be separate from the elongated member 120. For example, the return electrode can be carried by one or more of the catheters 200, 210, 220. In some embodiments, the return electrode can be provided via one or more optional external electrodes 1929 (FIG. 19A), such as a needle puncturing the patient, or a grounding pad applied to the patient's skin. In some embodiments, the return electrode can be an insulated guide wire having an exposed, electrically conductive portion at its distal end.

Figure 20A:
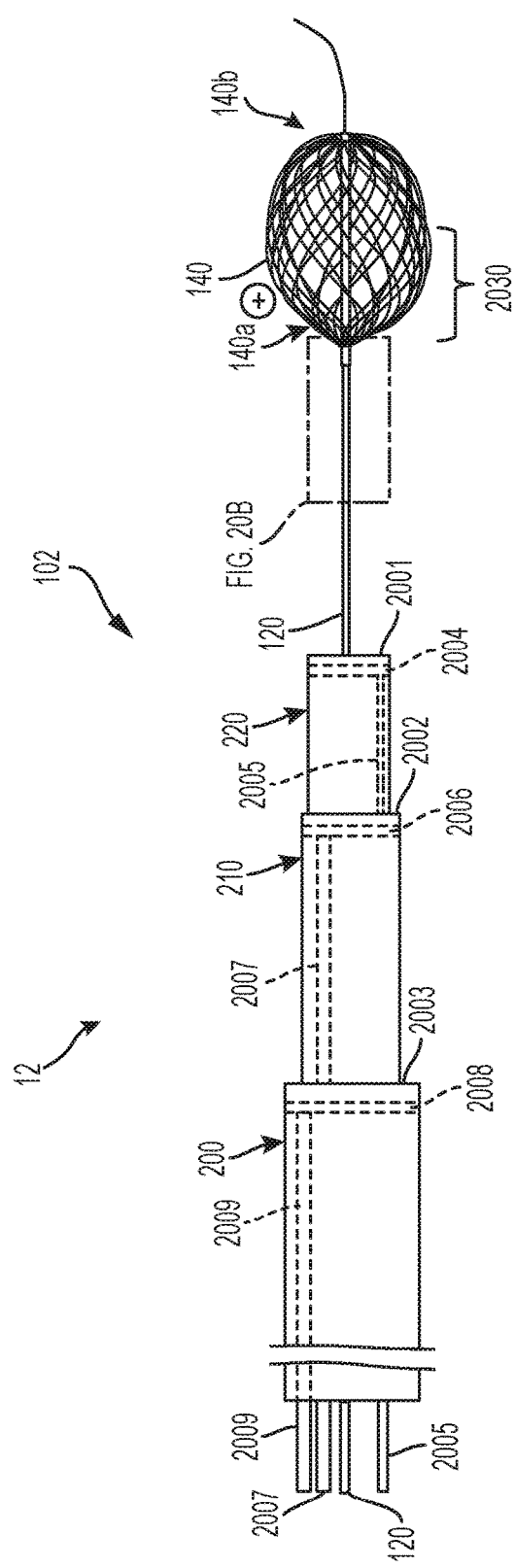
FIG. 20A is a side schematic view of a portion of the treatment system of FIG. 19A.

FIG. 20A is a side schematic view of a portion of the system 12 and treatment device 102 shown in FIG. 19A. The system 12 can include multiple (e.g., two or more), distinct conductive paths or channels for passing electrical current along the system 12. The distal element 140 can serve as one electrode (e.g., the delivery electrode) in electrical communication with a conductive path integrated into the elongated member 120. Another of the conductive paths of the system 12 can be in electrical communication with another electrode (e.g., a return electrode). The various embodiments of the elongated member 120 can be sized for insertion into a bodily lumen, such as a blood vessel, and can be configured to deploy, push and pull a device such as the distal element 140 along the bodily lumen.

Figure 20B:
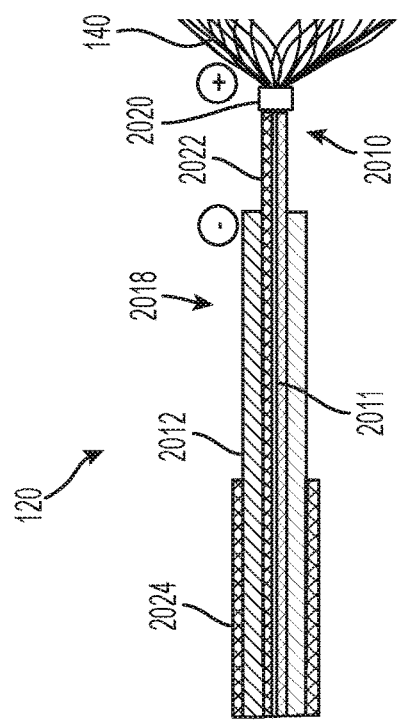
FIG. 20B is a side schematic cross-sectional view of a portion of the treatment system shown in FIG. 20A.

As noted above, the distal element 140 (or a portion thereof) can serve as the delivery electrode and be electrically coupled to a positive terminal of the current generator 20 (FIG. 19A). As shown in FIG. 20B, in some embodiments, the elongated member 120 can include an elongate conductive shaft 2011 (e.g., a pushwire) extending along the length of the elongated member 120. The shaft 2011 can be in electrical communication with the current generator 20 (FIG. 19A) at its proximal end and with the distal element 140 at its distal end. The shaft 2011 can be insulated along at least a portion of its length, with exposed portions permitting electrical communication with the current generator 20 and the distal element 140.

The return electrode(s) can assume a variety of configurations in different embodiments. For example, in some embodiments, the return electrode is an external electrode 29 (FIG. 19A), such as a needle or grounding pad that is applied to a patient's skin. The needle or grounding pad can be coupled via one or more leads to the current generator 20 to complete the electrical circuit. In some embodiments, the return electrode is carried by a surrounding catheter (e.g., third catheter 220, second catheter 210, and/or first catheter 200), as described in more detail elsewhere herein.

According to some embodiments, for example as shown in FIG. 20A, the catheters 200, 210, 220 can each be formed as a generally tubular member extending along and about a central axis and terminating in a respective distal end 2001, 2002, and 2003. According to some embodiments, the first catheter 200 is generally constructed to track over a conventional guidewire in the cervical anatomy and into the cerebral vessels associated with the brain and may also be chosen according to several standard designs that are generally available. Accordingly, the first catheter 200 can have a length that is at least 125 cm long, and more particularly may be between about 125 cm and about 175 cm long. Other designs and dimensions are contemplated.

The second catheter 210 can be sized and configured to slidably extend through the first catheter 200. As noted above, the second catheter 210 can be coupled at a proximal portion to a suction source 25 (FIG. 19A) such as a pump or syringe in order to supply negative pressure to a treatment site. The third catheter 220 can be sized and configured to slidably extend through both the second catheter 210 and the first catheter 200. In some embodiments, the first catheter 200 is a balloon-guide catheter having an inflatable balloon or other expandable member that can be used to anchor the first catheter 200 with respect to a surrounding vessel. As described in more detail below, in operation the first catheter 200 can first be advanced through a vessel and then a balloon can be expanded to anchor the first catheter 200 in place and/or arrest blood flow from areas proximal of the balloon. Next, the second catheter 210 can be advanced through the first catheter 200 until its distal end 2002 extends distally beyond the distal end 2003 of the first catheter 200. The second catheter 210 can be positioned such that its distal end 2002 is adjacent a treatment site (e.g., a site of a blood clot within the vessel). The third catheter 220 may then be advanced through the second catheter 210 until its distal end 2001 extends distally beyond the distal end 2002 of the second catheter 210. The distal element 140 may then be advanced through the third catheter 220 via the elongated member 120 for delivery to the treatment site.

According to some embodiments, an electrode 2004 is provided at a distal end region of the third catheter 220. The electrode 2004 can form an annular ring that extends entirely circumferentially about the central axis of the third catheter 220. Alternatively or in combination, the electrode 2004 can extend less than entirely circumferentially around the third catheter 220. For example, the electrode 2004 may be entirely disposed on one radial side of the central axis. By further example, the electrode 2004 may provide a plurality of discrete, noncontiguous electrode sections about the central axis. Such sections of the electrode 2004 can be in electrical communication with a common conductive path so as to function collectively as a single electrode, or with multiple separate such paths to allow the sections to function independently if desired. The electrode 2004 can be a band, a wire, or a coil embedded in the wall of the third catheter 220. According to some embodiments, the electrode 2004 can be longitudinally separated from the distal end 2001 of the third catheter 220 by a non-conductive portion of the third catheter 220. Alternatively, a distal portion of the electrode 2004 can extend to the distal end 2001 of the third catheter 220, such that the electrode 2004 forms a portion of the distal end 2001. According to some embodiments, an inner surface of the electrode 2004 can be flush with an inner surface of the third catheter 220. Alternatively or in combination, the inner surface of the electrode 2004 can extend more radially inwardly relative to the inner surface of the third catheter 220 (e.g., providing a "step"). Alternatively or in combination, the inner surface of the electrode 2004 can extend less radially inwardly relative to the inner surface of the third catheter 220 (e.g., be recessed into the body). According to some embodiments, the electrode 2004 can be surrounded radially by an outer section of the third catheter 220 to provide insulation from an external environment. In some embodiments, an outer surface of the electrode 2004 can be flush with an outer surface of the third catheter 220 and can provide an exposed, radially outwardly facing electrode surface. In such instances, a radially inner section of the third catheter 220 can provide insulation from the environment within the lumen of the third catheter 220.

The electrode 2004 can include one or more rings, one or more coils or other suitable conductive structures, and can each form at least one surface (e.g., an inner surface or an outer surface) that is exposed and configured for electrical activity or conduction. The electrode 2004 can have a fixed inner diameter or size, or a radially expandable inner diameter or size. In some embodiments, the electrode 2004 is a deposited or "painted" electrode. The electrode can include platinum, platinum alloys (e.g., 92% platinum and 8% tungsten, 90% platinum and 10% iridium), gold, cobalt-chromium, stainless steel, nitinol, and combinations thereof, or any suitable conductive materials, metals or alloys.

In some embodiments, the electrode 2004 can be a separate expandable member coupled to an outer surface of the third catheter 220, for example a braid, stent, or other conductive element coupled to an outer surface of the distal portion of the third catheter 220. In some embodiments, the electrode 2004 can be part of a flow-arrest element such as an expandable braid coupled to an occlusion balloon.

According to some embodiments, the electrode 2004 can be electrically connected to the current generator 20 via a conductive lead 2005. The conductive lead 2005 can extend proximally along or within the wall of the third catheter 220 to or beyond the proximal end of the third catheter 220. The conductive lead 2005 can include more than one conductive path extending within the walls of the third catheter 220. According to some embodiments, the conductive lead 2005 can form a helical coil along or within at least a portion of the third catheter 220. Alternatively or in combination, the conductive lead 2005 can form a braided, woven, or lattice structure along or within at least a portion of the third catheter 220. In some embodiments, the conductive lead 2005 can be a conductive element (e.g., a wire, coil, etc.) wrapped around an external surface of the third catheter 220. In such instances, the conductive lead 2005 can be coated with an insulative material along at least a portion of its length. The insulative material can be, for example, Parylene, PTFE, or other suitable insulative material.

In some embodiments, the second catheter 210 and/or the first catheter 200 can be similarly equipped with corresponding electrodes instead of or in addition to the third catheter 220 or the elongated member 120. For example, the second catheter 210 may include an electrode 2006 disposed at a distal end region of the second catheter 210. The electrode 2006 can be electrically connected to the current generator 20 (FIG. 19A) via a conductive lead 2007 which extends proximally along the second catheter 210. The configuration of the electrode 2006 and the corresponding conductive lead 2007 can be similar to any of the variations described above with respect to the electrode 2004 and the conductive lead 2005 of the first catheter 200.

In some embodiments, the first catheter 200 includes an electrode 2008 disposed at a distal end region of the first catheter 200. The electrode 2008 can be electrically connected to the current generator 20 (FIG. 19A) via a conductive lead 2009 which extends proximally along the first catheter 200. The configuration of the electrode 2008 and the corresponding conductive lead 2009 can be similar to any of the variations described above with respect to the electrode 2004 and the conductive lead 2005 of the third catheter 220.

In various embodiments, the system can include any combination of the electrodes 2004, 2006, and 2008 described above. For example, the system may include the electrode 2004 and the corresponding conductive lead 2005 of the third catheter 220, while the second catheter 210 and the first catheter 200 may be provided with no electrodes or conductive leads therein. In some embodiments, the system may only include the electrode 2006 of the second catheter 210, while the first catheter 200 and the third catheter 220 may be provided with no electrodes or conductive leads therein. In some embodiments, the system may include only the electrode 2008 of the first catheter 200, while the third catheter 220 and the second catheter 210 are provided with no electrodes or corresponding conductive leads therein. In some embodiments, any two of the catheters 200, 210, 220 can be provided with electrodes and corresponding leads, while the remaining catheter may have no electrode or conductive lead therein.

In the configuration illustrated in FIG. 20A, one or more of electrodes 2004, 2006, or 2008 can be coupled to a negative terminal of the current generator 20, while the distal element 140 can be coupled to the positive terminal of the current generator 20 via the elongated member 120. As a result, when voltage is applied at the terminals and the distal element 140 placed in the presence of blood (or any other electrolytic medium), current flows from the distal element 140, through the blood or other media, and to the return electrode. The return electrode may a conductive element carried by one or more of the catheters 200, 210, 220 as described above, or the elongated member 120, or in some embodiments the return electrode can be an external electrode 29 (FIG. 19A) such as needle or grounding pad.

In some embodiments, one or more catheters carrying an electrode can be used without an electrically coupled distal element 140. In various embodiments, the distal element 140 may be omitted altogether, or the distal element 140 may be included but may not be electrically coupled to the current generator 20. In such cases, a catheter-based electrode (e.g., the electrode 2004 carried by the third catheter 220, the electrode 2006 carried by the second catheter 210, or the electrode 2008 carried by the first catheter 200) can function as the delivery electrode, and a separate return electrode can be provided either in the form of another catheter-based electrode (either carried by the same catheter or carried by another catheter) or as an external electrode (e.g., a needle or grounding pad). In instances in which a single catheter carries two electrodes, one electrode may be provided on an exterior surface of the catheter while the other electrode may be provided on an inner surface of the catheter. For example, the second catheter 210 may include a delivery electrode in the form of a conductive band disposed on an inner surface of the catheter 210, in addition to a return electrode in the form of a conductive band disposed on an outer surface of the catheter 210.

As described in more detail in FIG. 20B, in some embodiments the return electrode can be integrated into the elongated member 120 of the treatment system 12, such that the elongated member 120 carries two separate conductive paths along its length. FIG. 20B is a side schematic cross-sectional view of a portion of the treatment system 12 shown in FIG. 20A, in accordance with embodiments of the present technology. As shown in FIG. 20B, the elongated member 120 includes an elongate conductive shaft 2011 and an elongate tubular member 2012 having a lumen through which the shaft 2011 extends. The shaft 2011 has a distal portion 2010, and the tubular member 2012 has a distal portion 2018. Both the shaft 2011 and the tubular member 2012 are electrically conductive along their respective lengths. In some embodiments, the positions of the shaft 2011 and the tubular member 2012 are fixed relative to one another. For example, in some embodiments the shaft 2011 is not slidable or rotatable with respect to the tubular member 2012 such that the elongated member 120 can be pushed or pulled without relative movement between the shaft 2011 and the tubular member 2012 and/or other individual components of the elongated member 120.

In some embodiments, the shaft 2011 can be a solid pushwire, for example a wire made of Nitinol, stainless steel, or other metal or alloy. The shaft 2011 may be thinner than would otherwise be required due to the additional structural column strength provided by the surrounding tubular member 2012. The tubular member 2012 can be a hollow conductive tube, hypotube, braid, coil, or other suitable member(s), or a combination of wire(s), tube(s), braid(s), coil(s), etc. In some embodiments, the tubular member 2012 can be a laser-cut hypotube having a spiral cut pattern (or other pattern of cut voids) formed in its sidewall along at least a portion of its length. The tubular member 2012 can be made of stainless steel (e.g., 304 SS), Nitinol, and/or other alloy. In at least some embodiments, the tubular member 2012 can have a laser cut pattern to achieve the desired mechanical characteristics (e.g., column strength, flexibility, kink-resistance, etc.).

The elongated member 120 can also include an adhesive or a mechanical coupler such as a crimped band or marker band 2020 disposed at the distal end of the elongated member 120, and the marker band 2020 can optionally couple the distal end of the elongated member 120 to the distal element 140. The marker band 2020 can be radiopaque, for example including platinum or other radiopaque material, thereby enabling visualization of the proximal end of the distal element 140 under fluoroscopy. In some embodiments, additional radiopaque markers can be disposed at various locations along the treatment system 12, for example along the shaft 2011, the tubular member 2012, or the distal element 140 (e.g., at the distal end, or along the length, of the distal element 140).

In at least some embodiments, the elongated member 120 also includes a first insulating layer or material 2022 extending between the shaft 2011 and the surrounding tubular member 2012. The first insulating material 2022 can be, for example, PTFE (polytetrafluoroethylene or TEFLON™) or any other suitable electrically insulating coating (e.g., polyimide, oxide, ETFE-based coatings, or any suitable dielectric polymer). In some embodiments, the first insulating material 2022 extends along substantially the entire length of the shaft 2011. In some embodiments, the first insulating material 2022 separates and electrically insulates the shaft 2011 and the tubular member 2012 along the entire length of the tubular member 2012. In some embodiments, the first insulating material 2022 does not cover the proximal-most portion of the shaft 2011, providing an exposed region of the shaft to which the current generator 20 (FIG. 19A) can be electrically coupled. In some embodiments, for example, the first insulating material 2022 terminates proximally at the proximal terminus of the shaft, and the current generator 20 (FIG. 19A) can electrically couple to the shaft 2011 at its proximal terminus, for example using a coaxial connector.

The elongated member 120 can additionally include a second insulating layer or material 2024 surrounding the tubular member 2012 along at least a portion of its length. The second insulating material 2024 can be, for example, PTFE or any other suitable electrically insulative coating (e.g., polyimide, oxide, ETFE based coatings or any suitable dielectric polymer). In some embodiments, the distal portion 2018 of the tubular member 2012 is not covered by the second insulating material 2024, leaving an exposed conductive surface at the distal portion 2018. In some embodiments, the length of the exposed distal portion 2018 of the tubular member 2012 can be at least (or equal to) 1, 2, 3, 4, 5, 6, or more inches. In some embodiments, the length of the exposed distal portion 2018 of the tubular member 2012 can be between at least 1 and 10 inches, or between 2 inches and 8 inches, or between 3 and 7 inches, or between 4 and 6 inches, or about 5 inches. This exposed portion of the distal portion 2018 of the tubular member 2012 provides a return path for current supplied to the delivery electrode (e.g. the entirety or a portion of the distal element 140), as described in more detail below. In some embodiments, the second insulating material 2024 does not cover the proximal-most portion of the tubular member 2012, providing an exposed region of the tubular member 2012 to which the current generator 20 (FIG. 19A) can be electrically coupled. In some embodiments, the second insulating material 2024 proximally terminates at the proximal terminus of the tubular member 2012, and the current generator 20 can electrically couple to the tubular member 2012 at its proximal terminus, for example using a coaxial connector.

In some embodiments, the elongated member 120 also includes a retraction marker in the proximal portion of the tubular member 2012. The retraction marker can be a visible indicator to guide a clinician when proximally retracting an overlying catheter with respect to the elongated member 120. For example, the retraction marker can be positioned such that when a proximal end of the overlying catheter is retracted to be positioned at or near the retraction marker, the distal portion 2018 of the tubular member 2012 is positioned distally beyond a distal end of the catheter. In this position, the exposed distal portion 2018 of the tubular member 2012 is exposed to the surrounding environment (e.g., blood, tissue, etc.), and can serve as a return electrode for the elongated member 120.

The proximal end of the shaft 2011 can be electrically coupled to the positive terminal of the current generator 20, and the proximal end of the tubular member 2012 can be electrically coupled to the negative terminal of the current generator 20. During operation, the treatment system 12 provides an electrical circuit in which current flows from the positive terminal of the current generator 20, distally through the shaft 2011, the distal element 140, and the surrounding media (e.g., blood, tissue, thrombus, etc.) before returning back to the exposed distal portion 2018 of the tubular member, proximally through the tubular member 2012, and back to the negative terminal of the current generator 20 (FIG. 19A).

As noted above, the current generator 20 (FIG. 19A) can include a power source and either a processor coupled to a memory that stores instructions for causing the power source to deliver electric current according to certain parameters, or hardwired circuit elements configured to deliver electric current according to the desired parameters. The current generator 20 may be integrated into the elongated member 120 or may be removably coupled to the elongated member 120, for example via clips, wires, plugs or other suitable connectors. Particular parameters of the energy provided by the current generator 20 are described in more detail elsewhere herein with respect to FIGS. 23A-23E.

In certain embodiments, the polarities of the current generator 20 can be switched, so that the negative terminal is electrically coupled to the shaft 2011 and the positive terminal is electrically coupled to the tubular member 2012. This can be advantageous when, for example, attempting to attract predominantly positively charged material to the distal element 140, or when attempting to break up a clot rather than grasp it with an interventional element. In some embodiments alternating current (AC) signals may be used rather than DC. In certain instances, AC signals may advantageously help break apart a thrombus or other material.

Figure 20C:
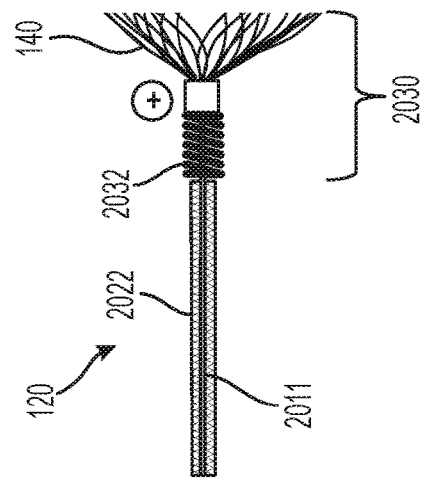
FIG. 20C is a side schematic cross-sectional view of a portion of another embodiment of a treatment system.

As depicted in FIGS. 20A and 20C, the distal element 140 may comprise an attachment portion 2030 that extends only over a portion of the distal element 140 (or the attachment portion 2030 can exclude the distal element 2030 altogether). For example, the attachment portion 2030 may extend only over a proximal portion (e.g., a proximal face, a proximal half, a proximal third, proximal quarter, etc.) of the distal element 140. The attachment portion 2030 of the distal element 140 may be configured to interlock, capture, interface with, and/or engage a thrombus. The portion of the distal element 140 outside the attachment portion may or may not contact thrombotic material in use, but is configured to perform a function that renders it ineffective or less effective than the attachment portion for interlocking, capturing, and/or engaging with a thrombus. In some embodiments, such as that shown in FIG. 20A, a distal terminus of the attachment portion is proximal of the distal terminus of the distal element 140 (i.e., the attachment portion is spaced apart from the distal terminus of the distal element 140), and a proximal terminus of the attachment portion 2030 is at or adjacent to the band 2020.

In some embodiments, the "non-attachment portion" of the distal element 140 (e.g., the entire distal element 140 other than the attachment portion) can be coated with a non-conductive or insulative material (e.g., Parylene, PTFE, or other suitable non-conductive coating) such that the coated region is not in electrical contact with the surrounding media (e.g., blood). As a result, the current carried by the elongated member 120 to the distal element 140 is only exposed to the surrounding media along the attachment portion 2030 of the distal element 140. This can advantageously concentrate the electrically enhanced attachment effect along the attachment portion 2030 of the distal element 140, where it is most useful, and thereby combine both mechanical contact/interlocking and the electrical enhancement provided by the delivered electrical signal. In some embodiments, a distal portion 140b of the distal element 140 (e.g. distal of the attachment portion 2030) may likewise be coated with a non-conductive material (e.g., Parylene, PTFE, or other suitable non-conductive coating), leaving only a proximal region or the attachment portion 2030 of the distal element 140 having an exposed conductive surface.

In some embodiments, the distal element 140 may include a conductive material positioned on some or all of its outer surface. The conductive material, for example, can be gold and/or another suitable conductor that has a conductivity greater than (or a resistivity less than) that of the material comprising the distal element 140. The conductive material may be applied to the distal element 140 via electrochemical deposition, sputtering, vapor deposition, dip-coating, and/or other suitable means. In various embodiments, the coating may be disposed only at the outwardly facing portion of the filaments, only an inwardly facing portion of the filaments, only on one of the side portions or on any combination of the surface portions.

In some embodiments, a conductive coating (e.g., disposed over the attachment portion 2030) or insulative coating (e.g., disposed over non-attachment portions of the distal element 140) can be provided with varying thickness or concentrations. For example, in some embodiments the conductive coating is provided according to a gradient, in which the concentration or thickness of conductive material is greatest near a central region (or a proximal region) of the attachment portion 2030, and the concentration or thickness of conductive material gradually decreases towards the edges of the attachment portion 2030. As electrical current tends to focus in more conductive portions of the distal element 140, such gradients can increase charge density in desired regions of the distal element 140 (e.g., providing increased charge density in a central region (or a proximal region) of the attachment portion 2030).

In some aspects of the present technology, the conductive material is disposed only on the attachment portion 2030 of the distal element 140 while the distal portion 140b of the distal element 140 is exposed. Because the conductive material has a much lower resistance than the underlying material comprising the distal element 140, current delivered to the distal element 140 concentrates along the attachment portion 2030. In several of such embodiments, the conductive material may be disposed only on the outer portion of the strut surface along the attachment portion 2030. In other embodiments, the conductive material may be disposed on all or a portion of the filament surface along all or a portion of the length of distal element 140.

As illustrated in FIG. 20C, some or all of the attachment portion 2030 can be located on (or formed by) the elongated member 120, e.g. in the form of a coil 2032 disposed at a position proximal to the marker band 2020, and proximal to the distal element 140. The coil 2032 can be electrically conductive, for example being made of metal (e.g., stainless steel (e.g., 304 SS), Nitinol, and/or other alloy) or other suitable conductive material. In some embodiments, the coil 2032 is a separate element mounted over the shaft 2011 of the elongated member 120. In other embodiments, shaft 2011 itself can form a coiled shape to provide the coil 2032. In some embodiments, rather than a helical coil 2032, other shapes and structures can be provided in the same location, for example an undulating curve, a series of bent portions, a spiral-cut or slotted-cut tube, or other suitable shape or structure. The coil 2032 (or other suitable structure) can provide increased electrode surface area in this region. When current is applied to the shaft 2011, the increased surface area provided by the coil 2032 can enhance the ability of the electrode to contact, engage and/or grip the clot material CM, thereby increasing electrostatic attachment. As a result, in some embodiments, the attachment portion 2030 extends proximally of the distal element 140 (and/or excludes the distal element 140) and can include the coil 2032 and a portion of the elongated member 120.

In some embodiments, individual filaments or groups of filaments of the distal element 140 can be individually electrically addressable. For example, a first group of filaments can be electrically addressable, for example being coupled to a first terminal of a power supply, while a second group of filaments can be separately electrically addressable, for example being coupled to a second terminal of a power supply. Within the distal element 140, the first and second groups of filaments can have insulated and non-insulated portions such that an exposed, conductive portion of the first group is not in direct contact with exposed, conductive portions of the second group of filaments. For example, the first group of filaments can be coated with insulative material along the proximal portion 140a of the distal element 140 and exposed (or coated with conductive material) along the distal portion 140b of the distal element 140. The second group of filaments can have the opposite configuration, in which they are coated with insulative material along the distal portion 140b of the distal element 140 and exposed (or coated with conductive material) along the proximal portion 140a of the distal element 140. In operation, when current is supplied and the distal element 140 is in the presence of electrolytic media, one group of filaments can serve as the delivery electrode (e.g., having a positive electrical charge) and the other group of filaments can serve as the return electrode (e.g., having a negative electrical charge). In some embodiments, there may be three, four, five, six, or more separately electrically addressable filaments or groups of filaments. Such filaments can extend proximally along the length of the elongated member 120, for example extending along a distal portion of the elongated member 120 to provide separately addressable electrodes in that region.

In operation, delivery of electrical current to the distal element 140 can enhance retrieval of clot material. For example, referring back to FIGS. 10A-10E, the illustrated method can be electrically enhanced using a treatment system 12 as described above with respect to FIGS. 19A-20C, in which a current generator 20 is electrically coupled to one or more elements of the treatment system 12. For example, the current generator 20 can be electrically coupled to the proximal end of the elongated member 120 and configured to deliver current to the distal element 140 (or to the attachment portion 2030 thereof, or to the attachment portion 2030 instead of the distal element 140) before or after the distal element 140 has been released from the third catheter 220 into the blood vessel and/or expanded into or adjacent to the clot material CM as shown in FIG. 10C. The distal element 140 can be left in place or manipulated within the vessel V for a desired time period while the electrical signal is being delivered. The positively charged distal element 140/attachment portion 2030 can attract negatively charged constituents of the clot material CM, thereby enhancing the grip of the distal element 140 and/or attachment portion 2030 on the clot material CM. This allows the distal element 140 to be used to retrieve the clot material CM and push (and/or aspirate) it into the first or second catheter 200/210, with reduced risk of losing grip on the thrombus or a piece thereof, which can migrate downstream and cause additional vessel blockages in areas of the brain that are more difficult to reach.

As shown in FIG. 10D, aspiration may be applied to the treatment site via the second catheter 210. For example, following deployment of the distal element 140, the first catheter 200 can be retracted and removed from the lumen of the second catheter 210. The treatment site can then be aspirated via the second catheter 210, for example via a suction source such as a pump or syringe coupled to a proximal portion of the second catheter 210. In some embodiments, following expansion of the distal element 140, the treatment site is aspirated concurrently with supplying electrical energy to the distal element 140 (or to the attachment portion 2030 thereof, or to the attachment portion 2030 instead of the distal element 140) via the current generator 20. By combining aspiration with the application of electrical energy, any newly formed clots (e.g., any clots formed that are attributable at least in part to the application of electrical energy), or any clot pieces that are broken loose during the procedure, can be pulled into the second catheter 210, thereby preventing any such clots from being released downstream of the treatment site. As a result, concurrent aspiration may permit the use of higher power or current levels delivered to the distal element 140 without risking deleterious effects of new clot formation. Additionally, aspiration can capture any gas bubbles formed along the distal element 140 or marker band 2020 (FIG. 20A) during application of electrical energy to the distal element 140, which can improve patient safety during the procedure.

In some embodiments, aspiration is applied while the distal element 140 is retracted into the second catheter 210. During retraction, the proximal face of the distal element 140 can engage with the clot material CM and urge it proximally towards the distal end of the second catheter 210. Aspiration at this stage can help secure the clot material CM within the second catheter 210 and prevent any dislodged portion of the clot material CM from escaping the second catheter 210 and being released back into the vessel V. In various embodiments, the treatment site can be aspirated continuously before, during, or after delivering electrical signals to the distal element 140 (and/or attachment portion 2030) as well as before, during, or after retraction of the distal element 140 into the second catheter 210.

At least while the distal element 140 is deployed and engaging the thrombus CM, electric current may be delivered to the distal element 140 (and/or attachment portion 2030) to positively charge the distal element 140 or attachment portion 2030, thereby enhancing clot adhesion to the distal element 140 or attachment portion 2030. In some cases, electrically enhanced clot adhesion can be improved in the absence of blood flow. As such, it may be especially beneficial to arrest blood flow (e.g., via the balloon 1001 of the first catheter 200, or a flow arrest element on the second catheter 210) while the distal element 140 or attachment portion 2030 is charged, and while withdrawing the distal element 140 and thrombus CM proximally. Instead of or in addition to such blood flow arrest, a flow of saline may be provided from the fluid source 27 toward the distal element 140 via the second catheter 210 and/or first catheter 200.

With reference to FIG. 10E, while the distal element 140 is engaged with the clot material CM, the clot material CM can be removed. For example, the distal element 140, with the clot material CM gripped or abutted thereby, can be retracted proximally (for example, into the second catheter 210 or along with the second catheter 210 and, optionally, the first catheter 200). The second catheter 210, distal element 140, and associated clot material CM may then be withdrawn from the patient, optionally through one or more larger surrounding catheters such as the first catheter 200.

During this retraction, the distal element 140 and/or attachment portion 2030 can grip the clot material CM electrically and/or electrostatically, e.g., via the application of current from a current generator as discussed herein. (As used herein with reference to gripping or retrieving thrombus or other vascular/luminal material, or to apparatus for this purpose, "electrical" and its derivatives will be understood to include "electrostatic" and its derivatives.) Accordingly, the distal element 140 and/or attachment portion 2030 can maintain an enhanced or electrically and/or electrostatically enhanced grip on the clot material CM during retraction. In other embodiments, the current generator 20 may cease delivery of electrical signals to the distal element 140 and/or attachment portion 2030 prior to retraction of the distal element 140 with respect to the vessel V. In some embodiments, the distal element 140 and clot material CM form a removable, integrated thrombus-device mass wherein the connection of the thrombus to the device is electrically enhanced, e.g. via the application of current as discussed herein.

In FIG. 10E, the clot material CM has been moved to at least partially enter the second catheter 210. In some embodiments, the clot material CM can substantially block the lumen of the catheter 210, thereby creating a "corking" effect that may be noticeable to a clinician supplying negative pressure to the catheter 210 as noted previously. In some embodiments, the current generator 20 can continue to supply electrical signals to the distal element 140 and the return electrode during retraction, while in other embodiments the current generator 20 can cease supplying electrical signals during retraction of the catheter 210 and the clot material CM.

In some instances, instead of or in addition to delivery of electrical current to the distal element 140 or attachment portion 2030, electrical current can be delivered to an electrode carried by one or more of the catheters (e.g., the second catheter 210). For example, electrical signals can be supplied to the second catheter 210 via the current generator 20 to electrically charge a distal portion of the catheter 210. For example, as described above with respect to FIG. 20A, in some embodiments the second catheter 210 can include an electrode disposed at its distal portion. The electrode can be any electrically conductive element, for example a conductive band extending around an inner or outer surface of the catheter 210, a stent engaged with an inner surface of the second catheter 210, etc. The first electrode can be electrically coupled to a conductive lead that extends proximally along the catheter 210 and is coupled at its proximal end to the positive terminal of current generator 20. The conductive lead can be, for example, a wire, coil, or other conductive element carried by and/or coupled to the catheter 210. In some embodiments, the conductive lead is embedded within a wall of the second catheter 210. In other embodiments, the conductive lead is disposed along an external surface of the catheter 210 (e.g., helically wound around the outer surface of the catheter 210 along its length). The conductive lead can be covered with insulative material along a portion of its length, for example Parylene, PTFE, or other suitable insulative coating.

The negative terminal of the current generator 20 can be coupled to a return electrode to complete the electrical circuit with the first electrode disposed on the catheter 210. In some embodiments, the return electrode can be an external electrode (e.g., a needle or a grounding pad coupled to the patient's skin). In other embodiments, the return electrode can be carried by a separate catheter. In some embodiments, the return electrode can be carried by the catheter 210 at a position spaced apart from the first electrode. For example, the first electrode can be a conductive element such as a band or ring disposed at a position spaced apart from the first electrode. In some embodiments, the first electrode may be exposed along a radially inner surface of the catheter 210, while the return electrode may be exposed along a radially outer surface of the catheter 210. In some embodiments, the return electrode can be a separate expandable member coupled to an outer surface of the catheter 210 (e.g., a balloon or other expandable member having a conductive element such as a metallic braid therein).

In some methods of the present technology, a guidewire (not shown) may be advanced to the treatment site and pushed through the clot material CM until a distal portion of the guidewire is distal of the clot material CM. The guidewire may be advanced through one or more of the catheters 200, 210, 220 and/or one or more of the catheters 200, 210, 220 may be advanced over the guidewire. The guidewire may be insulated along at least a portion of its length (e.g., with Parylene, PTFE, etc.), with exposed portions permitting electrical communication with the current generator 20 and the distal element 140. For example, in some embodiments a distal portion of the guidewire may be exposed, and the guidewire may be positioned at the treatment site such that the exposed portion of the guidewire is distal of the clot material CM. A proximal end of the guidewire may be coupled to the current generator 20 such that the exposed portion of the guidewire functions as a return electrode. In some embodiments, the guidewire may be coupled to the positive terminal of the power source and the exposed portion functions as a delivery electrode. The guidewire may be used as a delivery or return electrode with any delivery or return electrode carried by any component of the treatment system (e.g., one or more of the first-third catheters 200, 210, 220, the distal element 140, etc.).

Figure 22:
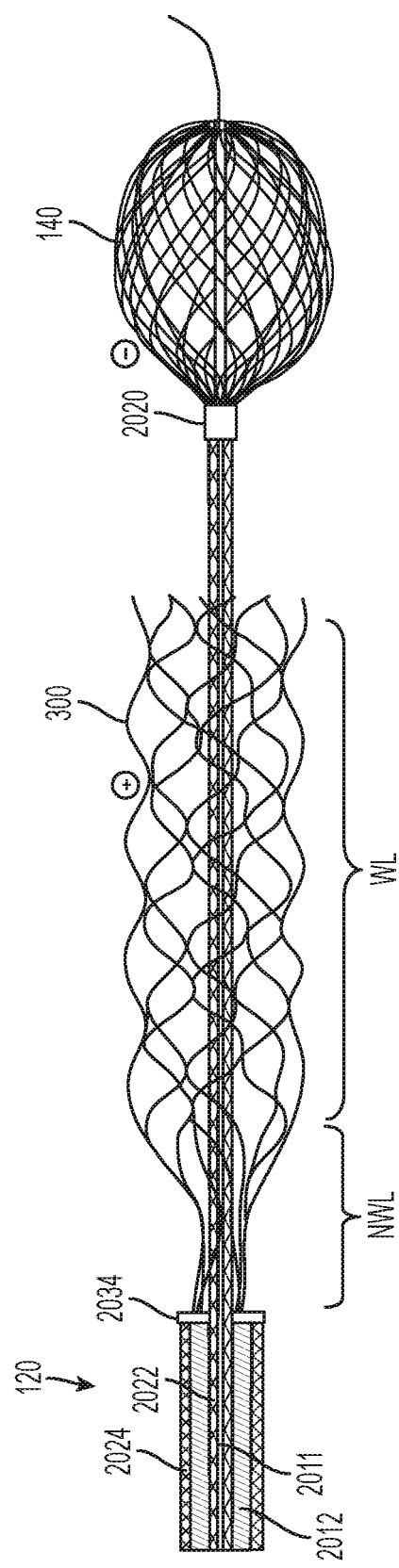
FIG. 22 is a side schematic view of a portion of the treatment system shown in FIG. 21.

FIGS. 21-22 illustrate a treatment system 13 that includes a distal element 140, an interventional element 300, and a current generator 20 to provide an electrical charge to selected components of the system 13. The distal element 140 (or an attachment portion 2030 thereof) and the interventional element 300 can serve as electrodes in operation of the system 13, either of opposing polarity, with the interventional element 300 positively charged and the distal element 140 employed as a negatively charged return electrode (or vice versa), or of common polarity, with both the interventional element 300 and the distal element positively charged and some other component (e.g. the second catheter 210, or any other suitable component) providing a negatively charged return electrode. Alternatively, the interventional element 300 can be electrically neutral or isolated from the rest of the treatment system 13. Several features of the treatment system 13 can be similar to the treatment system 11 shown in FIG. 11 and described above. For example, the catheters 200, 210, 220, elongated member 120, distal element 200, and interventional element 300 can include some or all of the features described above with respect to FIGS. 1-18E. As shown in FIG. 22, both the distal element 140 and the interventional element 300 are coupled to a distal portion of the elongated member 120. The elongated member 120 can be coupled to a current generator at its proximal end (not shown) as described previously with respect to FIG. 20A. The distal element 140 can be in electrical communication with the conductive shaft 2011 which is surrounded by the insulative material 2022 along its length. Any of the embodiments or versions of the above-mentioned components that are described herein with reference to the treatment system 10 of FIG. 1, the treatment system 11 of FIG. 11, or the treatment system 12 of FIG. 19A can be used with the treatment system 13 as well.

With continued reference to FIG. 22, the conductive tubular member 2012 extends over the shaft 2011 and is itself covered with an insulative material 2024 along its length. As illustrated, the shaft 2011 extends distally beyond the distal end of the tubular member 2012. In some embodiments the shaft 2011 is not slidable or rotatable with respect to the tubular member 2012 such that the elongated member 120 can be pushed or pulled without relative movement between the shaft 2011 and the tubular member 2012 and/or other individual components of the elongated member 120.

The elongated member 120 can also include an adhesive or a mechanical coupler such as a crimped band or marker band 2020 disposed at the distal end of the elongated member 120 as described previously. Additionally, the elongated member 120 can include a second marker band 2034 (or other suitable mechanical coupler or adhesive) disposed at the distal end of the tubular member 2012. The second band 2034 can couple the distal end of the tubular member 2012 with a proximal end of an interventional element 300 such that the interventional element 300 is in electrical communication with the second band 2034 and with the tubular member 2012.

As described previously herein, the interventional element 300 can be generally tubular (e.g., cylindrical), and the proximal portion of the interventional element 300 can taper proximally to the proximal end, here coupled to the second band 2034. In various embodiments, the interventional element 300 can take any number of forms, for example a removal device, a thrombectomy device, or other suitable medical device. For example, in some embodiments the interventional element 300 may be a stent and/or stent retriever, such as Medtronic's Solitaire™ Revascularization Device, Stryker Neurovascular's Trevo® ProVue™ Stentriever, or other suitable devices. In some embodiments, the interventional element 300 may be a coiled wire, a weave, and/or a braid formed of a plurality of braided filaments. In some embodiments, the interventional element 300 is a mesh structure (e.g., a braid, a stent, etc.) formed of a superelastic material (e.g., Nitinol) or other resilient or self-expanding material configured to self-expand when released from a surrounding catheter. The mesh structure may include a plurality of struts and open spaces between the struts. In some embodiments, the struts and spaces may be situated along the longitudinal direction of the interventional element 300, the radial direction, or both.

As depicted in FIG. 22, the interventional element 300 may comprise a working length WL portion and a non-working length NWL portion. The portion of the interventional element 300 in the working length WL may be configured to interlock, capture, and/or engage a thrombus. The portion of the interventional element 300 in the non-working length NWL may contact thrombotic material in use, but is configured to perform a function that renders it ineffective or less effective than the working length WL portion for interlocking, capturing, and/or engaging with a thrombus. In some embodiments, such as that shown in FIG. 22, a distal terminus of the working length WL portion is proximal of the distal terminus of the interventional element 300 (i.e., the working length WL portion is spaced apart from the distal terminus of the interventional element 300), and the non-working length NWL portion is disposed between the working length WL and the band 2034 and/or the distal end of the tubular member 2012.

In some embodiments where the interventional element 300 serves as an electrode, the non-working length NWL portion of the interventional element 300 can be coated with a non-conductive or insulative material (e.g., Parylene, PTFE, or other suitable non-conductive coating) such that the coated region is not in electrical contact with the surrounding media (e.g., blood). As a result, the current carried by the tubular member 2012 to the interventional element 300 is only exposed to the surrounding media along the working length WL portion of the interventional element 300. This can advantageously concentrate the electrically enhanced attachment effect along the working length WL of the interventional element 300, where it is most useful, and thereby combine both the mechanical interlocking provided by the working length WL and the electrical enhancement provided by the delivered electrical signal. In some embodiments, a distal region of the interventional element 300 (e.g. distal of the working length WL) may likewise be coated with a non-conductive material (e.g., Parylene, PTFE, or other suitable non-conductive coating), leaving only a central portion or the working length WL of the interventional element 300 having an exposed conductive surface.

In some embodiments, the interventional element 300 may include an additional conductive material positioned on some or all of its outer surface. The conductive material, for example, can be gold and/or another suitable conductor that has a conductivity greater than (or a resistivity less than) that of the material comprising the interventional element 300. The conductive material may be applied to the interventional element 300 via electrochemical deposition, sputtering, vapor deposition, dip-coating, and/or other suitable means. In some embodiments, the conductive material may be disposed only on an outwardly facing surface, on an inwardly facing surface, on one or more of the side surfaces of the struts, or on any combination of surface portions.

In some embodiments, a first portion of the interventional element 300 is covered by a conductive material and a second portion of the interventional element 300 is covered by an insulative or dielectric material (e.g., Parylene). In some embodiments, the working length WL portion of the interventional element 300 may be covered by a conductive material while the non-working length NWL portion is covered by an insulative material. In some embodiments, a conductive material may be disposed on all or a portion of the strut surface along all or a portion of the length of the interventional element 300, and the insulative material may be disposed on those portions of the strut surface and/or working length not covered by the conductive material.

The proximal end of the shaft 2011 can be electrically coupled to the negative terminal of the current generator 20, and the proximal end of the tubular member 2012 can be electrically coupled to the positive terminal of the current generator 20. During operation, the treatment system 13 provides an electrical circuit in which current flows from the positive terminal of the current generator 20, distally through the tubular member 2012, the interventional element 300, and the surrounding media (e.g., blood, tissue, thrombus, etc.) before returning back to the distal element 140 and proximally along the tubular member 2012, and back to the negative terminal of the current generator 20 (FIG. 21).

In some embodiments, the distal element 140 and the interventional element 300 can be delivered using separate shafts, pushwires, or other elongated members. For example, the distal element 140 may be coupled to a distal portion of the elongated member 120, while the interventional element 300 is coupled to a distal portion of a separate elongated member or shaft (e.g. a shaft having an internal lumen (such as the elongated shaft 170) in which the elongated member 120 is received). The two elongated members may be separately advanceable through a surrounding catheter, allowing the distal element 140 and the interventional element 300 to be moved rotationally and longitudinally with respect to one another. Each of the elongated members can be separately coupled to a terminal of the current generator 20, thereby allowing the interventional element 300 to serve as a delivery electrode and the distal element 140 to serve as a return electrode, or vice versa.

In operation, delivery of electrical current to the interventional element 300 and the distal element 140 (and/or an attachment portion 2030 thereof) can enhance retrieval of clot material. For example, referring back to FIGS. 18A-18D, the illustrated method can be electrically enhanced using a treatment system as described above with respect to FIG. 22, in which a current generator 20 is electrically coupled to one or more elements of the treatment system 13. For example, the current generator 20 can be electrically coupled to the proximal end of the elongated member 120 and configured to deliver current to the interventional element 300 and distal element 140 (and/or an attachment portion 2030 thereof) before or after the interventional element 300 and/or the distal element 140 has been released from the third catheter 220 into the blood vessel and/or expanded into or adjacent to the clot material CM as shown in FIG. 18A. The interventional element 300 and the distal element 140 can be left in place or manipulated within the vessel V for a desired time period while the electrical signal is being delivered. The positively charged interventional element 300 (and, where so employed, the positively charged distal element 140 as well) can attract negatively charged constituents of the clot material CM, thereby enhancing the grip of the interventional element 300 (and, when positively charged, the distal element 140) on the clot material CM. This allows the interventional element 300 (and possibly the distal element 140) to be used to retrieve the clot material CM with reduced risk of losing grip on the thrombus or a piece thereof, which can migrate downstream and cause additional vessel blockages in areas of the brain that are more difficult to reach. Additionally, the distal element 140 can serve as an additional filter (whose function is electrostatically enhanced when the distal element is positively charged) to stop any dislodged piece of thrombus or clot material CM from migrating downstream with respect to the interventional element 300.

As shown in FIG. 18B, aspiration may be applied to the treatment site via the second catheter 210. For example, following deployment of the interventional element 300 and the distal element 140, the first catheter 200 can be retracted and removed from the lumen of the second catheter 210. The treatment site can then be aspirated via the second catheter 210, for example via a suction source such as a pump or syringe coupled to a proximal portion of the second catheter 210. In some embodiments, following expansion of the interventional element 300 and the distal element 140, the treatment site is aspirated concurrently with supplying electrical energy to the interventional element 300 (and/or distal element 140, either at the same or opposing polarity as the interventional element 300) via the current generator 20. By combining aspiration with the application of electrical energy, any newly formed clots (e.g., any clots formed that are attributable at least in part to the application of electrical energy), or any clot pieces that are broken loose during the procedure, can be pulled into the second catheter 210, thereby preventing any such clots from being released downstream of the treatment site. As a result, concurrent aspiration may permit the use of higher power or current levels delivered to the interventional element 300 without risking deleterious effects of new clot formation. Additionally, aspiration can capture any gas bubbles formed along the interventional element 300 or marker band 2034 (FIG. 22) during application of electrical energy to the interventional element 300, which can improve patient safety during the procedure.

In some embodiments, aspiration is applied while the interventional element 300 and the distal element 140 are retracted into the second catheter 210. During retraction, the proximal face of the distal element 140 (and/or the engagement portion 2030) can engage with the clot material CM and urge it proximally towards the distal end of the second catheter 210. Aspiration at this stage can help secure the clot material CM within the second catheter 210 and prevent any dislodged portion of the clot material CM from escaping the second catheter 210 and being released back into the vessel V. In various embodiments, the treatment site can be aspirated continuously before, during, or after delivering electrical signals to the interventional element 300 (and/or distal element 140) as well as before, during, or after retraction of the interventional element 300 into the second catheter 210.

At least while the interventional element 300 is deployed and engaging the thrombus CM, electric current may be delivered to the interventional element 300 to positively charge the interventional element 300, thereby enhancing clot adhesion to the interventional element 300. In some cases, electrically enhanced clot adhesion can be improved in the absence of blood flow. As such, it may be especially beneficial to arrest blood flow (e.g., via the balloon 1001 of the first catheter 200 or a flow arrest element of the second catheter 210) while the interventional element 300 is charged, and while withdrawing the thrombus proximally. Instead of or in addition to such blood flow arrest, a flow of saline may be provided from the fluid source 27 toward the interventional element 300 via the second catheter 210 and/or first catheter 200.

With reference to FIGS. 18C-18D, while the interventional element 300 and/or the distal element 140 are engaged with the clot material CM, the clot material CM can be removed. For example, the interventional element 300, with the clot material CM gripped thereby, can be retracted proximally (for example, along with the second catheter 210 and, optionally, the first catheter 200). The second catheter 210, distal element 140, interventional element 300, and associated clot material CM may then be withdrawn from the patient, optionally through one or more larger surrounding catheters. During this retraction, the interventional element 300 can grip the clot material CM electrically and/or electrostatically, e.g., via the application of current from the current generator. Accordingly, the interventional element 300 can maintain an enhanced or electrically and/or electrostatically enhanced grip on the clot material CM during retraction. In other embodiments, the current generator 20 may cease delivery of electrical signals to the interventional element 300 prior to retraction of the interventional element 300 with respect to the vessel V. In some embodiments, the interventional element 300 and clot material CM form a removable, integrated thrombus-device mass wherein the connection of the thrombus to the device is electrically enhanced, e.g. via the application of current as discussed herein.

In FIGS. 18C-18D, the clot material CM has been moved to at least partially enter the second catheter 210. In some embodiments, the clot material CM can substantially block the lumen of the second catheter 210, thereby creating a "corking" effect that may be noticeable to a clinician supplying negative pressure to the second catheter 210 as noted previously. In some embodiments, the current generator 20 can continue to supply electrical signals to the interventional element 300 and the distal element 140 during retraction, while in other embodiments the current generator 20 can cease supplying electrical signals during retraction of the catheter 210 and the clot material CM.

V. Select Embodiments of Waveforms for Electrically Enhanced Retrieval

FIGS. 23A-23E show various electrical waveforms for use with the treatment systems of the present technology. Although the waveforms and other power delivery parameters disclosed herein can be used with the devices and methods described above with respect to FIGS. 19A-22, the waveforms and other parameters are also applicable to other device configurations and techniques. For example, the return electrode can be provided along the catheter wall, as a separate conductive member extending within the catheter lumen, as a needle electrode provided elsewhere in the body, etc. In each of these device configurations, the power delivery parameters and waveforms can be beneficially employed to promote clot adhesion without damaging surrounding tissue. Additionally, although the waveforms and other power delivery parameters disclosed herein may be used for treating a cerebral or intracranial embolism, other applications and other embodiments in addition to those described herein are within the scope of the technology. For example, the waveforms and power delivery parameters disclosed herein may be used to electrically enhance removal of emboli from body lumens other than blood vessels (e.g., the digestive tract, etc.) and/or may be used to electrically enhance removal of emboli from blood vessels outside of the brain (e.g., pulmonary blood vessels, blood vessels within the legs, etc.).

Figure 23A:
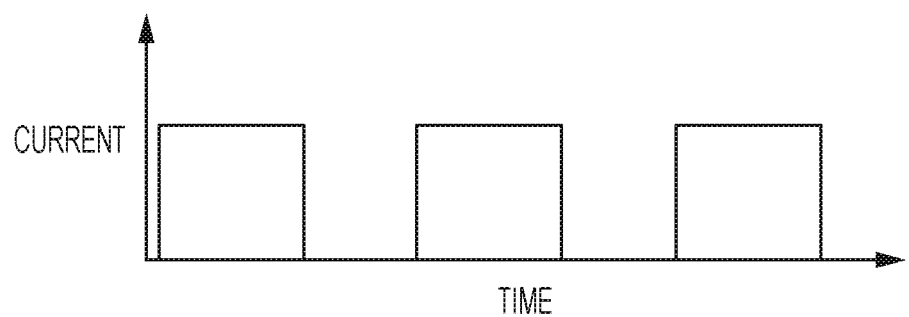
FIG. 23A illustrates a sample waveform for electrically enhanced removal of material from vessel lumens in accordance with one or more embodiments of the present disclosure.
Figure 23B:
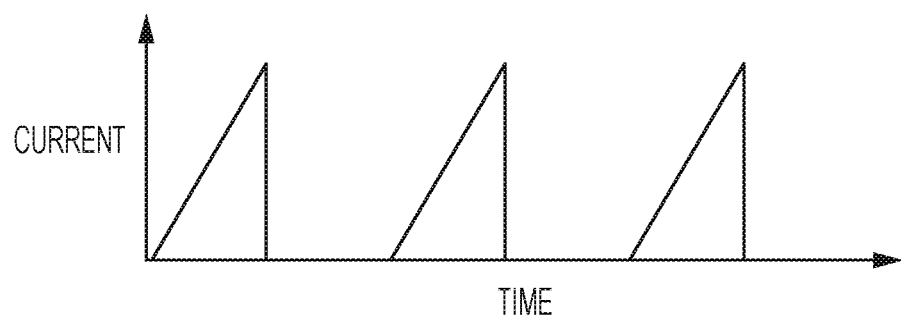
FIG. 23B illustrates a sample waveform for electrically enhanced removal of material from vessel lumens in accordance with one or more embodiments of the present disclosure.
Figure 23C:
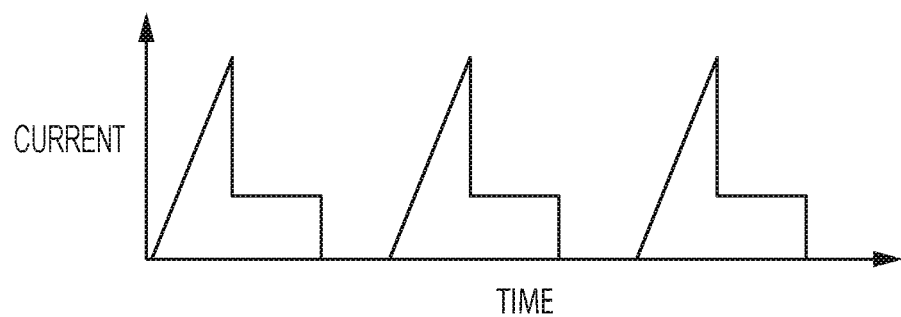
FIG. 23C illustrates a sample waveform for electrically enhanced removal of material from vessel lumens in accordance with one or more embodiments of the present disclosure.
Figure 23D:
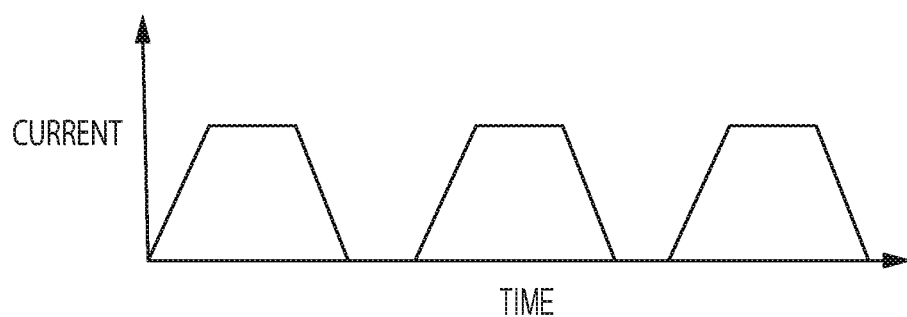
FIG. 23D illustrates a sample waveform for electrically enhanced removal of material from vessel lumens in accordance with one or more embodiments of the present disclosure.
Figure 23E:
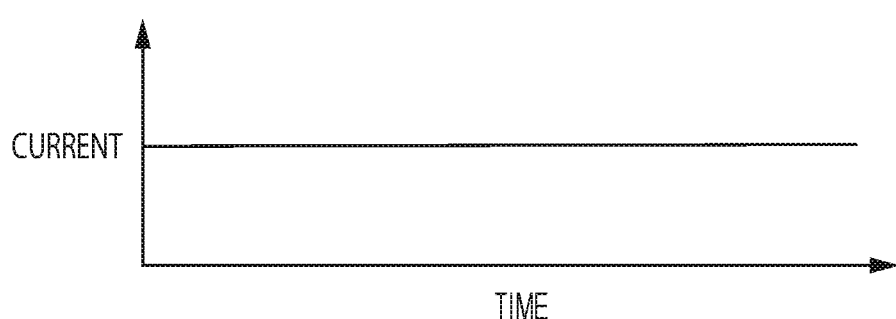
FIG. 23E illustrates a sample waveform for electrically enhanced removal of material from vessel lumens in accordance with one or more embodiments of the present disclosure.

While applying a continuous uniform direct current (DC) electrical signal (as shown in FIG. 23E) to positively charge the interventional element and/or aspiration catheter can improve attachment to the thrombus, this can risk damage to surrounding tissue (e.g., ablation), and sustained current at a relatively high level may also be thrombogenic (i.e., may generate new clots). For achieving effective clot-grabbing without ablating tissue or generating substantial new clots at the treatment site, periodic waveforms have been found to be particularly useful. Without wishing to be bound by theory, the clot-adhesion effect appears to be most closely related to the peak current of the delivered electrical signal. Periodic waveforms can advantageously provide the desired peak current without delivering excessive total energy or total electrical charge. Periodic, non-square waveforms in particular are well suited to deliver a desired peak current while reducing the amount of overall delivered energy or charge as compared to either uniform applied current or square waveforms.

FIGS. 23A-23D illustrate various periodic waveforms that can be used with the devices and methods described above with respect to FIGS. 19A-22, as well as with other devices and techniques. FIG. 23E illustrates a continuous uniform DC electrical signal which can also be used in some embodiments. Referring to FIGS. 23A-23D, electrical power can be delivered according to these waveforms as pulsed direct current. FIGS. 23A and 23B illustrate periodic square and triangular waveforms, respectively. These two waveforms have the same amplitude, but the triangular waveform is able to deliver the same peak current as the square waveform, with only half of the total charge delivered, and less total energy delivered. FIG. 23C illustrates another pulsed-DC or periodic waveform which is a composite of a square waveform and a triangular waveform. This superposition of a triangular waveform and a square waveform shown in FIG. 23C delivers additional efficacy compared to the triangular waveform of FIG. 23B while nonetheless delivering less overall energy than the square waveform of FIG. 23A. This is because the delivered energy is proportional to the square of current and the brief high peak in the composite waveform of FIG. 23C ensures that current is supplied without dispensing excessive energy. FIG. 23D illustrates yet another non-square waveform, in this case a trapezoidal waveform in which "ramp-up" and "ramp-down" portions at the beginning and end of each pulse provide periods of reduced current compared to square waveforms. In other embodiments, different non-square waveforms can be used, including a superposition of a square waveform with any non-square waveform, depending on the desired power delivery characteristics.

The waveform shape (e.g., pulse width, duty cycle, amplitude) and length of time can each be selected to achieve desired power delivery parameters, such as overall electrical charge, total energy, and peak current delivered to the interventional element and/or catheter. In some embodiments, the overall electrical charge delivered to the distal element, interventional element and/or catheter can be between about 30-1200 mC, or between about 120-600 mC. According to some embodiments, the total electrical charge delivered to the distal element, interventional element and/or catheter may be less than 600 mC, less than 500 mC, less than 400 mC, less than 300 mC, less than 200 mC, or less than 100 mC.

In some embodiments, the total energy delivered to the distal element, interventional element, and/or aspiration catheter can be between about 0.75-24,000 mJ, or between about 120-24,000 mJ, or between about 120-5000 mJ. According to some embodiments, the total energy delivered to the distal element, interventional element, and/or aspiration catheter may be less than 24,000 mJ, less than 20,000 mJ, less than 15,000 mJ, less than 10,000 mJ, less than 5,000 mJ, less than 4,000 mJ, less than 3,000 mJ, less than 2000 mJ, less than 1,000 mJ, less than 900 mJ, less than 800 mJ, less than 700 mJ, less than 600 mJ, less than 500 mJ, less than 400 mJ, less than 300 mJ, or less than 200 mJ, or less than 120 mJ, or less than 60 mJ, or less than 48 mJ, or less than 30 mJ, or less than 12 mJ, or less than 6 mJ, or less than 1.5 mJ.

In some embodiments, the peak current delivered can be between about 0.5-20 mA, or between about 0.5-5 mA. According to some embodiments, the peak current delivered may be greater than 0.5 mA, greater than 1 mA, greater than 1.5 mA, greater than 2 mA, greater than 2.5 mA, or greater than 3 mA.

The duration of power delivery is another important parameter that can be controlled to achieve the desired clot-adhesion effects without damaging tissue at the treatment site or generating new clots. In at least some embodiments, the total energy delivery time can be no more than 1 minute, no more than 2 minutes, no more than 3 minutes, no more than 4 minutes, or no more than 5 minutes. According to some embodiments, the total energy delivery time may be less about 30 seconds, less than about 1 minute, less than about 90 seconds, or less than about 2 minutes. As used herein, the "total energy delivery time" refers to the time period during which the waveform is supplied to the interventional element and/or catheter (including those periods of time between pulses of current).

The duty cycle of the applied electrical signal can also be selected to achieve the desired clot-adhesion characteristics without ablating tissue or promoting new clot formation. In some embodiments, the duty cycle can be between about 5% about 99% or between about 5% to about 20%. According to some embodiments, the duty cycle may be about 10%, about 20%, about 30%, about 40%, or about 50%. In yet other embodiments, a constant current may be used, in which the duty cycle is 100%. For 100% duty cycle embodiments, a lower time or current may be used to avoid delivering excess total energy to the treatment site.

Table 1 presents a range of values for power delivery parameters of different waveforms. For each of the conditions set forth in Table 1, a resistance of 1 kohm and a frequency of 1 kHz (for the Square, Triangle, and Composite conditions) was used. The Constant conditions represent a continuous and steady current applied for the duration, i.e. 100% duty cycle. The Peak Current 1 column represents the peak current for the corresponding waveform. For the Composite conditions, the Peak Current 2 column indicates the peak current of the second portion of the waveform. For example, referring back to FIG. 23C, Peak Current 1 would correspond to the current at the top of the triangular portion of the waveform, while Peak Current 2 would correspond to the current at the top of the square portion of the waveform.

delivered of only 120 mC, and condition Composite 1 has a peak current of 20 mA and a total charge delivered of only 144 mC. As such, these non-square waveforms provide additional benefits by delivering desirable peak current while reducing the overall charge delivered to the treatment site.

Although Table 1 represents a series of waveforms with a single frequency (1 kHz), in some embodiments the frequency of the pulsed-DC waveforms can be controlled to achieve the desired effects. For example, in some embodiments the frequency of the waveform can be between 1 Hz and 1 MHz, between 1 Hz and 1 kHz, or between 500 Hz to 1 kHz.

IV. Conclusion

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present

TABLE 1

| Condition | Peak Current 1 (mA) | Peak Current 2 (mA) | Duty Cycle 1 (%) | Duty Cycle 2 (%) | Peak Voltage (V) | Pulse Width (ms) | Total Time (s) | Total Charge (mC) | Total Energy (@ R = 1000 ohm) (mJ) | Total Energy (@ R = 50 ohm) (mJ) |
|---|---|---|---|---|---|---|---|---|---|---|
| Constant 1 | 2 | 0 | 100 | 0 | 2 | n/a | 120 | 240 | 480 | 24 |
| Constant 2 | 2 | 0 | 100 | 0 | 2 | n/a | 60 | 120 | 240 | 12 |
| Constant 3 | 10 | 0 | 100 | 0 | 10 | n/a | 60 | 600 | 6000 | 300 |
| Constant 4 | 20 | 0 | 100 | 0 | 20 | n/a | 60 | 1200 | 24000 | 1200 |
| Constant 5 | 10 | 0 | 100 | 0 | 10 | n/a | 120 | 1200 | 12000 | 600 |
| Constant 6 | 1 | 0 | 100 | 0 | 1 | n/a | 120 | 120 | 120 | 6 |
| Constant 7 | 0.5 | 0 | 100 | 0 | 1 | n/a | 120 | 60 | 30 | 1.5 |
| Constant 8 | 0.5 | 0 | 100 | 0 | 1 | n/a | 60 | 30 | 15 | 0.75 |
| Square 1 | 10 | 0 | 10 | 0 | 10 | 0.1 | 120 | 120 | 1200 | 60 |
| Square 2 | 4 | 0 | 50 | 0 | 4 | 0.5 | 120 | 240 | 960 | 48 |
| Square 3 | 20 | 0 | 10 | 0 | 20 | 0.1 | 120 | 240 | 4800 | 240 |
| Square 4 | 20 | 0 | 10 | 0 | 20 | 0.1 | 60 | 120 | 2400 | 120 |
| Square 5 | 10 | 0 | 10 | 0 | 10 | 0.1 | 60 | 60 | 600 | 30 |
| Triangle 1 | 10 | 0 | 10 | 0 | 10 | 0.1 | 120 | 60 | 1200 | 60 |
| Triangle 2 | 20 | 0 | 10 | 0 | 20 | 0.1 | 120 | 120 | 4800 | 240 |
| Composite 1 | 20 | 1 | 10 | 20 | 20 | 0.3 | 120 | 144 | 4824 | 264 |
| Composite 2 | 10 | 2 | 10 | 20 | 10 | 0.3 | 120 | 108 | 1296 | 156 |

As seen in Table 1, the periodic waveforms (Square, Triangle, and Composite conditions) achieve higher peak currents with lower overall charge delivered than the corresponding Constant conditions. For example, in condition Constant 4, a peak current of 20 mA corresponds to a total energy delivered of 24,000 mJ, while condition Square 3 delivers a peak current of 20 mA with a total energy of only 4,800 mJ. Conditions Triangle 2 and Composite 1 similarly deliver lower total energy while maintaining a peak current of 20 mA. Since clot-adhesion appears to be driven by peak current, these periodic waveforms can therefore offer improved clot adhesion while reducing the risk of damaging tissue at the treatment site or promoting new clot formation. Table 1 also indicates that the Triangle and Composite conditions achieve higher peak currents with lower overall charge delivered than the corresponding Square conditions. For example, condition Square 3 has a peak current of 20 mA and a total charge delivered of 240 mC, while condition Triangle 2 has a peak current of 20 mA but a total charge technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

The invention claimed is:

1. A treatment device, comprising:
   a guidewire having a proximal portion and a distal portion configured to be positioned within a blood vessel at a treatment site at or near a thrombus; and
   a distal element having a proximal end portion and a distal end portion, the proximal end portion directly coupled to the distal portion of the guidewire via a connection assembly and the distal end portion comprising a curved distal end surface, wherein the distal end portion is unattached to the guidewire such that the distal end portion can move freely with respect to the guidewire, and wherein the distal element comprises an expandable mesh having a constrained state for delivery to the treatment site and an expanded state, wherein the distal element has an aperture at a distal portion thereof and the guidewire extends through the aperture, and wherein the distal element is configured to rotate about the guidewire,
   wherein, in the expanded state, the distal element is configured to expand into contact with the blood vessel wall at the treatment site and anchor and/or stabilize the guidewire within the blood vessel.

2. The treatment device of claim 1, wherein an edge of the aperture is formed by the mesh.

3. The treatment device of claim 2, wherein the edge of the aperture is formed by the mesh around an entire perimeter of the aperture.

4. The treatment device of claim 2, wherein the mesh comprises filaments, and the filaments form the edge of the aperture.

5. The treatment device of claim 1, wherein the guidewire extends through at least a portion of a cavity of the distal element.

6. The treatment device of claim 1, wherein the guidewire comprises an elongated tubular element having a lumen extending therethrough.

7. The treatment device of claim 6, wherein the elongated tubular element is a hypotube.

8. The treatment device of claim 6, wherein a distal portion of the elongated tubular element is joined to a proximal portion of the connection assembly.

9. The treatment device of claim 1, further comprising a coil positioned around a region of the guidewire that is proximal to the connection assembly.

10. The treatment device of claim 1, further comprising a coil positioned around a region of the guidewire that is distal to the connection assembly.

11. The treatment device of claim 1, wherein the expandable mesh comprises a plurality of filaments.

12. The treatment device of claim 11, wherein each of the filaments has a first end and a second end opposite the first end, and wherein both the first and second ends of the filaments are fixed relative to one another at the connection assembly.

13. The treatment device of claim 11, wherein each of the filaments terminate at only one end of the distal element.

14. The treatment device of claim 13, wherein the filaments form an opening at an end of the distal element opposite the only one end.

15. The treatment device of claim 1, wherein the mesh has a globular shape.

16. The treatment device of claim 1, wherein the distal element has a central portion between the proximal and distal end portions, and wherein the distal element has a greater radial dimension along the central portion than along the proximal and distal portions.

17. A treatment device, comprising:
    a guidewire having a proximal portion and a distal portion configured to be positioned within a blood vessel at a treatment site at or near a thrombus; and
    a distal element having a proximal region, a distal region, and an aperture at the distal region with the guidewire positioned therethrough, wherein the proximal region is directly coupled to the distal portion of the guidewire via a connection assembly and the distal region is unattached to the guidewire such that the distal region can move freely with respect to the guidewire, and wherein the distal element is configured to rotate about the guidewire,
    wherein the distal element comprises an expandable mesh having a constrained state for delivery to the treatment site and an expanded state, wherein the mesh extends distally and radially inwardly along the distal region towards the aperture, and
    wherein, in the expanded state, the distal element is configured to expand into contact with the blood vessel wall at the treatment site and anchor and/or stabilize the guidewire within the blood vessel.

18. The treatment device of claim 17, wherein the mesh has a globular shape.

* * * * *

UNITED STATES PATENT AND TRADEMARK OFFICE
CERTIFICATE OF CORRECTION

PATENT NO. : 11,523,838 B2
APPLICATION NO. : 16/439642
DATED : December 13, 2022
INVENTOR(S) : Nguyen et al.

It is certified that error appears in the above-identified patent and that said Letters Patent is hereby corrected as shown below:

On the Title Page

Item (57), in Column 2, under "Abstract", Line 2, delete "mesh," and insert -- mesh. --, therefor.

Item (57), in Column 2, under "Abstract", Line 3, delete "a treatment" and insert -- A treatment --, therefor.

Signed and Sealed this
Thirty-first Day of January, 2023

*Katherine Kelly Vidal*

Katherine Kelly Vidal
*Director of the United States Patent and Trademark Office*